(12) United States Patent
Brown et al.

(10) Patent No.: US 7,067,541 B2
(45) Date of Patent: Jun. 27, 2006

(54) 2-AMINO-PYRIDINE DERIVATIVES USEFUL FOR THE TREATMENT OF DISEASES

(75) Inventors: Alan Daniel Brown, Sandwich (GB); Justin Stephen Bryans, Sandwich (GB); Charlotte Alice Louise Lane, Sandwich (GB); Simon John Mantell, Sandwich (GB)

(73) Assignee: Pfizer Inc, New York, NY (US)

( * ) Notice: Subject to any disclaimer, the term of this patent is extended or adjusted under 35 U.S.C. 154(b) by 142 days.

(21) Appl. No.: 10/860,771

(22) Filed: Jun. 3, 2004

(65) Prior Publication Data

US 2005/0004182 A1    Jan. 6, 2005

Related U.S. Application Data

(60) Provisional application No. 60/527,600, filed on Dec. 5, 2003, provisional application No. 60/527,421, filed on Dec. 5, 2003.

(30) Foreign Application Priority Data

Jun. 4, 2003  (GB) .................. 0312840.2
Jun. 4, 2003  (GB) .................. 0312842.8

(51) Int. Cl.
*A61K 31/47* (2006.01)
*C07D 211/72* (2006.01)

(52) U.S. Cl. ........................ 514/352; 546/311
(58) Field of Classification Search .............. 546/311; 514/352
See application file for complete search history.

(56) References Cited

U.S. PATENT DOCUMENTS

| | | | |
|---|---|---|---|
| 4,358,455 A | 11/1982 | Atkinson et al. | 424/263 |
| 4,863,939 A | 9/1989 | Lindel et al. | 514/357 |
| 5,714,506 A | 2/1998 | Fisher et al. | 514/352 |
| 6,844,362 B1 * | 1/2005 | Brown et al. | 514/419 |

FOREIGN PATENT DOCUMENTS

| | | |
|---|---|---|
| WO | WO9529259 | 11/1995 |
| WO | WO0142193 | 6/2001 |
| WO | WO03024439 | 3/2003 |

OTHER PUBLICATIONS

Barnes, P. J. Chest, 1997, 111:2, pp. 17S-26S.
Bryan, S.A. et al., Expert Opinion on Investigational Drugs, 2000, 9:1, p. 25-42.

* cited by examiner

*Primary Examiner*—James O. Wilson
*Assistant Examiner*—Binta Robinson
(74) *Attorney, Agent, or Firm*—Gregg C. Benson; Robert T. Ronau

(57) ABSTRACT

The invention relates to compounds of formula (1)

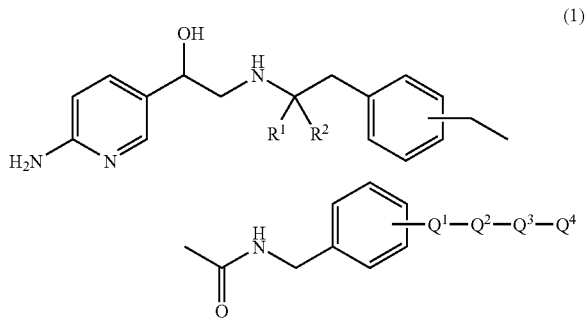

and to processes for the preparation of, intermediates used in the preparation of, compositions containing and the uses of, such derivatives. The compounds according to the present invention are useful in numerous diseases, disorders and conditions, in particular inflammatory, allergic and respiratory diseases, disorders and conditions.

19 Claims, No Drawings

2-AMINO-PYRIDINE DERIVATIVES USEFUL FOR THE TREATMENT OF DISEASES

This invention relates to β2 agonists of general formula (1):

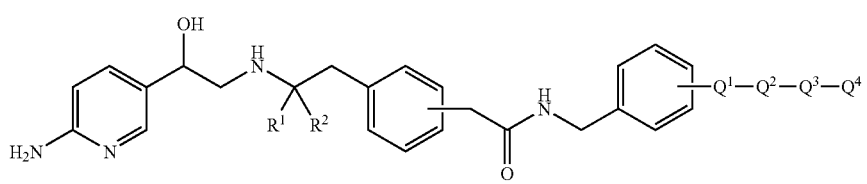

in which $R^1$, $R^2$, $Q^1$, $Q^2$, $Q^3$ and $Q^4$ have the meanings indicated below,
and to processes for the preparation of, intermediates used in the preparation of, compositions containing and the uses of, such derivatives.

Adrenoceptors are members of the large G-protein coupled receptor super-family. The adrenoceptor subfamily is itself divided into the α and β subfamilies with the β sub-family being composed of at least 3 receptor sub-types: β1, β2 and β3. These receptors exhibit differential expression patterns in tissues of various systems and organs of mammals. β2 adrenergic (β2) receptors are mainly expressed in smooth muscle cells (e.g. vascular, bronchial, uterine or intestinal smooth muscles), whereas β3 adrenergic receptors are mainly expressed in fat tissues (therefore β3 agonists could potentially be useful in the treatment of obesity and diabetes) and β1 adrenergic receptors are mainly expressed in cardiac tissues (therefore β1 agonists are mainly used as cardiac stimulants).

The pathophysiology and treatments of airway diseases have been extensively reviewed in the literature (for reference see Barnes, P. J. Chest, 1997, 111:2, pp 17S–26S and Bryan, S. A. et al, Expert Opinion on investigational drugs, 2000, 9:1, pp25–42) and therefore only a brief summary will be included here to provide some background information.

Glucocorticosteroids, anti-leukotrienes, theophylline, cromones, anti-cholinergics and β2 agonists constitute drug classes that are currently used to treat allergic and non-allergic airways diseases such as asthma and chronic obstructive airways disease (COPD). Treatment guidelines for these diseases include both short and long acting inhaled β2 agonists. Short acting, rapid onset β2 agonists are used for "rescue" bronchodilation, whereas, long-acting forms provide sustained relief and are used as maintenance therapy.

Bronchodilation is mediated via agonism of the β2 adrenoceptor expressed on airway smooth muscle cells, which results in relaxation and hence bronchodilation. Thus, as functional antagonists, β2 agonists can prevent and reverse the effects of all bronchoconstrictor substances, including leukotriene D4 (LTD4), acetylcholine, bradykinin, prostaglandins, histamine and endothelins. Because β2 receptors are so widely distributed in the airway, β2 agonists may also affect other types of cells that play a role in asthma. For example, it has been reported that β2 agonists may stabilize mast cells. The inhibition of the release of bronchoconstrictor substances may be how β2 agonists block the bronchoconstriction induced by allergens, exercise and cold air. Furthermore, β2 agonists inhibit cholinergic neurotransmission in the human airway, which can result in reduced cholinergic-reflex bronchoconstriction.

In addition to the airways, it has also been established that β2 adrenoceptors are also expressed in other organs and tissues and thus β2 agonists, such as those described in the present invention, may have application in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

However, numerous β2 agonists are limited in their use due to their low selectivity or adverse side-effects driven by high systemic exposure and mainly mediated through action at β2 adrenoreceptors expressed outside the airways (muscle tremor, tachycardia, palpitations, restlessness). Therefore there is a need for improved agents in this class.

Accordingly, there is still a need for novel β2 agonists that would have an appropriate pharmacological profile, for example in terms of potency, selectivity and/or pharmacodynamic properties. In this context, the present invention relates to novel β2 agonists.

Various 2-amino-pyridine derivatives have already been synthesised. For example, the U.S. Pat. No. 4,358,455 discloses compounds having a random activity either as beta-adrenergic stimulants or as beta-adrenergic blockers, of formula:

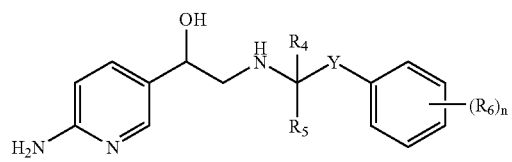

wherein $R_4$ and $R_5$ are independently selected from H and $(C_1–C_3)$alkyl; Y may namely be a methylene group, $R_6$ is selected from H, OH, alkoxy, methylenedioxy, halo or alkyl; and n is equal to 1 or 2.

Another example concerns the patent application WO 95/29259 that discloses selective β3 agonists (with little β1 and β2 activity) of formula:

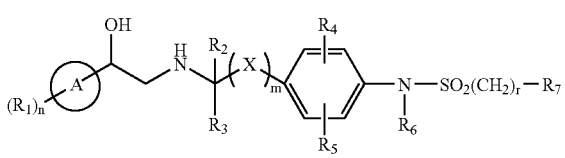

wherein A may be a 6-membered heterocyclic ring with from 1 to 4 heteroatoms selected from O, S and N; $R_1$ may be amino and n may be equal to 1; $R_2$, $R_3$ may be independently H or $(C_1–C_{10})$alkyl; m is 0 or 1, and X may be a methylene group; $R_4$, $R_5$ may be H; $R_6$ is H or $(C_1–C_{10})$ alkyl; r is 0 to 3 and $R_7$ may be a phenyl 0 to 5 times substituted by numerous substituents (OH, oxo, Hal, CN etc. . . . ).

Other 2-amino-pyridine derivatives are also disclosed in U.S. Pat. No. 5,714,506 as selective β3 agonists They are more specifically of formula:

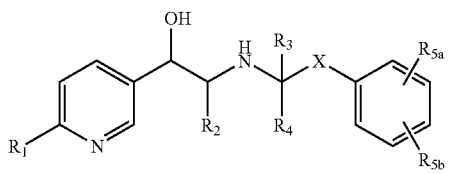

wherein $R_1$ may be amino; $R_2$ is H or $(C_1–C_6)$alkyl; $R_3$ and $R_4$ may be independently H or $(C_1–C_{12})$alkyl; X may be a —$(CH_2)_n$— group with n selected from 1, 2 and 3; and $R_{5a}$ and $R_{5b}$ may be chosen from —$CONR_2R_2$, —O—$CH_2$— $CONR_2R_2$, aryl, —$CH_2$-alkoxy, —$CH_2$—$CONR_2R_2$ wherein $R_2$ is H or $(C_1–C_6)$alkyl.

However, none of the 2-amino-pyridine derivatives synthesised so far have shown a selective β2 agonist activity, allowing them to be used as efficient drugs in the treatment of the β2-mediated diseases and/or conditions, in particular allergic and non-allergic airways diseases or other diseases such as those previously cited.

The invention relates to the compounds of general formula (1):

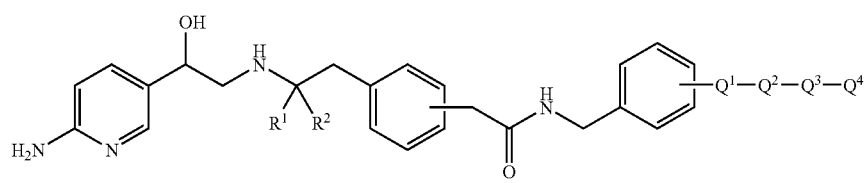

(1)

wherein the $CH_2$—C(=O)NH-benzyl-$Q^1$-$Q^2$-$Q^3$-$Q^4$ group is in the meta or para position, and $R^1$ and $R^2$ are independently selected from H and $C_1$–$C_4$ alkyl;

$Q^1$ is $(CH_2)_n$ wherein n is an integer selected from 0 and 1;

$Q^2$ is a group selected from —C(=O)NH—, —NHC (=O)—, and —$SO_2$NH—;

$Q^3$ is a single bond, a $C_1$–$C_4$ alkylene optionally substituted with OH or a group $(CH_2)_m$—O—$(CH_2)_p$ wherein m and p are integers independently selected from 1, 2 or 3;

$Q^4$ is selected from

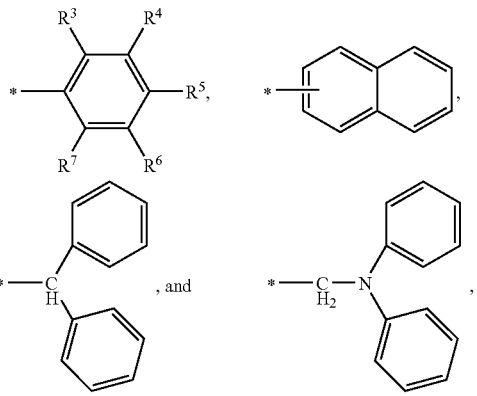

wherein * represents the attachment point to $Q^3$ and $R^3$, $R^4$, $R^5$, $R^6$ and $R^7$ are independently selected from H, $C_1$–$C_4$ alkyl, $OR^8$, $SR^8$, halo, $CF_3$, $OCF_3$, $COOR^9$, $SO_2NR^8R^9$, $CONR^8R^9$, $NHR^8R^9$, $NHCOR^9$, $CH_2$—NHC(=O)NH—$R^9$ provided at least 2 of $R^3$ to $R^7$ are equal to H;

wherein $R^8$ is selected from H or $C_1$–$C_4$ alkyl and $R^9$ is selected from H, $C_1$–$C_4$ alkyl, benzyl optionally substituted with 1, 2, 3 or 4 $C_1$–$C_4$ alkoxy, and a group

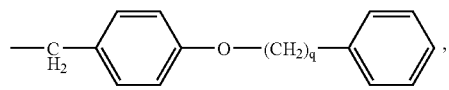

wherein q is an integer selected from 0, 1, 2 and 3;

or, if appropriate, their pharmaceutically acceptable salts and/or isomers, tautomers, solvates or isotopic variations thereof.

The compounds of formula (1) are agonists of the β2 receptors, that are particularly useful for the treatment of β2-mediated diseases and/or conditions, and show good potency, in particular when administered via the inhalation route.

Preferably, the term "selective" means that the compounds of formula (1) show an agonist potency for the β2 receptor, which is at least about 100-fold higher as for the β3 receptor and at least about 500-fold higher as for the β1 receptor.

Preferably, the compounds of formula (1) show an agonist potency for the β2 receptor, which is less than 10 nM as measured by the cell-based assay described herein.

In the here above general formula (1), $C_1$–$C_4$ alkyl and $C_1$–$C_4$ alkylene denote a straight-chain or branched group containing 1, 2, 3 or 4 carbon atoms. This also applies if they carry substituents or occur as substituents of other radicals, for example in O—($C_1$–$C_4$)alkyl radicals, S—($C_1$–$C_4$)alkyl radicals etc . . . . Examples of suitable ($C_1$–$C_4$)alkyl radicals are methyl, ethyl, n-propyl, iso-propyl, n-butyl, iso-butyl, sec-butyl, tert-butyl. . . . Examples of suitable ($C_1$–$C_4$) alkoxy radicals are methoxy, ethoxy, n-propyloxy, iso-propyloxy, n-butyloxy, iso-butyloxy, sec-butyloxy and tert-butyloxy. . . .

Finally, halo denotes a halogen atom selected from the group consisting of fluoro, chloro, bromo and iodo in particular fluoro or chloro.

In the following, the free bond on the phenyl group such as in the structure below,

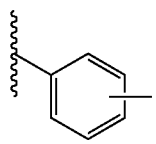

means that the phenyl can be substituted in the meta or para position.

The 2-amino-pyridine derivatives of the formula (1) can be prepared using conventional procedures such as by the following illustrative methods in which $R^1$, $R^2$, $Q^1$, $Q^2$, $Q^3$ and $Q^4$ are as previously defined for the 2-amino-pyridine derivatives of the formula (1) unless otherwise stated.

The 2-amino-pyridine derivatives of the formula (1) may be prepared by removal of the protecting group(s) "Prot" from the compound of formula (2):

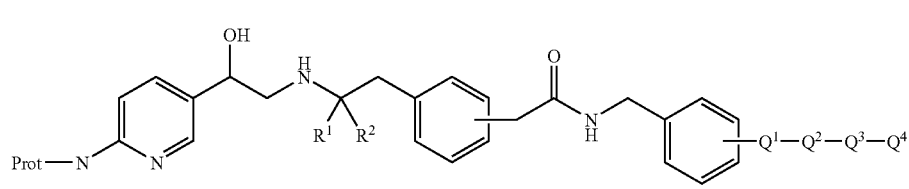

wherein $R^1$, $R^2$, $Q^1$, $Q^2$, $Q^3$ and $Q^4$ are as previously described for the 2-amino-pyridine derivatives of formula (1) and Prot is a suitable protecting group (or 2 suitable protecting groups) for the amino-pyridine, which include but is not limited to tert-butoxycarbonyl, acyl or 2,5-dimethyl pyrrole, by methods well known to those skilled in the art such as standard methodology for cleaving nitrogen protecting groups as found in textbooks (e.g. T. W. GREENE, *Protective Groups in Organic Synthesis*, A. Wiley-Interscience Publication, 1981).

The compound of formula (2) may be prepared by coupling an acid of formula (3):

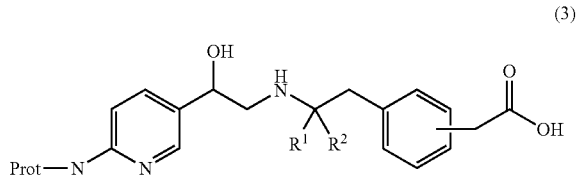

wherein Prot, $R^1$ and $R^2$ are as previously defined, with an amine of formula (4):

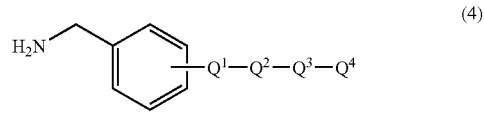

wherein $Q^1$, $Q^2$, $Q^3$ and $Q^4$ are as previously defined.

The coupling of the acid (3) to the amine (4) is generally carried out in an excess of said amine, with a conventional coupling agent (e.g. 1-(3-dimethylaminopropyl)-3-ethylcarbodiimide hydrochloride or N,N'-dicyclohexylcarbodiimide), optionally in the presence of a catalyst (e.g. 1-hydroxybenzotriazole hydrate or 1-hydroxy-7-azabenzotriazole), and optionally in the presence of a tertiary amine base (e.g. N-methylmorpholine, triethylamine or N,N-diisopropylethylamine). The reaction may be undertaken in a suitable solvent such as pyridine, N,N-dimethylformamide, tetrahydrofuran, dimethylsulfoxide, dichloromethane or ethyl acetate, and at temperature comprised between 10° C. and 40° C. (room temperature).

Alternatively, the compound of formula (2) may be prepared by coupling the acid (3) with an amine of formula (5):

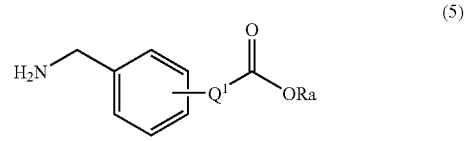

wherein Q¹ is as previously defined and Ra is a suitable acid protecting group, preferably a $(C_1-C_4)$alkyl group, which includes, but is not limited to, methyl and ethyl. The resulting ester is hydrolysed to give the acid, which is then subjected to further coupling with an amine of formula $HNQ^3Q^4$ (selected from a range of commercially available amines, or prepared according to standard methodology well known to the man skilled in the art), to give the compound of formula (2) where Q² represents the group of formula —C(=O)NH—.

In a typical procedure, the hydrolysis of the ester to give an acid is undertaken according to any method well known to the man skilled in the art to prepare an acid from an ester, without modifying the rest of the molecule. For example, the ester may be hydrolysed by treatment with aqueous acid or base (e.g. hydrochloric acid, potassium hydroxide, sodium hydroxide or lithium hydroxide), optionally in the presence of a co-solvent (e.g. tetrahydrofuran/1,4-dioxan), at a temperature comprised between 20° C. and 100° C., for a period of 1 to 40 hours.

Said amine (4) is either commercially available or may be prepared by conventional methods well-known to the one skilled in the art (e.g. acylation, sulfonylation, reduction, oxidation, alkylation, protection, deprotection etc. . . . ) from commercially available materials.

The acid of formula (3) may be prepared from the corresponding ester of formula (6):

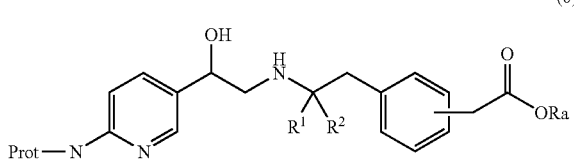

(6)

wherein Prot, $R^1$, $R^2$ and Ra are as previously defined according to any method well-known to the one skilled in the art to prepare an acid from an ester, without modifying the rest of the molecule, as previously described.

The ester of formula (6) may be prepared according to different routes depending on the choice of $R^1$ and $R^2$.

If $R^1$ is hydrogen and $R^2$ is $(C_1-C_4)$alkyl the ester of formula (6) may be prepared by reaction of an amine of formula (7):

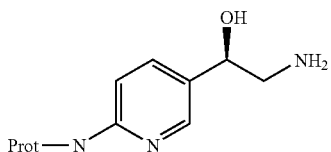

(7)

with an excess of a ketone of formula (8):

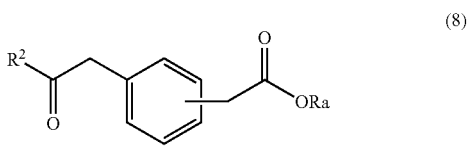

(8)

wherein Prot, $R^2$ and Ra are as previously defined, to form an intermediate compound, which is reduced by a suitable reducing agent (e.g. sodium cyanoborohydride of formula $NaCN(BH)_3$ or sodium triacetoxyborohydride of formula $Na(OAc)_3BH$), optionally in the presence of sodium acetate or acetic acid. The reaction is generally done in a suitable solvent such as tetrahydrofuran or dichloromethane, at temperature comprised between 20° C. and 80° C. for 3 to 72 hours, giving the compound of formula (6) as a mixture of diastereomers. According to another alternative, the reduction may be carried out in the presence of a drying agent such as molecular sieves or magnesium sulfate.

The amine of formula (7) may be prepared starting from a 2-amino-5-bromo-pyridine as described in EP 1 078 924 or WO 99/32475.

Alternatively, if $R^1$ is hydrogen and $R^2$ is $(C_1-C_4)$alkyl the ester of formula (6) may be prepared according to scheme 1 as follows:

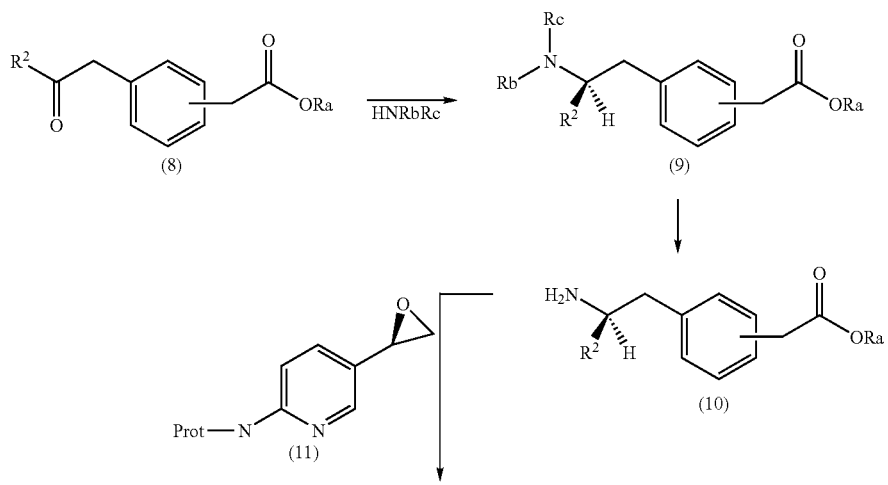

Scheme 1

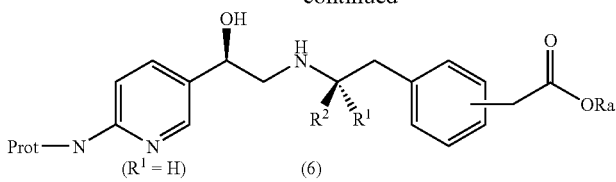

wherein Ra and Prot are as previously defined, and Rb and Rc represent any suitable substituents so that HNRbRc is a chiral amine (for example, Rb may be hydrogen and Rc may be a α-methylbenzyl group) and the bonds between N and Rb and N and Rc can be easily cleaved to give the free amine of formula (10).

In a typical procedure, the ketone of formula (8) is reacted with a suitable chiral non-racemic amine HNRbRc (e.g. α-methylbenzylamine or any other commercially available chiral non-racemic amine) to form a chiral intermediate, which is reduced by a suitable reducing agent (e.g. sodium cyanoborohydride of formula NaCN(BH)$_3$ or sodium triacetatoxyborohydride of formula Na(OAc)$_3$BH) optionally in the presence of acetic acid, and also optionally in the presence of a drying agent (e.g. molecular sieves, magnesium sulfate) as previously described. The resulting product is then converted to the hydrochloride salt and selectively crystallised from a suitable solvent or mixture of solvents (e.g. isopropanol, ethanol, methanol, diisopropyl ether or diisopropyl ether/methanol) to give the diastereomerically pure product of formula (9), or its enantiomer, if the opposite enantiomer of the amine HNRbRc is used.

The protected amine of formula (9) is then cleaved to give the corresponding free amine of formula (10) using standard methodology for cleaving nitrogen protecting groups, such as that found in the text book (see for example T. W. Greene, *Protective Groups in Organic Synthesis*, A. Wiley-Interscience Publication, 1981). When a α-methylbenzylamine is used, then the cleavage may be done using ammonium formate and palladium hydroxide on carbon of formula Pd(OH)$_2$/C as catalyst.

Said amine of formula (10) is then reacted with an epoxide of formula (11) in a suitable solvent or mixture of solvents (e.g. dimethyl sulfoxide/toluene), at a temperature comprised between 20° C. and 80° C. and optionally in the presence of a catalyst for 8 to 40 hours, to give the ester of formula (6).

The epoxide of formula (11) may be prepared starting from starting from a 2-amino-5-bromo-pyridine as described in EP 1 078 924 or WO 99/32475.

The ketone of formula (8) described above may be prepared by enolate arylation of an aryl halide of formula (12):

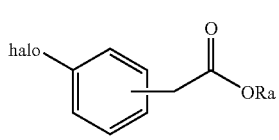

wherein Ra is as previously defined and halo represents an halogen atom, which includes, but is not limited to, fluoro, chloro and bromo.

In a typical procedure, the aryl halide of formula (12) is reacted with a tin enolate generated in situ by treatment of a vinyl acetate (e.g. isoprenyl acetate with tri-n-butyltin methoxide of formula Bu$_3$SnOMe) in the presence of a suitable palladium catalyst (palladium acetate/tri-ortho-tolylphosphine of formula Pd(OAc)$_2$/P(o-Tol)$_3$) in a non-polar solvent (e.g. toluene, benzene, hexane). Preferably, the reaction is carried out at a temperature comprised between 80° C. and 110° C. for 6 to 16 hours.

The aryl halide of formula (12) may be prepared by esterification of the corresponding acid of formula (13):

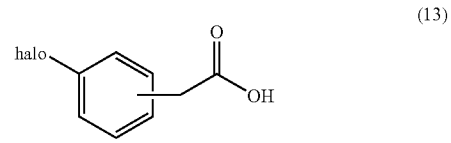

wherein halo is as previously defined, according to any method well-known to the one skilled in the art to prepare an ester from an acid, without modifying the rest of the molecule.

In a typical procedure, the acid of formula (13) is reacted with an alcoholic solvent of formula RaOH, wherein Ra is as previously defined, in the presence of an acid, such as hydrochloric acid, at a temperature between 10° C. and 40° C. (room temperature) for 8 to 16 hours.

According to another alternative, the acid of formula (13) is reacted with a bromoalkyl of formula RaBr in the presence of a suitable base such as cesium carbonate, in a suitable organic solvent (e.g. N,N-dimethylformamide, tetrahydrofuran) at a temperature and for a time as mentioned above.

The acid of formula (13) is either a commercial product or it may be prepared by conventional procedures well-known to the man skilled in the art.

If R$^1$ and R$^2$ are both different from hydrogen, then the ester of formula (6) may be prepared according to scheme 2 as follows:

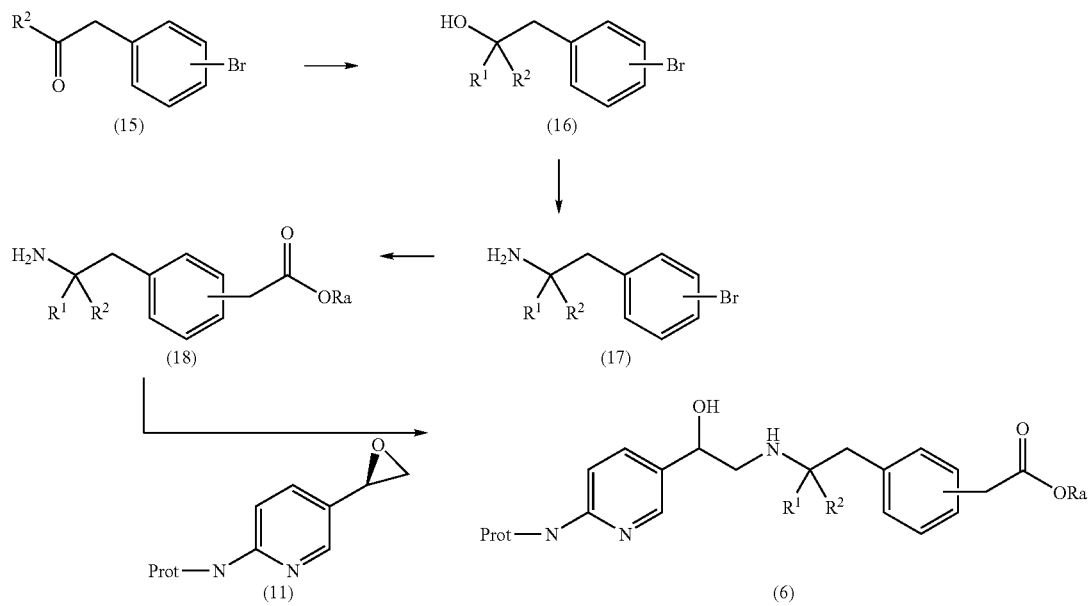

Scheme 2 wherein $R^1$, $R^2$, Ra and Prot' are as previously defined.

In a typical procedure, the halo ketone of formula (15) is reacted with an "activated" alkyl (organometallic alkyl such as $R^2$MgBr, $R^2$MgCl or $R^2$Li) to give the corresponding tertiary alcohol of formula (16). This organometallic addition is generally undertaken in a suitable solvent such as tetrahydrofuran, ether, cyclohexane or 1,4-dioxane, at a temperature comprised between 10° C. and 40° C. (room temperature) for 1 to 24 hours Said tertiary alcohol of formula (16) is then treated with an alkyl nitrile (e.g. acetonitrile, chloroacetonitrile) in the presence of an acid (e.g. sulfuric acid, acetic acid) to give a protected intermediate which in turn is cleaved using standard methodology for cleaving nitrogen protecting group such as those mentioned in textbooks, to give the amine of formula (17).

The amine of formula (17) is then converted to the boronic acid ester by treatment with a suitable boron source (e.g. pinacolborane, bis(pinacolato)diboron) in the presence of a suitable palladium catalyst (e.g. palladium(II)acetate/ tri-ortho-tolylphosphine of formula Pd(OAc)$_2$/P(o-tol)$_3$ or (diphenylphosphino)ferrocenyl palladium(II)chloride of formula dppfPdCl$_2$). The reaction is generally undertaken in a suitable solvent such as dimethyl sulfoxide or toluene, optionally in the presence of a base (e.g. potassium acetate), at a temperature comprised between 60° C. and 110° C. for a period of 4 to 24 hours. The intermediate boronic acid ester is then coupled with ethyl bromoacetate in the presence of a suitable palladium catalyst (e.g. tetrakis(triphenylphosphine)palladium(0) of formula Pd(PPh$_3$)$_4$, palladium acetate/tri-ortho-tolylphosphine of formula Pd(OAc)$_2$/P(o-tol)$_3$ or (diphenylphosphino)ferrocenyl palladium chloride of formula dppfPdCl$_2$) to give the compound of formula (18).

The compound of formula (6) is finally obtained by reaction of the compound of formula (18) with the epoxide of formula (11) as previously described.

The compound of formula (15) is either commercial or it may be easily prepared from commercial compounds by conventional procedures well known to the one skilled in the art.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

For some of the steps of the here above described process of preparation of the 2-amino-pyridine derivatives of formula (1), it can be necessary to protect the potential reactive functions that are not wished to react, and to cleave said protecting groups in consequence. In such a case, any compatible protecting radical can be used. In particular methods of protection and deprotection such as those described by T. W. GREENE (*Protective Groups in Organic Synthesis*, A. Wiley-Interscience Publication, 1981) or by McOMIE (*Protective Groups in Organic Chemistry*, Plenum Press, 1973), can be used.

Also, the 2-amino-pyridine derivatives of formula (1) as well as intermediate for the preparation thereof can be purified according to various well-known methods, such as for example crystallization or chromatography.

In the above compounds of formula (1), the following substitutions are preferred:

$R^1$ is H and $R^2$ is $C_1$–$C_4$ alkyl, more preferably $CH_3$, or $R^1$ and $R^2$ are the same or different and are selected from $C_1$–$C_4$ alkyl, more preferably $R^1$ and $R^2$ are both $CH_3$ and/or, n is 0 and $Q^2$ is —C(=O)NH— or $SO_2$NH—, or n is 1 and $Q^2$ is —NH—C(=O)—, and/or, $Q^3$ is selected from single bond, $CH_2$, CH(—$CH_3$) $CH_2$OH—, CH($CH_3$)—, —CH($CH_2$OH)$CH_2$—, —($CH_2$)$_2$—, —($CH_2$)$_2$—$OCH_2$— and —($CH_2$)$_2$—O— ($CH_2$)$_3$— and/or, $Q^4$ is selected from

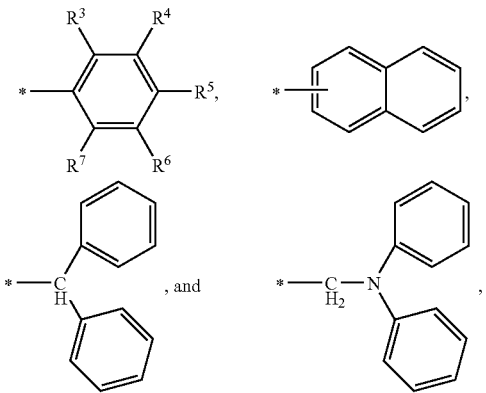

wherein * represents the attachment point to $Q^3$ and $R^3$, $R^4$, $R^5$, $R^6$ and $R^7$ are independently selected from H,
$OR^8$, provided at least 2 of $R^3$ to $R^7$ are equal to H, or $SO_2NR^8R^9$ or $CH_2$—NHC(=O)NH—$R^9$ provided at least 4 of $R^3$ to $R^7$ are equal to H, wherein $R^8$ is selected from H or $C_1$–$C_4$ alkyl and $R^9$ is selected from H, $C_1$–$C_4$ alkyl, benzyl optionally substituted with 1, 2, 3 or 4 $C_1$–$C_4$ alkoxy, and a group

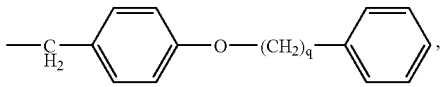

wherein q is an integer selected from 0, 1, 2 and 3.

Preferably, the group $-Q^1-Q^3-Q^3-Q^4$ is in meta or para position.

Compound of particular interest with respect to the present invention are those wherein n is 0 and $Q^2$ is —C(=O)NH—.

Particularly preferred are the compounds of the formula (1) as described in the Examples section hereafter, i.e.:

4-{[2-(3-{2-[(2R)-2-(6-Amino-pyridin-3-yl)-2-hydroxy-ethylamino]-propyl}-phenyl)-acetylamino]-methyl}-N-(3,4-dimethoxy-benzyl)-benzamide, 4-{[2-(3-{2-[(2R)-2-(6-Amino-pyridin-3-yl)-2-hydroxy-ethylamino]-propyl}-phenyl)-acetylamino ]-methyl}-N-(4-sulfamoyl-benzyl)-benzamide, 4-{[2-(3-{2-[(2R)-2-(6-Amino-pyridin-3-yl)-2-hydroxy-ethylamino]-propyl}-phenyl)-acetylamino]methyl}-N-(2-ethoxy-benzyl)-benzamide, 4-{[2-(3-{2-[(2R)-2-(6-Amino-pyridin-3-yl)-2-hydroxy-ethylamino]-propyl}-phenyl)-acetylamino]-methyl}-N-[(1R)-1-(4-methoxy-phenyl)-ethyl]-benzamide, 4-{[2-(3-{2-[(2R)-2-(6-Amino-pyridin-3-yl)-2-hydroxy-ethylamino]-propyl}-phenyl)-acetylamino]-methyl}-N-((1R)-1-hydroxymethyl-2-phenyl-ethyl)-benzamide, 4-{[2-(3-{2-[(2R)-2-(6-Amino-pyridin-3-yl)-2-hydroxy-ethylamino]-propyl}-phenyl)-acetylamino]-methyl}-N-((1R, 2S)-2-hydroxy-1-methyl-2-phenyl-ethyl)-benzamide, 4-{[2-(3-{2-[(2R)-2-(6-Amino-pyridin-3-yl)-2-hydroxy-ethylamino]-propyl}-phenyl)-acetylamino]-methyl}-N-((1S, 2R)-2-hydroxy-1-methyl-2-phenyl-ethyl)-benzamide, 4-{[2-(3-{2-[(2R)-2-(6-Amino-pyridin-3-yl)-2-hydroxy-ethylamino]-propyl}-phenyl)-acetylamino]-methyl}-N-[2-(3-methoxy-phenyl)-ethyl]-benzamide, 4-{[2-(3-{(2R)-2-[(2R)-2-(6-Amino-pyridin-3-yl)-2-hydroxy-ethylamino]-propyl}-phenyl)-acetylamino]-methyl}-N-(3,4-dimethoxy-benzyl)-benzamide, 4-{[2-(3-{(2R)-2-[(2R)-2-(6-Amino-pyridin-3-yl)-2-hydroxy-ethylamino]-propyl}-phenyl)-acetylamino]-methyl}-N-(2-ethoxy-benzyl)-benzamide, 4-{[2-(3-{(2R)-2-[(2R)-2-(6-Amino-pyridin-3-yl)-2-hydroxy-ethylamino]-propyl}-phenyl)-acetylamino]-methyl}-N-(4-hydroxy-3-methoxy-benzyl)-benzamide, 4-{[2-(3-{(2R)-2-[(2R)-2-(6-Amino-pyridin-3-yl)-2-hydroxy-ethylamino]-propyl}-phenyl)-acetylamino]-methyl}-N-(4-sulfamoyl-benzyl)-benzamide, 4-{[2-(3-{(2R)-2-[(2R)-2-(6-Amino-pyridin-3-yl)-2-hydroxy-ethylamino]-propyl}-phenyl)-acetylamino]-methyl}-N-((1R, 2S)-2-hydroxy-1-methyl-2-phenyl-ethyl)-benzamide, N-(4-{[2-(3-{(2R)-2-[(2R)-2-(6-Amino-pyridin-3-yl)-2-hydroxy-ethylamino]-propyl}-phenyl)-acetylamino]-methyl}-benzyl)-2,2-diphenyl-acetamide, 2-(3-{(2R)-2-[(2R)-2-(6-Amino-pyridin-3-yl)-2-hydroxy-ethylamino]-propyl}-phenyl)-N-{4-[(benzhydryl-amino)-methyl]-benzyl}-acetamide, 4-{[2-(3-{(2R)-2-[(2R)-2-(6-Amino-pyridin-3-yl)-2-hydroxy-ethylamino]-propyl}-phenyl)-acetylamino]-methyl}-N-(2-benzyloxy-ethyl)-benzamide, 4-{[2-(3-{(2R)-2-[(2R)-2-(6-Amino-pyridin-3-yl)-2-hydroxy-ethylamino]-propyl}-phenyl)-acetylamino]-methyl}-N-[2-(3-phenyl-propoxy)-ethyl]-benzamide, 4-{[2-(3-{(2R)-2-[(2R)-2-(6-Amino-pyridin-3-yl)-2-hydroxy-ethylamino]-propyl}-phenyl)-acetylamino]-methyl}-N-[2-(naphthalen-1-ylmethoxy)-ethyl]-benzamide, 4-{[2-(3-{(2R)-2-[(2R)-2-(6-Amino-pyridin-3-yl)-2-hydroxy-ethylamino]-propyl}-phenyl)-acetylamino]-methyl}-N-(3-benzylsulfamoyl-benzyl)-benzamide, 4-{[2-(3-{(2R)-2-[(2R)-2-(6-Amino-pyridin-3-yl)-2-hydroxy-ethylamino]-propyl}-phenyl)-acetylamino]-methyl}-N-(4-methylsulfamoyl-benzyl)-benzamide, 4-{[2-(3-{(2R)-2-[(2R)-2-(6-Amino-pyridin-3-yl)-2-hydroxy-ethylamino]-propyl}-phenyl)-acetylamino]-methyl}-N-(4-ethylsulfamoyl-benzyl)-benzamide, 4-{[2-(3-{(2R)-2-[(2R)-2-(6-Amino-pyridin-3-yl)-2-hydroxy-ethylamino]-propyl}-phenyl)-acetylamino]-methyl}-N-(3-benzylsulfamoyl-benzyl)-benzamide, 4-{[2-(3-{(2R)-2-[(2R)-2-(6-Amino-pyridin-3-yl)-2-hydroxy-ethylamino]-propyl}-phenyl)-acetylamino]-methyl}-N-(3-methylsulfamoyl-benzyl)-benzamide, 4-{[2-(3-{(2R)-2-[(2R)-2-(6-Amino-pyridin-3-yl)-2-hydroxy-ethylamino]-propyl}-phenyl)-acetylamino]-methyl}-N-(3-ethylsulfamoyl-benzyl)-benzamide, 2-(3-{(2R)-2-[(2R)-2-(6-Amino-pyridin-3-yl)-2-hydroxy-ethylamino]-propyl}-phenyl)-N-(4-benzylsulfamoyl-benzyl)-acetamide hydrochloride.

4-{[2-(3-{(2R)-2-[(2R)-2-(6-Amino-pyridin-3-yl)-2-hydroxy-ethylamino]-propyl}-phenyl)-acetylamino]-methyl}-N-[4-(3-benzyl-ureidomethyl)-benzyl]-benzamide 4-{[2-(3-{(2R)-2-[(2R)-2-(6-Amino-pyridin-3-yl)-2-hydroxy-ethylamino]-propyl}-phenyl)-acetylamino]-methyl}-N-{4-[3-(3,4-dimethoxy-benzyl)-ureidomethyl]-benzyl}-benzamide 4-{[2-(3-{(2R)-2-[(2R)-2-(6-Amino-pyridin-3-yl)-2-hydroxy-ethylamino]-propyl}-phenyl)-acetylamino]-methyl}-N-{4-[3-(4-phenoxy-benzyl)-ureidomethyl]-benzyl}-benzamide, and, 4-{[2-(3-{(2R)-2-[(2R)-2-(6-Amino-pyridin-3-yl)-2-hydroxy-ethylamino]-propyl}-phenyl)-acetylamino]-methyl}-N-{4-[3-(4-benzyloxy-benzyl)-ureidomethyl]-benzyl}-benzamide.

According to one aspect of the present invention, the compounds of formula (1) wherein the $CH_2$—C(=O)NH-benzyl-$Q^1$-$Q^2$-$Q^3$-$Q^4$ group is in position meta are generally preferred.

The compounds of formula (1) may also be optionally transformed into pharmaceutically acceptable salts. In particular, these pharmaceutically acceptable salts of the compounds of the formula (1) include the acid addition and the base salts (including disalts) thereof.

Suitable acid addition salts are formed from acids which form non-toxic salts. Examples include the acetate, aspartate, benzoate, besylate, bicarbonate/carbonate, bisulphate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, palmoate, phosphate, saccharate, stearate, succinate sulphate, D- and L-tartrate, 1-hydroxy-2-naphthoate and tosylate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see Stahl and Wermuth, Handbook of Pharmaceutical Salts: Properties, Selection, and Use, Wiley-VCH, Weinheim, Germany (2002).

A pharmaceutically acceptable salt of a compound of formula (1) may be readily prepared by mixing together solutions of the compound of formula (1) and the desired acid or base, as appropriate. The salt may precipitate from solution and be collected by filtration or may be recovered by evaporation of the solvent.

Pharmaceutically acceptable solvates in accordance with the invention include hydrates and solvates wherein the solvent of crystallization may be isotopically substituted, e.g. $D_2O$, $d_6$-acetone, $d_6$-DMSO.

Also within the scope of the invention are clathrates, drug-host inclusion complexes wherein, in contrast to the aforementioned solvates, the drug and host are present in non-stoichiometric amounts. For a review of such complexes, see J Pharm Sci, 64 (8), 1269–1288 by Haleblian (August 1975).

Hereinafter all references to compounds of formula (1) include references to salts thereof and to solvates and clathrates of compounds of formula (1) and salts thereof.

The invention includes all polymorphs of the compounds of formula (1) as hereinbefore defined.

Also within the scope of the invention are so-called "prodrugs" of the compounds of formula (1). Thus certain derivatives of compounds of formula (1) which have little or no pharmacological activity themselves can, when metabolised upon administration into or onto the body, give rise to compounds of formula (1) having the desired activity. Such derivatives are referred to as "prodrugs".

Prodrugs in accordance with the invention can, for example, be produced by replacing appropriate functionalities present in the compounds of formula (1) with certain moieties known to those skilled in the art as "pro-moieties" as described, for example, in "Design of Prodrugs" by H Bundgaard (Elsevier, 1985).

Finally, certain compounds of formula (1) may themselves act as prodrugs of other compounds of formula (1).

The present invention also includes all pharmaceutically acceptable isotopic variations of a compound of formula (1). An isotopic variation is defined as one in which at least one atom is replaced by an atom having the same atomic number, but an atomic mass different from the atomic mass usually found in nature.

Examples of isotopes suitable for inclusion in the compounds of the invention include isotopes of hydrogen, such as $^2H$ and $^3H$, carbon, such as $^{13}C$ and $^{14}C$, nitrogen, such as $^{15}N$, oxygen, such as $^{17}O$ and $^{18}O$, phosphorus, such as $^{32}P$, sulphur, such as $^{35}S$, fluorine, such as $^{18}F$, and chlorine, such as $^{36}Cl$.

Substitution of the compounds of the invention with isotopes such as deuterium, i.e. $^2H$, may afford certain therapeutic advantages resulting from greater metabolic stability, for example, increased in vivo half-life or reduced dosage requirements, and hence may be preferred in some circumstances.

Certain isotopic variations of the compounds of formula (1), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Isotopic variations of the compounds of formula (1) can generally be prepared by conventional techniques known to those skilled in the art or by processes analogous to those described in the accompanying Examples and Preparations using appropriate isotopic variations of suitable reagents.

The compounds of the formula (1) can also be present in stereoisomeric forms. If the compounds of the formula (1) contain one or more centres of asymmetry, these can independently of one another have the (S) configuration or the (R) configuration. The invention includes all possible stereoisomers of the compounds of the formula (1), for example enantiomers and diastereomers, and mixtures of two or more stereoisomeric forms, for example mixtures of enantiomers and/or diastereomers, in all ratios. The invention thus relates to enantiomers in enantiomerically pure form, both as levorotatory and dextrorotatory antipodes, in the form of racemates and in the form of mixtures of the two enantiomers in all ratios. The invention likewise relates to diastereomers in diastereomerically pure form and in the form of mixtures in all ratios. In the presence of cis/trans isomerism, the invention relates to both the cis form and the trans form and mixtures of these forms in all ratios. Individual stereoisomers can be prepared, if desired, by use of stereochemically homogeneous starting substances in the synthesis, by stereoselective synthesis or by separation of a mixture according to customary methods, for example by chromatography, crystallization or by chromatography on chiral phases. If appropriate, derivatization can be carried out before separation of stereoisomers. A stereoisomer mixture can be separated at the stage of the compounds of the formula (1) or at the stage of a starting substance or of an intermediate in the course of the synthesis.

According to one aspect of the present invention, the (R,R)-stereoisomer of the formula below, wherein $Q^1$, $Q^2$, $Q^3$ and $Q^4$ are as defined above, is generally preferred:

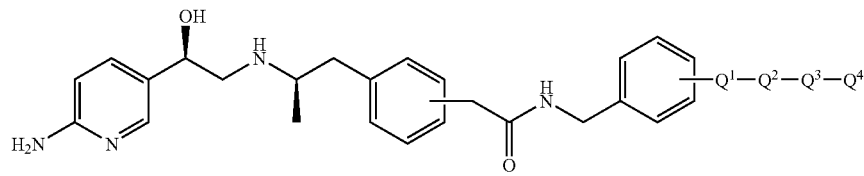

The compounds of the formula (1) according to the invention can moreover contain mobile hydrogen atoms, i.e. be present in various tautomeric forms. The present invention also relates to all tautomers of the compounds of the formula (1).

According to a further aspect, the present invention concerns mixtures of compounds of the formula (1), as well as mixtures with or of their pharmaceutically acceptable salts, solvates, isomeric forms and/or isotope forms.

According to the present invention, all the here above mentioned forms of the compounds of formula (1) except the pharmaceutically acceptable salts (i.e. said solvates, isomeric forms, tautomers and isotope forms), are defined as "derived forms" of the compounds of formula (1) in what follows (including the claims).

The compounds of formula (1), their pharmaceutically acceptable salts and/or derived forms, are valuable pharmaceutically active compounds, which are suitable for the therapy and prophylaxis of numerous disorders in which the β2 receptor is involved or in which agonism of this receptor may induce benefit, in particular the allergic and non-allergic airways diseases but also in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

The compounds of formula (1) and their pharmaceutically acceptable salts and derived forms as mentioned above can be administered according to the invention to animals, preferably to mammals, and in particular to humans, as pharmaceuticals for therapy and/or prophylaxis. They can be administered per se, in mixtures with one another or in the form of pharmaceutical preparations which as active constituent contain an efficacious dose of at least one compounds of formula (1), its pharmaceutically acceptable salts and/or derived forms, in addition to customary pharmaceutically innocuous excipients and/or additives.

The compounds of formula (1), their pharmaceutically acceptable salts and/or derived forms may be freeze-dried, spray-dried, or evaporatively dried to provide a solid plug, powder, or film of crystalline or amorphous material. Microwave or radio frequency drying may be used for this purpose.

The compounds of formula (1), their pharmaceutically acceptable salts and/or derived forms may be administered alone or in combination with other drugs and will generally be administered as a formulation in association with one or more pharmaceutically acceptable excipients. The term "excipient" is used herein to describe any ingredient other than the compound of the invention. The choice of excipient will to a large extent depend on the particular mode of administration.

Oral Administration

The compounds of formula (1), their pharmaceutically acceptable salts and/or derived forms may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agents. Liquid formulations may also be prepared by the reconstitution of a solid, for example, from a sachet.

The compounds of formula (1), their pharmaceutically acceptable salts and/or derived forms may also be used in fast-dissolving, fast-disintegrating dosage forms such as those described in Expert Opinion in Therapeutic Patents, 11 (6), 981–986 by Liang and Chen (2001).

The composition of a typical tablet in accordance with the invention may comprise:

| Ingredient | % w/w |
| --- | --- |
| Compound of formula (1) | 10.00* |
| Microcrystalline cellulose | 64.12 |
| Lactose | 21.38 |
| Croscarmellose sodium | 3.00 |
| Magnesium stearate | 1.50 |

*Quantity adjusted in accordance with drug activity.

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolate and silicates, lubricating agents, for example, magnesium stearate and stearic acid, wetting agents, for example, sodium lauryl sulphate, preservatives, anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25(2), 1–14 (2001). Other modified release formulations are described in U.S. Pat. No. 6,106,864.

Parenteral Administration

The compounds of formula (1), their pharmaceutically acceptable salts and/or derived forms may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (1), their pharmaceutically acceptable salts and/or derived forms used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled dual-, targeted and programmed release.

Topical Administration

The compounds of formula (1), their pharmaceutically acceptable salts and/or derived forms may also be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin and propylene glycol. Penetration enhancers may be incorporated—see, for example, J Pharm Sci, 88 (10), 955–958 by Finnin and Morgan (October 1999).

Other means of topical administration include delivery by iontophoresis, electroporation, phonophoresis, sonophoresis and needle-free or microneedle injection.

Formulations for topical administration may be formulated to be immediate and/or modified release. Modified release formulations include delayed-, sustained-, pulsed-, controlled dual-, targeted and programmed release. Thus compounds of the invention may be formulated in a more solid form for administration as an implanted depot providing long-term release of the active compound.

Inhaled/Intranasal Administration

The compounds of formula (1), their pharmaceutically acceptable salts and/or derived forms can also be administered intranasally or by inhalation, typically in the form of a dry powder (either alone, as a mixture, for example, in a dry blend with lactose in anhydrous or monohydrate form, preferably monohydate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurised container, pump, spray, atomiser (preferably an atomiser using electrohydrodynamics to produce a fine mist), or nebuliser, with or without the use of a suitable propellant, such as dichlorofluoromethane.

The pressurised container, pump, spray, atomizer, or nebuliser contains a solution or suspension of the active compound comprising, for example, ethanol (optionally, aqueous ethanol) or a suitable alternative agent for dispersing, solubilising, or extending release of the active, the propellant(s) as solvent and an optional surfactant, such as sorbitan trioleate or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (1), propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of the compound of the invention, a suitable powder base such as lactose or starch and a performance modifier such as l-leucine, mannitol, or magnesium stearate.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (1). The overall daily dose will typically be in the range 0.001 mg to 40 mg which may be administered in a single dose or, more usually, as divided doses throughout the day.

Formulations for inhaled/intranasal administration may be formulated to be immediate and/or modified release. Modified release formulations include delayed-, sustained-, pulsed-, controlled, dual-, targeted and programmed release.

Flavouring agent such as menthol or levomenthol and/or sweeteners such as saccharin or saccharin sodium can be added to the formulation Rectal/Intravaginal Administration The compounds of formula (1), their pharmaceutically acceptable salts and/or derived forms may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled dual-, targeted and programmed release.

Ocular/Andial Administration

The compounds of formula (1), their pharmaceutically acceptable salts and/or derived forms may also be administered directly to the eye or ear, typically in the form of drops of a micronised suspension or solution in isotonic, pH-adjusted, sterile saline. Other formulations suitable for ocular and andial administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/andial administration may be formulated to be immediate and/or modified release. Modified release formulations include delayed-, sustained-, pulsed-, controlled dual-, targeted, or programmed release.

Enabling Technologies

The compounds of formula (1), their pharmaceutically acceptable salts and/or derived forms may be combined with soluble macromolecular entities such as cyclodextrin or polyethylene glycol-containing polymers to improve their solubility, dissolution rate, taste-masking, bioavailability and/or stability.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Dosage

For administration to human patients, the total daily dose of the compounds of the invention is typically in the range 0.001 mg to 5000 mg depending, of course, on the mode of administration. For example, oral administration may require a total daily dose of from 1 mg to 5000 mg, while an inhaled dose may only require from 0.001 mg to 40 mg. The total daily dose may be administered in single or divided doses.

These dosages are based on an average human subject having a weight of about 65 to 70 kg. The physician will readily be able to determine doses for subjects whose weight falls outside this range, such as infants and the elderly.

According to another embodiment of the present invention, the compounds of the formula (1), or pharmaceutically acceptable salts, derived forms or compositions thereof, can also be used as a combination with one or more additional therapeutic agents to be co-administered to a patient to obtain some particularly desired therapeutic end result such as the treatment of pathophysiologically-relevant disease processes including, but not limited to (i) bronchoconstriction, (ii) inflammation, (iii) allergy, (iv) tissue destruction, (v) signs and symptoms such as breathlessness, cough. The second and more additional therapeutic agents may also be a compound of the formula (1), or a pharmaceutically acceptable salt, derived forms or compositions thereof, or one or more β2 agonists known in the art. More typically, the second and more therapeutic agents will be selected from a different class of therapeutic agents.

As used herein, the terms "co-administration", "co-administered" and "in combination with", referring to the compounds of formula (1) and one or more other therapeutic agents, is intended to mean, and does refer to and include the following:

simultaneous administration of such combination of compound(s) of formula (1) and therapeutic agent(s) to a patient in need of treatment, when such components are formulated together into a single dosage form which releases said components at substantially the same time to said patient, substantially simultaneous administration of such combination of compound(s) of formula (1) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (1) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (1) and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of formula (1), or pharmaceutically acceptable salts, derived forms or compositions thereof, include, but are by no means limited to:

(a) 5-Lipoxygenase (5-LO) inhibitors or 5-lipoxygenase activating protein (FLAP) antagonists, (b) Leukotriene antagonists (LTRAs) including antagonists of $LTB_4$, $LTC_4$, $LTD_4$, and $LTE_4$, (c) Histamine receptor antagonists including H1 and H3 antagonists, (d) α$_1$- and α$_2$-adrenoceptor agonist vasoconstrictor sympathomimetic agents for decongestant use,
(e) muscarinic M3 receptor antagonists or anticholinergic agents,
(f) PDE inhibitors, e.g. PDE3, PDE4 and PDE5 inhibitors,
(g) Theophylline,
(h) Sodium cromoglycate,
(i) COX inhibitors both non-selective and selective COX-1 or COX-2 inhibitors (NSAIDs),
(j) Oral and inhaled glucocorticosteroids,
(k) Monoclonal antibodies active against endogenous inflammatory entities,
(l) Anti-tumor necrosis factor (anti-TNF-α) agents,
(m) Adhesion molecule inhibitors including VLA-4 antagonists,
(n) Kinin-B$_1$- and B$_2$-receptor antagonists,
(o) Immunosuppressive agents,
(p) Inhibitors of matrix metalloproteases (MMPs),
(q) Tachykinin NK$_1$, NK$_2$ and NK$_3$ receptor antagonists,
(r) Elastase inhibitors,
(s) Adenosine A2a receptor agonists,
(t) Inhibitors of urokinase,
(u) Compounds that act on dopamine receptors, e.g. D2 agonists,
(v) Modulators of the NFκβ pathway, e.g. IKK inhibitors,
(w) Agents that can be classed as mucolytics or anti-tussive, and
(x) Antibiotics.

According to the present invention, combination of the compounds of formula (1) with:
  glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, ciclesonide, and mometasone furoate, or
  muscarinic M3 receptor antagonists or anticholinergic agents including in particular ipratropium salts, namely bromide, tiotropium salts, namely bromide, oxitropium salts, namely bromide, perenzepine, and telenzepine,
are preferred.

It is to be appreciated that all references herein to treatment include curative, palliative and prophylactic treatment. The description, which follows, concerns the therapeutic applications to which the compounds of formula (1) may be put.

The compounds of formula (1) have the ability to interact with the β2 receptor and thereby have a wide range of therapeutic applications, as described further below, because of the essential role which the β2 receptor plays in the physiology of all mammals.

Therefore, a further aspect of the present invention relates to the compounds of formula (1), or pharmaceutically acceptable salts, derived forms or compositions thereof, for use in the treatment of diseases, disorders, and conditions in which the β2 receptor is involved. More specifically, the present invention also concerns the compounds of formula (1), or pharmaceutically acceptable salts, derived forms or compositions thereof, for use in the treatment of diseases, disorders, and conditions selected from the group consisting of:
  asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis,
  chronic or acute bronchoconstriction, chronic bronchitis, small airways obstruction, and emphysema,
  obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension,
  bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis,
  bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

A still further aspect of the present invention also relates to the use of the compounds of formula (1), or pharmaceutically acceptable salts, derived forms or compositions thereof, for the manufacture of a drug having a β2 agonist activity. In particular, the present inventions concerns the use of the compounds of formula (1), or pharmaceutically acceptable salts, derived forms or compositions thereof, for the manufacture of a drug for the treatment of β2-mediated diseases and/or conditions, in particular the diseases and/or conditions listed above.

As a consequence, the present invention provides a particularly interesting method of treatment of a mammal, including a human being, including treating said mammal with an effective amount of a compound of formula (1), or a pharmaceutically acceptable salt, derived form or composition thereof. More precisely, the present invention provides a particularly interesting method of treatment of a mammal, including a human being, to treat a β2-mediated diseases and/or conditions, in particular the diseases and/or conditions listed above, including treating said mammal with an effective amount of a compound of formula (1), its pharmaceutically acceptable salts and/or derived forms.

The following examples illustrate the preparation of the compounds of the formula (1):

EXAMPLE 1

4-{[2-(3-{2-[(2R)-2-(6-Amino-pyridin-3-yl)-2-hydroxy-ethylamino]-propyl}-phenyl)-acetylamino]-methyl}-N-(3,4-dimethoxy-benzyl)-benzamide

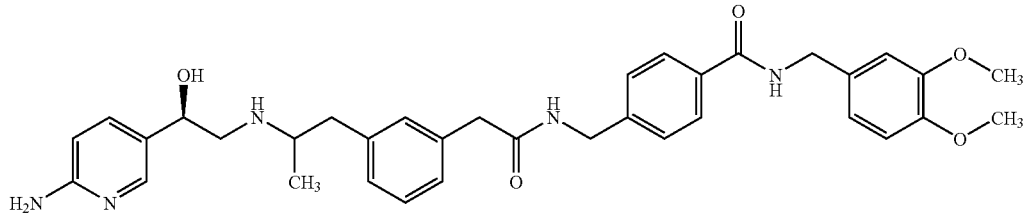

A solution of N-(3,4-dimethoxy-benzyl)-4-({2-[3-(2-{(2R)-2-[6-(2,5-dimethyl-pyrrol-1-yl)-pyridin-3-yl]-2-hydroxy-ethylamino}-propyl)-phenyl]-acetylamino}-methyl)-benzamide (48 mg, 0.07 mmol) in ethanol (1 ml) was treated with hydroxylamine hydrochloride (24 mg, 0.35 mmol) and the resulting mixture heated in a Reactivial™ at 80° C. for 16 hours. The reaction mixture was cooled, passed through a Strong Cation Exchange column eluting with methanol and then 2N ammonia in methanol to elute the product. Further purification by flash column chromatography eluting with dichloromethane:methanol:880 ammonia (97:3:0.5 changing to 90:10:1 by volume) gave the title compound (28 mg) as a pale yellow foam.

$^1$H NMR (400 MHz, CD$_3$OD): δ=7.87–7.63 (3H, m), 7.44–6.78 (10H, m), 6.55–6.42 (1H, m), 4.58–4.50 (1H, m), 4.48 (2H, s), 4.41 (2H, s), 3.80 (6H, s), 3.57–3.36 (2H, m), 3.07–2.43 (5H, m), 1.08–0.88 (3H, m) ppm.

LRMS (electrospray): m/z [M+H]$^+$ 612, [M+Na]$^+$ 634.

EXAMPLE 2

4-{[2-(3-{2-[(2R)-2-(6-Amino-pyridin-3-yl)-2-hydroxy-ethylamino]-propyl}-phenyl)-acetylamino]-methyl}-N-(4-sulfamoyl-benzyl)-benzamide

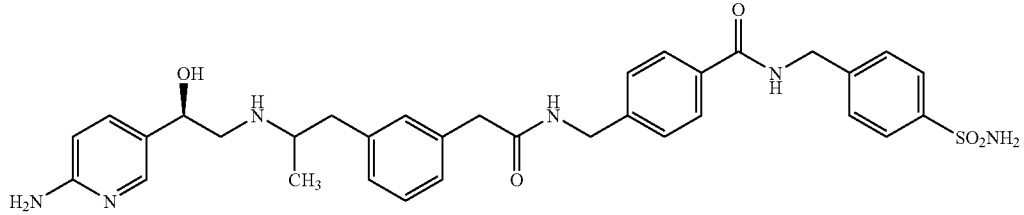

Prepared using the method for example 1 using 4-({2-[3-(2-{(2R)-2-[6-(2,5-dimethyl-pyrrol-1-yl)-pyridin-3-yl]-2-hydroxy-ethylamino}-propyl)-phenyl]-acetylamino}-methyl)-N-(4-sulfamoyl-benzyl)-benzamide (preparation 2) to give the title compound (1:1 mixture of diastereoisomers) as a pale yellow foam.

$^1$H NMR (400 MHz, CD$_3$OD): δ=7.97–7.76 (5H, m), 7.56–7.46 (2H, m), 7.46–7.00 (7H, m), 6.59–6.47 (1H, m), 4.62 (2H, s), 4.59–4.50 (1H, m), 4.42 (2H, s) 3.59–3.51 (2H, m), 2.99–2.55 (5H, m), 1.09–0.97 (3H, m) ppm.

LRMS (electrospray): m/z [M+H]$^+$ 631, [M+Na]$^+$ 653.

EXAMPLE 3

4-{[2-(3-{2-[(2R)-2-(6-Amino-pyridin-3-yl)-2-hydroxy-ethylamino]-propyl}-phenyl)-acetylamino]-methyl}-N-(2-ethoxy-benzyl)-benzamide

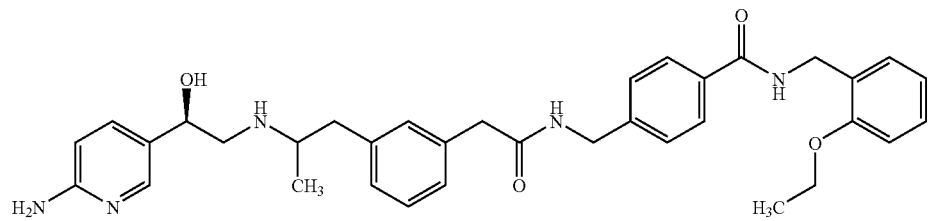

Prepared using the method for example 1 using 4-({2-[3-(2-{(2R)-2-[6-(2,5-dimethyl-pyrrol-1-yl)-pyridin-3-yl]-2-hydroxy-ethylamino}-propyl)-phenyl]-acetylamino}-methyl)-N-(2-ethoxy-benzyl)-benzamide (preparation 3) to give the title compound (1:1 mixture of diastereoisomers) as a pale yellow foam.

$^1$H NMR (400 MHz, CD$_3$OD): δ=7.87–7.72 (3H, m), 7.46–6.82 (11H, m), 6.58–6.46 (1H, m), 4.57 (2H, s), 4.54–4.47 (1H, m), 4.41 (2H, s), 4.08 (2H, q), 3.57–3.49 (2H, m), 2.95–2.51 (5H, m), 1.39 (3H, t), 1.07–0.93 (3H, m) ppm.

LRMS (electrospray): m/z [M+H]$^+$ 596, [M+Na]$^+$ 618.

EXAMPLE 4

4-{[2-(3-{2-[(2R)-2-(6-Amino-pyridin-3-yl)-2-hydroxy-ethylamino]-propyl}-phenyl)-acetylamino]-methyl}-N-[(1R)-1-(4-methoxy-phenyl)-ethyl]-benzamide Prepared using the method for example 1 using 4-({2-[3-(2-{(2R)-2-[6-(2,5-dimethyl-pyrrol-1-yl)-pyridin-3-yl]-2-hydroxy-ethylamino}-propyl)-phenyl]-acetylamino}-methyl)-N-((1R)-1-hydroxymethyl-2-phenyl-ethyl)-benzamide (preparation 5) to give the title compound (1:1 mixture of diastereoisomers) as a pale yellow foam.

$^1$H NMR (400 MHz, CD$_3$OD): δ=7.83–7.76 (1H, m), 7.71–7.61 (2H, m), 7.44–7.33 (1H, m), 7.32–7.00 (11H, m), 4.57–4.52 (1H, m), 4.39 (2H, s), 4.35–4.27 (1H, m), 3.67–3.56 (2H, s), 3.56–3.49 (2H, m), 3.04–2.56 (7H, m), 1.08–0.94 (3H, m), ppm.

LRMS (electrospray): m/z [M+H]$^+$ 612, [M+Na]$^+$ 634.

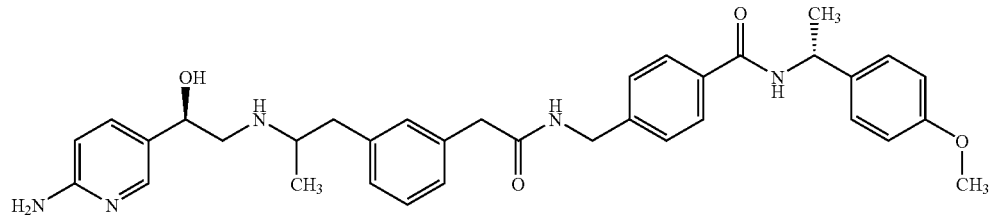

Prepared using the method for example 1 using 4-{[({3-[2-({(2R)-2-[6-(2,5-dimethyl-1H-pyrrol-1-yl)-3-pyridinyl]-2-hydroxyethyl}amino)propyl]phenyl}acetyl)amino]methyl}-N-[(1R)-1-(4-methoxyphenyl)ethyl]benzamide (preparation 4) to give the title compound (1:1 mixture of diastereoisomers) as a pale yellow foam.

$^1$H NMR (400 MHz, CD$_3$OD): δ=7.83–7.71 (3H, m), 7.43–7.00 (9H, m), 6.92–6.83 (2H, m), 6.56–6.46 (1H, m), 5.25–5.12 (1H, m), 4.58–4.46 (1H, m), 4.40 (2H, s), 3.76 (3H, s), 3.56–3.46 (2H, m), 2.96–2.43 (5H, m), 1.54–1.39 (3H, m), 1.08–0.89 (3H, m) ppm.

LRMS (electrospray): m/z [M+H]$^+$ 612, [M+Na]$^+$ 634.

EXAMPLE 5

4-{[2-(3-{2-[(2R)-2-(6-Amino-pyridin-3-yl)-2-hydroxy-ethylamino]-propyl}-phenyl)-acetylamino]-methyl}-N-((1R)-1-hydroxymethyl-2-phenyl-ethyl)-benzamide

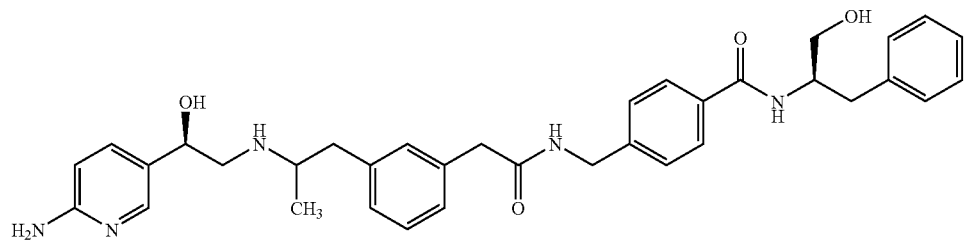

EXAMPLE 6

4-{[2-(3-{2-[(2R)-2-(6-Amino-pyridin-3-yl)-2-hydroxy-ethylamino]-propyl}-phenyl)-acetylamino]-methyl}-N-((1R, 2S)-2-hydroxy-1-methyl-2-phenyl-ethyl)-benzamide

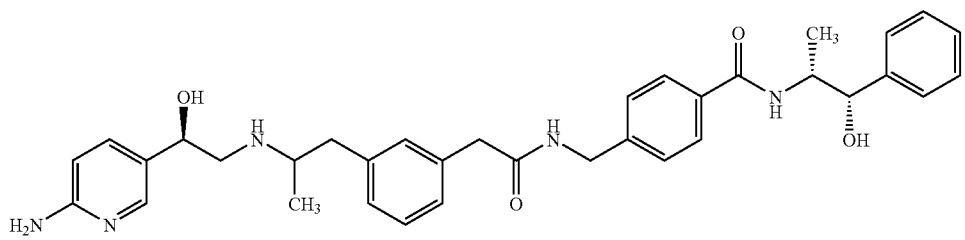

Prepared using the method for example 1 using 4-({2-[3-(2-{(2R)-2-[6-(2,5-dimethyl-pyrrol-1-yl)-pyridin-3-yl]-2-hydroxy-ethylamino}-propyl)-phenyl]-acetylamino}-methyl)-N-((1R,2S)-2-hydroxy-1-methyl-2-phenyl-ethyl)-benzamide (preparation 6) to give the title compound (1:1 mixture of diastereoisomers) as a pale yellow foam.

$^1$H NMR (400 MHz, CD$_3$OD): δ=7.82–7.76 (1H, m), 7.67–7.60 (2H, m), 7.44–7.01 (12H, m), 6.55–6.49 (1H, m), 4.56–4.51 (1H, m), 4.39 (2H, s), 4.36–4.27 (1H, m), 3.57–3.51 (2H, m), 3.36–3.24 (1H, m, partially obscured by solvent) 3.07–2.50 (5H, m), 1.22–1.13 (3H, m), 1.13–0.96 (3H, m) ppm.

LRMS (electrospray): m/z [M+H]$^+$ 612, [M+Na]$^+$ 634.

EXAMPLE 7

4-{[2-(3-{2-[(2R)-2-(6-Amino-pyridin-3-yl)-2-hydroxy-ethylamino]-propyl}-phenyl)-acetylamino]-methyl}-N-((1S, 2R)-2-hydroxy-1-methyl-2-phenyl-ethyl)-benzamide Prepared using the method for example 1 using 4-({2-[3-(2-{(2R)-2-[6-(2,5-dimethyl-pyrrol-1-yl)-pyridin-3-yl]-2-hydroxy-ethylamino}-propyl)-phenyl]-acetylamino}-methyl)-N-((1S,2R)-2-hydroxy-1-methyl-2-phenyl-ethyl)-benzamide (preparation 7) to give the title compound (1:1 mixture of diastereoisomers) as a pale yellow foam.

$^1$H NMR (400 MHz, CD$_3$OD): δ=7.82–7.76 (1H, m), 7.67–7.60 (2H, m), 7.44–7.01 (12H, m), 6.55–6.49 (1H, m), 4.56–4.51 (1H, m), 4.39 (2H, s), 4.36–4.27 (1H, m), 3.57–3.51 (2H, m), 3.36–3.24 (1H, m, partially obscured by solvent) 3.07–2.50 (5H, m), 1.22–1.13 (3H, m), 1.13–0.96 (3H, m) ppm.

LRMS (electrospray): m/z [M+H]$^+$ 612, [M+Na]$^+$ 634.

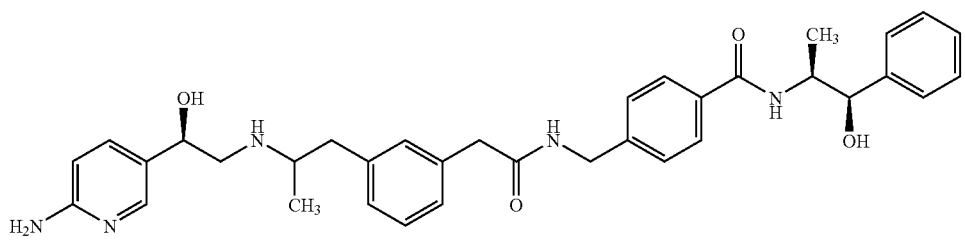

EXAMPLE 8

4-{[2-(3-{2-[(2R)-2-(6-Amino-pyridin-3-yl)-2-hydroxy-ethylamino]-propyl}-phenyl)-acetylamino]-methyl}-N-[2-(3-methoxy-phenyl)-ethyl]-benzamide

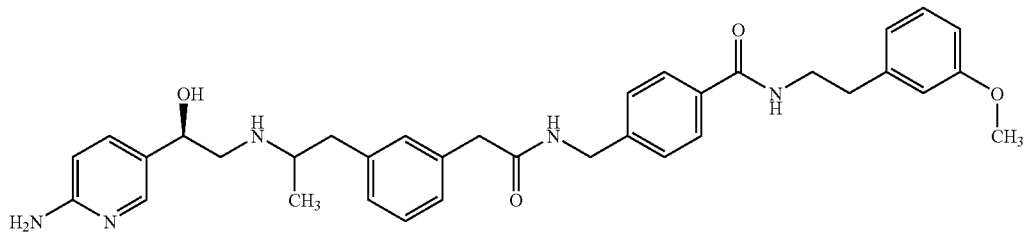

Prepared using the method for example 1 using 4-({2-[3-(2-{(2R)-2-[6-(2,5-dimethyl-pyrrol-1-yl)-pyridin-3-yl]-2-hydroxy-ethylamino}-propyl)-phenyl]-acetylamino}-methyl)-N-[2-(3-methoxy-phenyl)-ethyl]-benzamide (preparation 8) to give the title compound (1:1 mixture of diastereoisomers) as a pale yellow foam.

$^1$H NMR (400 MHz, CD$_3$OD): δ=7.84–7.76 (1H, m), 7.75–7.66 (2H, m), 7.44–7.00 (8H, m), 6.85–6.78 (2H, m), 6.78–6.72 (1H, m), 6.55–6.45 (1H, m), 4.59–4.49 (1H, m), 4.41 (2H, s), 3.74 (3H, s), 3.62–3.52 (4H, m), 3.54–3.22 (2H, m, partially obscured by solvent), 3.00–2.54 (5H, m), 1.08–0.97 (3H, m) ppm.

LRMS (electrospray): m/z [M+H]$^+$ 612, [M+Na]$^+$ 634.

EXAMPLE 9

4-{[2-(3-{(2R)-2-[(2R)-2-(6-Amino-pyridin-3-yl)-2-hydroxy-ethylamino]-propyl}-phenyl)-acetylamino]-methyl}-N-(3,4-dimethoxy-benzyl)-benzamide Prepared using the method for example 1 using N-(3,4-dimethoxy-benzyl)-4-({2-[3-((2R)-2-{(2R)-2-[6-(2,5-dimethyl-pyrrol-1-yl)-pyridin-3-yl]-2hydroxy-ethylamino}-propyl)-phenyl]-acetylamino}-methyl)-benzamide (preparation 9) to give the title compound as a colourless foam.

$^1$H NMR (400 MHz, CD$_3$OD): δ=7.77 (2H, s), 7.75 (1H, s), 7.35 (1H, d), 7.29 (2H, d), 7.18 (1H, d), 7.14 (1H, d), 7.08 (1H, s), 7.02 (1H, d), 6.96 (1H, s), 6.89 (2H, s), 6.49 (1H, d), 4.52 (1H, m), 4.49 (2H, s), 4.41 (2H, s), 3.81 (6H, s), 3.54 (2H, s), 2.91–2.82 (2H, m), 2.67–2.60 (3H, m), 1.07 (3H, d) ppm.

LRMS (APCI): m/z [M+H]$^+$ 612.

Optical Rotation [α]$^D_{25}$=−23.00° c=1, methanol

EXAMPLE 10

4-{[2-(3-{(2R)-2-[(2R)-2-(6-Amino-pyridin-3-yl)-2-hydroxy-ethylamino]-propyl}-phenyl)-acetylamino]-methyl}-N-(2-ethoxy-benzyl)-benzamide

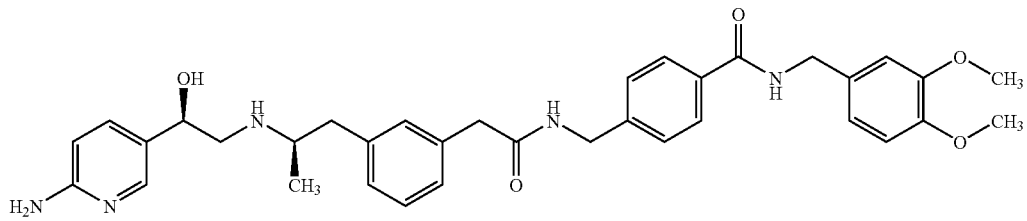

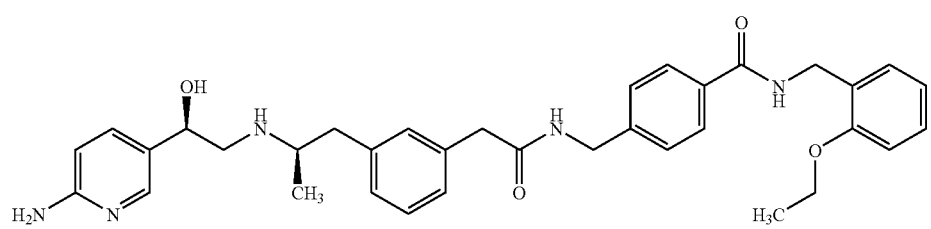

Prepared using the method for example 1 using 4-({2-[3-((2R)-2-{(2R)-[6-(2,5-dimethyl-pyrrol-1-yl)-pyridin-3-yl]-2-hydroxy-ethylamino}-propyl)-phenyl-acetylamino}-methyl)-N-(2-ethoxy-benzyl)-benzamide (preparation 10) to give the title compound as a colourless foam.

$^1$H NMR (400 MHz, CD$_3$OD): δ=7.78 (3H, m), 7.36 (1H, d), 7.32 (2H, d), 7.23–7.18 (3H, m), 7.15 (1H, d), 7.09 (1H, s), 7.03 (1H, d), 6.94 (1H, d), 6.88 (1H, m), 6.50 (1H, d), 4.57 (2H, s), 4.52 (1H, m), 4.42 (2H, s), 4.10 (2H, q), 3.54 (2H, s), 2.93–2.82 (2H, m), 2.71–2.57 (3H, m), 1.42 (3H, t), 1.06 (3H, d) ppm.

LRMS (APCI): m/z [M+H]$^+$ 596.

Optical Rotation [α]$^D_{25}$=–22.80° c=1, methanol

EXAMPLE 11

4-{[2-(3-{(2R)-2-[(2R)-2-(6-Amino-pyridin-3-yl)-2-hydroxy-ethylamino]-propyl}-phenyl)-acetylamino]-methyl}-N-(4-hydroxy-3-methoxy-benzyl)-benzamide

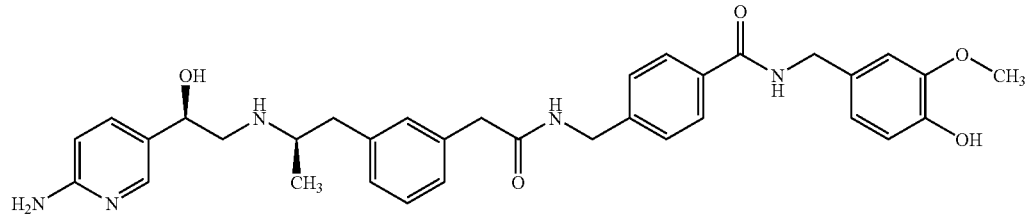

Prepared using the method for example 1 using 4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-N-(4-hydroxy-3-methoxy-benzyl)-benzamide (preparation 11) to give the title compound as a colourless foam.

$^1$H NMR (400 MHz, CD$_3$OD): δ=7.76 (2H, s), 7.74 (1H, s), 7.36 (1H, d), 7.30 (2H, d), 7.19–6.93 (5H, m), 6.75 (2H, m), 6.50 (1H, d), 4.52 (1H, m), 4.46 (2H, s), 4.40 (2H, s), 3.82 (3H, s), 3.53 (2H, s), 2.90–2.81 (2H, m), 2.70–2.59 (3H, m), 1.06 (3H, d) ppm.

LRMS (APCI): m/z [M+H]$^+$ 598.

Optical Rotation [α]$^D_{25}$=–23.0° c=1, methanol

EXAMPLE 12

4-{[2-(3-{(2R)-2-[(2R)-2-(6-Amino-pyridin-3-yl)-2-hydroxy-ethylamino]-propyl}-phenyl)-acetylamino]-methyl}-N-(4-sulfamoyl-benzyl)-benzamide Prepared using the method for example 1 using 4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-N-(4-sulfamoyl-benzyl)-benzamide (preparation 12) to give the title compound as a colourless foam.

$^1$H NMR (400 MHz, CD$_3$OD): δ=7.85 (2H, d), 7.80 (1H, s), 7.77 (2H, m), 7.49 (2H, d), 7.35 (1H, m), 7.32 (2H, d), 7.20 (1H, m), 7.14 (1H, d), 7.09 (1H, s), 7.02 (1H, s), 6.49 (1H, d), 4.61 (2H, s), 4.52 (1H, m), 4.41 (2H, s), 3.53 (2H, s), 2.92–2.82 (2H, m), 2.70–2.56 (3H, m), 1.05 (3H, d) ppm.

LRMS (APCI): m/z [M+H]$^+$ 631.

Optical Rotation [α]$^D_{25}$=–31.0° c=1, methanol

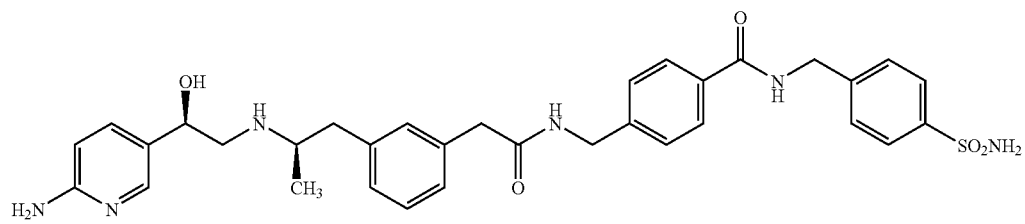

EXAMPLE 13

4-{[2-(3-{(2R)-2-[(2R)-2-(6-Amino-pyridin-3-yl)-2-hydroxy-ethylamino]-propyl}-phenyl)-acetylamino]-methyl}-N-((1R, 2S)-2-hydroxy-1-methyl-2-phenyl-ethyl)-benzamide

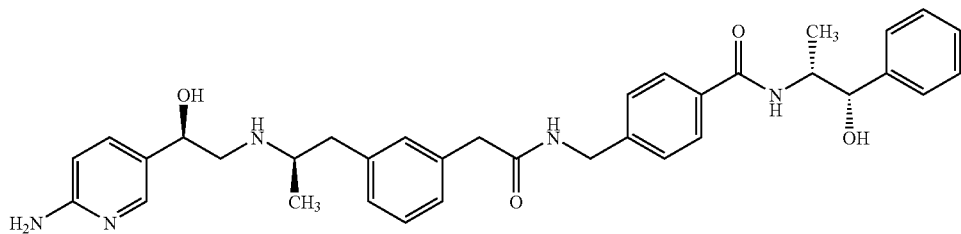

Prepared using the method for example 1 using 4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-N-((1R,2S)-2-hydroxy-1-methyl-2-phenyl-ethyl)-benzamide (preparation 13) to give the title compound as a orange oil.

$^1$H NMR (400 MHz, CD$_3$OD): δ=7.78 (1H, s), 7.63 (2H, d), 7.43 (2H, d), 7.37 (1H, d), 7.32–7.19 (6H, m), 7.15 (1H, d), 7.09 (1H, s), 7.03 (1H, d), 6.51 (1H, d), 4.79 (1H, d), 4.53 (1H, m), 4.39 (2H, s), 4.32 (1H, m), 3.53 (2H, s), 2.94–2.82 (2H, m), 2.71–2.57 (3H, m), 1.19 (3H, d), 1.07 (3H, d) ppm.

LRMS (APCI): m/z [M+H]$^+$ 596.

Optical Rotation [α]$^D_{25}$=−54.41° c=1, methanol

EXAMPLE 14

N-(4-{[2-(3-{(2R)-2-[(2R)-2-(6-Amino-pyridin-3-yl)-2-hydroxy-ethylamino]-propyl}-phenyl)-acetylamino]-methyl}-benzyl)-2,2-diphenyl-acetamide Prepared using the method for example 1 using N-[4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-benzyl]-2,2-diphenyl-acetamide (preparation 14) to give the title compound as a colourless foam.

$^1$H NMR (400 MHz, CD$_3$OD): δ=7.79 (1H, bs), 7.37–7.01 (19H, m), 6.49 (1H, d), 4.99 (1H, s), 4.57–4.53 (1H, m), 4.34 (2H, s), 4.30 (2H, s), 3.50 (2H, s), 2.97–2.82 (2H, m), 2.73–2.55 (3H, m), 1.06 (3H, d) ppm.

LRMS (electrospray): m/z [M+H]$^+$ 642, [M+Na]$^+$ 664.

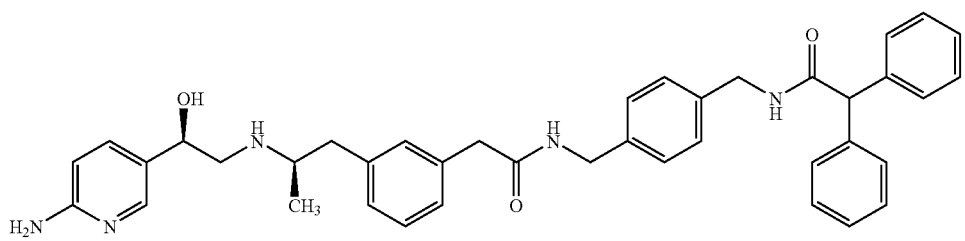

EXAMPLE 15

2-(3-{(2R)-2-[(2R)-2-(6-Amino-pyridin-3-yl)-2-hydroxy-ethylamino]-propyl}-phenyl)-N-{4-[(benzhydryl-amino)-methyl]-benzyl}-acetamide

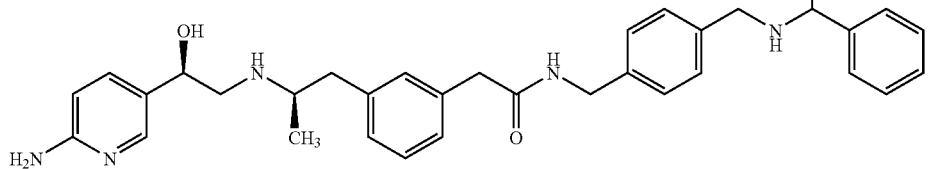

Prepared using the method for example 1 using N-{4-[(benzhydryl-amino)-methyl]-benzyl}-2-[3-((2R)-2-{(2R)-2-[6-(2,5-dimethyl-pyrrol-1-yl)-pyridin-3-yl]-2-hydroxy-ethylamino}-propyl)-phenyl]-acetamide (preparation 15) to give the title compound as a colourless foam.

$^1$H NMR (400 MHz, CD$_3$OD): δ=7.77 (1H, bs), 7.36–7.06 (18H, m), 7.01 (1H, d), 6.48 (1H, d), 4.75 (1H, s), 4.50 (1H, m), 4.34 (2H, s), 3.64 (2H, s), 3.51 (2H, s), 2.90–2.80 (2H, m), 2.69–2.54 (3H, m), 1.04 (3H, d) ppm.

LRMS (electrospray): m/z [M+H]$^+$ 614, [M+Na]$^+$ 636.

EXAMPLE 16

4-{[2-(3{(2R)-2-[(2R)-2-(6-Amino-pyridin-3-yl)-2-hydroxy-ethylamino]-propyl}-phenyl)-acetylamino]-methyl}-N-(2-benzyloxy-ethyl)-benzamide Prepared using the method for example 1 using N-(2-benzyloxy-ethyl)-4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-benzamide (preparation 16) to give the title compound as a colourless foam.

$^1$H NMR (400 MHz, CD$_3$OD): δ=7.79 (1H, s), 7.73 (2H, d), 7.40–7.02 (12H, m), 6.50 (1H, d), 4.59–4.54 (3H, m), 4.41 ((2H, s), 3.65–3.62 (2H, m), 3.57–3.54 (4H, m), 3.02–2.85 (2H, m), 2.75–2.56 (3H, m), 1.07 (3H, d) ppm.

LRMS (electrospray): m/z [M+H]$^+$ 596, [M+Na]$^+$ 618.

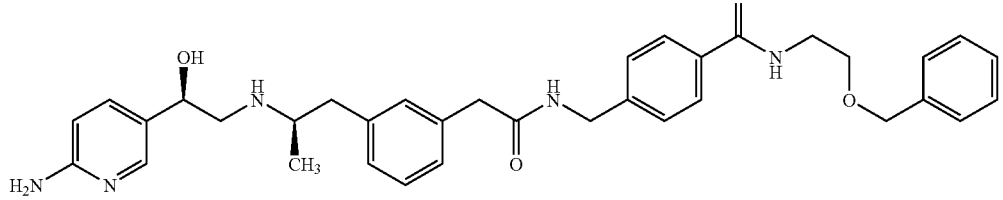

EXAMPLE 17

4-{[2-(3-{(2R)-2-[(2R)-2-(6-Amino-pyridin-3-yl)-2-hydroxy-ethylamino]-propyl}-phenyl)-acetylamino]-methyl}-N-[2-(3-phenyl-propoxy)-ethyl]-benzamide

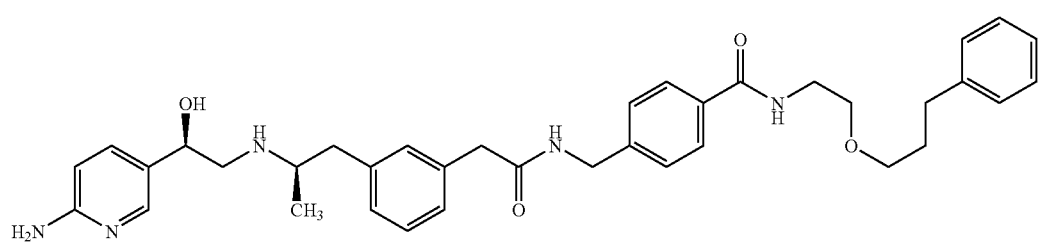

Prepared using the method for example 1 using 4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-N-[2-(3-phenyl-propoxy)-ethyl]-benzamide (preparation 17) to give the title compound as a colourless foam.

¹H NMR (400 MHz, CD₃OD): δ=7.77–7.74 (3H, m), 7.37–7.00 (12H, m), 6.49 (1H, d), 4.53–4.50 (1H, m), 4.40 (2H, s), 3.58–3.53 (6H, m), 3.47–3.44 (2H, m), 2.93–2.81 (2H, m), 2.64–2.55 (5H, m), 1.89–1.81 (2H, m), 1.05 (3H, d) ppm.

EXAMPLE 18

4-{[2-(3-{(2R)-2-[(2R)-2-(6-Amino-pyridin-3-yl)-2-hydroxy-ethylamino]-propyl}-phenyl)-acetylamino]-methyl}-N-[2-(naphthalen-1-ylmethoxy)-ethyl]-benzamide

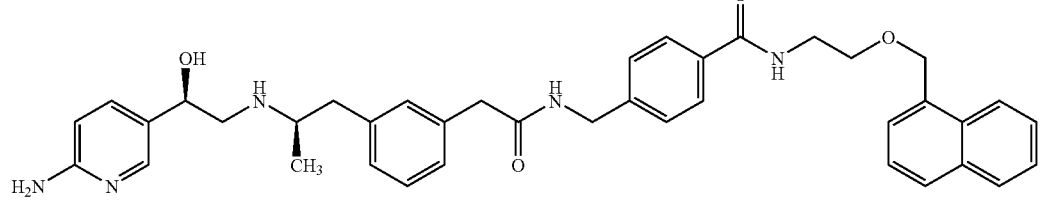

Prepared using the method for example 1 using 4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-N-[2-(naphthalen-1-ylmethoxy)-ethyl]-benzamide (preparation 18) to give the title compound as a colourless foam.

¹H NMR (400 MHz, CD₃OD): δ=8.12 (1H, d), 7.83–7.77 (3H, m), 7.63 (2H, d) 7.50–7.31 (5H, m), 7.27 (2H, d), 7.22–7.12 (2H, m), 7.10 (1H, bs), 7.02 (1H, d), 6.48 (1H, d), 4.99 (2H, s), 4.56–4.51 (1H, m), 4.41 (2H, s), 3.71 (2H, t), 3.57 (2H, t), 3.54 (2H, s) 2.94–2.81 (2H, m), 2.70–2.54 (3H, m), 1.04 (3H, d) ppm.

EXAMPLE 19

4-{[2-(3-{(2R)-2-[(2R)-2-(6-Amino-pyridin-3-yl)-2-hydroxy-ethylamino]-propyl}-phenyl)-acetylamino]-methyl}-N-(3-benzylsulfamoyl-benzyl)-benzamide Prepared using the method for example 1 using N-(4-benzylsulfamoyl-benzyl)-4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-benzamide (preparation 19) to give the title compound as a colourless foam.

¹H NMR (400 MHz, CD₃OD): δ=7.81–7.76 (5H, m), 7.49 (2H, d), 7.36–7.32 (3H, m), 7.22–7.13 (7H, m), 7.09 (1H, s), 7.03 (1H, d), 6.50 (1H, d), 4.61 (2H, s), 4.52 (1H, m), 4.42 (2H, s), 4.03 (2H, s), 3.54 (2H, s), 2.92–2.81 (2H, m), 2.70 (3H, m), 1.06 (3H, d) ppm.

LRMS (APCI): m/z [M+H]⁺ 721.

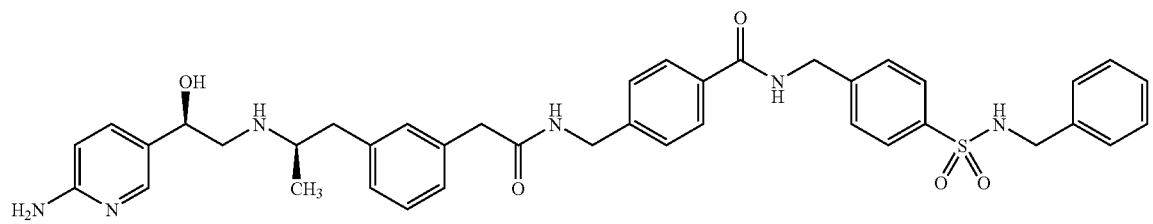

EXAMPLE 20

4-{[2-(3-{(2R)-2-[(2R)-2-(6-Amino-pyridin-3-yl)-2-hydroxy-ethylamino]-propyl}-phenyl)-acetylamino]-methyl}-N-(4-methylsulfamoyl-benzyl)-benzamide

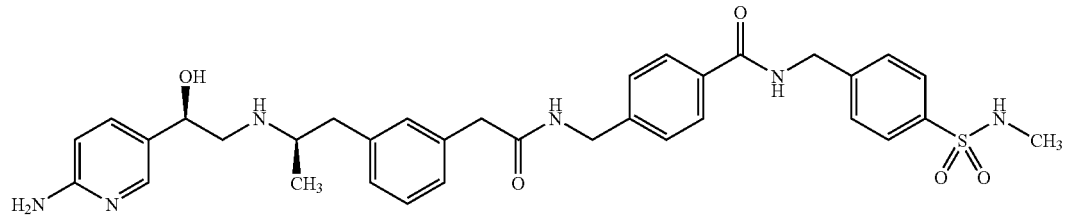

Prepared using the method for example 1 using 4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-N-(4-methylsulfamoyl-benzyl)-benzamide (preparation 20) to give the title compound as a colourless foam.

$^1$H NMR (400 MHz, CD$_3$OD): δ=7.80–7.76 (5H, m), 7.54 (2H, d), 7.37–7.31 (3H, m), 7.22–7.01 (4H, m), 6.50 (1H, d), 4.63 (2H, s), 4.52 (1H, m), 4.41 (2H, s), 3.54 (2H, s), 2.91–2.81 (2H, m0, 2.66–2.59 (3H, m), 2.50 (3H, s), 1.05 (3H, d) ppm.

LRMS (APCI): m/z [M+H]$^+$ 645.

EXAMPLE 21

4-{[2-(3-{(2R)-2-[(2R)-2-(6-Amino-pyridin-3-yl)-2-hydroxy-ethylamino]-propyl}-phenyl)-acetylamino]-methyl}-N-(4-ethylsulfamoyl-benzyl)-benzamide Prepared using the method for example 1 using 4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-N-(4-ethylsulfamoyl-benzyl)-benzamide (preparation 21) to give the title compound as a colourless foam.

$^1$H NMR (400 MHz, CD$_3$OD): δ=7.80–7.76 (5H, m), 7.53 (2H, d), 7.36–7.31 (3H, m), 7.20–7.01 (4H, m), 6.50 (1H, d), 4.63 (2H, s), 4.52 (1H, m), 4.41 (2H, s), 3.54 (2H, s), 2.89–2.81 (4H, m), 2.66–2.59 (3H, m), 1.06–1.02 (6H, m) ppm.

LRMS (APCI): m/z [M+H]$^+$ 659.

EXAMPLE 22

4-{[2-(3-{(2R)-2-[(2R)-2-(6-Amino-pyridin-3-yl)-2-hydroxy-ethylamino]-propyl}-phenyl)-acetylamino]-methyl}-N-(3-benzylsulfamoyl-benzyl)-benzamide

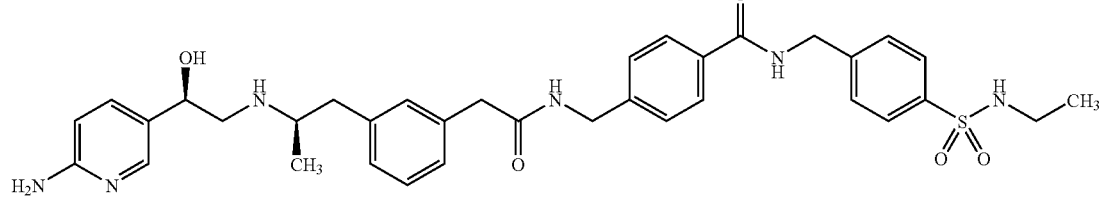

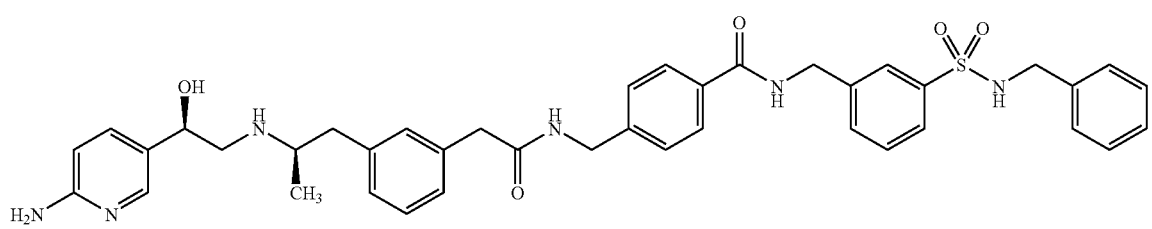

Prepared using the method for example 1 using N-(3-benzylsulfamoyl-benzyl)-4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-benzamide (preparation 22) to give the title compound as a colourless foam.

¹H NMR (400 MHz, CD₃OD): δ=7.82–7.77 (4H, m), 7.72 (1H, d), 7.58 (1H, d), 7.48 (1H, m), 7.36–7.30 (3H, m), 7.21–7.14 (7H, m), 7.09 (1H, s), 7.02 (1H, d), 6.50 (1H, d), 4.59 (2H, s), 4.51 (1H, m), 4.41 (2H, s), 4.02 (2H, s), 3.53 (2H, s), 2.89–2.80 (2H, m), 2.65–2.58 (3H, m), 1.05 (3H, d) ppm.

LRMS (APCI): m/z [M+H]⁺ 721.

Prepared using the method for example 1 using 4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-N-(3-ethylsulfamoyl-benzyl)-benzamide (preparation 24) to give the title compound as a colourless foam.

¹H NMR (400 MHz, CD₃OD): δ=7.83 (1H, s), 7.77 (3H, m), 7.73 (1H, d), 7.59 (1H, d), 7.51 (1H, m), 7.37–7.30 (3H, m), 7.20–7.01 (4H, m), 6.50 (1H, d), 4.62 (2H, s), 4.52 (1H, m), 4.41 (2H, s), 3.53 (2H, s), 2.90–2.81 (4H, m), 2.66–2.55 (3H, m), 1.06–1.00 (6H, m) ppm.

LRMS (APCI): m/z [M+H]⁺ 659, [M+Na]⁺ 681.

EXAMPLE 23

4-{[2-(3-{(2R)-2-[(2R)-2-(6-Amino-pyridin-3-yl)-2-hydroxy-ethylamino]-propyl}-phenyl)-acetylamino]-methyl}-N-(3-methylsulfamoyl-benzyl)-benzamide

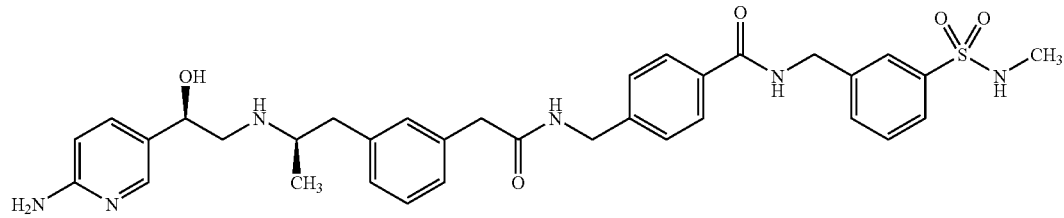

Prepared using the method for example 1 using 4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-N-(3-methylsulfamoyl-benzyl)-benzamide (preparation 23) to give the title compound as a colourless foam.

¹H NMR (400 MHz, CD₃OD): δ=7.82–7.77 (4H, m), 7.73 (1H, d), 7.59 (1H, m), 7.53 (1H, m), 7.37–7.30 (3H, m), 7.22–7.01 (4H, m), 6.50 (1H, d), 4.63 (2H, s), 4.51 (1H, m), 4.41 (2H, s), 3.53 (2H, s), 2.91–2.81 (2H, m), 2.70–2.59 (3H, m), 2.50 (3H, s), 1.06 (3H, d) ppm.

LRMS (APCI): m/z [M+H]⁺ 645.

EXAMPLE 24

4-{[2-(3-{(2R)-2-[(2R)-2-(6-Amino-pyridin-3-yl)-2-hydroxy-ethylamino]-propyl}-phenyl)-acetylamino]-methyl}-N-(3-ethylsulfamoyl-benzyl)-benzamide

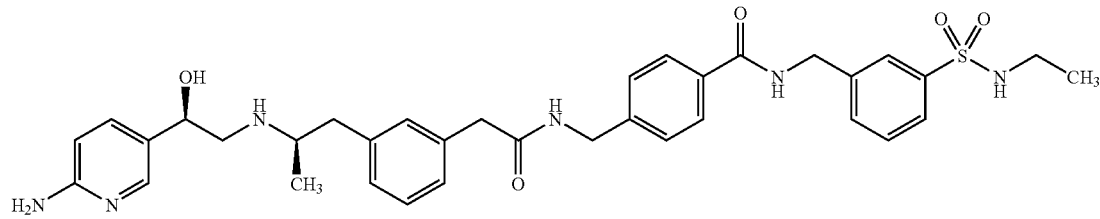

EXAMPLE 25

2-(3-{(2R)-2-[(2R)-2-(6-Amino-pyridin-3-yl)-2-hydroxy-ethylamino]-propyl}-phenyl)-N-(4-benzyl-sulfamoyl-benzyl)-acetamide hydrochloride

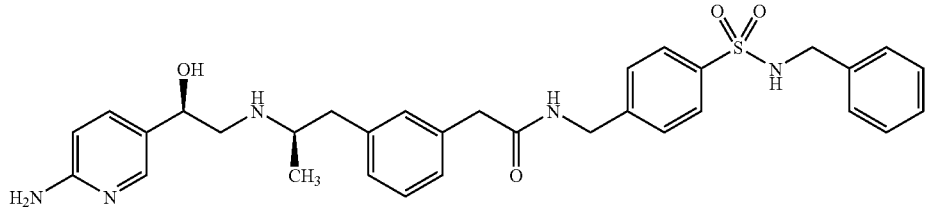

Prepared using the method for example 1 using N-(4-benzylsulfamoyl-benzyl)-2-[3-((2R)-2-{(2R)-2-[6-(2,5-dimethyl-pyrrol-1-yl)-pyridin-3-yl]-2-hydroxy-ethylamino}-propyl)-phenyl]-acetamide (preparation 25) to give the title compound as a colourless foam.

$^1$H NMR (400 MHz, CD$_3$OD): δ=8.02 (1H, d), 7.91 (1H, s), 7.72 (2H, d), 7.38–7.31 (3, m), 7.26–7.17 (8H, m), 7.06 (1H, d), 5.00–4.96 (1H, m), 4.43 (2H, s), 4.01 (2H, s), 3.59–3.49 (3H, m), 3.27–3.19 (3H, m), 2.81–2.74 (1H, m), 1.22 (3H, d) ppm.

LRMS (APCI): m/z [M+H]$^+$ 588, [M+Na]$^+$ 610, [M–H]$^-$ 586.

EXAMPLE 26

2-(3-{(2R)-2-[(2R)-2-(6-Amino-pyridin-3-yl)-2-hydroxy-ethylamino]-propyl}-phenyl)-N-(3-benzyl-sulfamoyl-benzyl)-acetamide hydrochloride

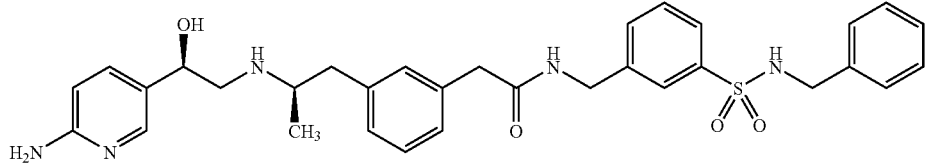

Prepared using the method for example 1 using N-(3-benzylsulfamoyl-benzyl)-2-[3-((2R)-2-{(2R)-2-[6-(2,5-dimethyl-pyrrol-1-yl)-pyridin-3-yl]-2-hydroxy-ethylamino}-propyl)-phenyl]-acetamide (preparation 26) to give the title compound as a colourless foam.

$^1$H NMR (400 MHz, CD$_3$OD): δ=8.02 (1H, d), 7.91 (1H, s), 7.71–7.68 (2H, m), 7.51–7.44 (2H, m), 7.32–7.14 (9H, m), 7.04 (1H; d), 4.99.4.96 (1H, m), 4.44 (2H, s), 3.98 (2H, s), 3.61–3.55 (3H, m), 3.25–3.13 (3H, m), 2.81–2.75 (1H, m), 1.24 (3H, d) ppm.

LRMS (APCI): m/z [M+H]$^+$ 588, [M+Na]$^+$ 610, [M–H]$^-$ 586.

EXAMPLE 27

4-{[2-(4-{2-[(2R)-2-(6-Amino-pyridin-3-yl)-2-hydroxy-ethylamino]-propyl}-phenyl)-acetylamino]-methyl}-N-(3,4-dimethoxy-benzyl)-benzamide

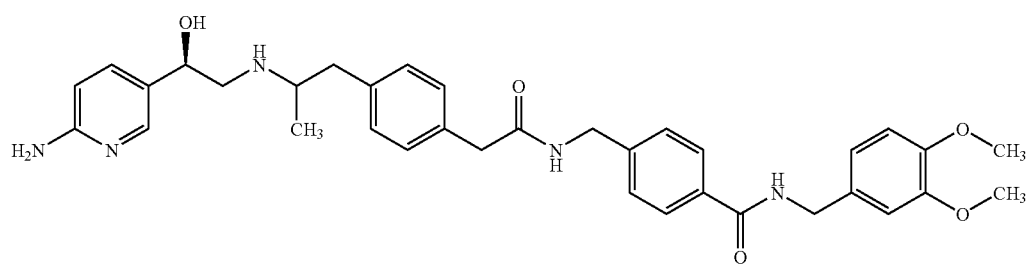

Prepared using the method for example 1 using N-(3,4-dimethoxy-benzyl)-4-({2-[4-(2-{(2R)-2-[6-(2,5-dimethyl-pyrrol-1-yl)-pyridin-3-yl]-2-hydroxy-ethylamino}-propyl)-phenyl]-acetylamino}-methyl)-benzamide (preparation 27) to give the title compound as a colourless foam.

$^1$H NMR (400 MHz, CD$_3$OD): δ=7.77 (3H, m), 7.40–6.89 (10H, m), 6.51 (1H, t), 4.55 (1H, m), 4.48 (2H, s), 4.41 (2H, s), 2.98 (3H, s), 2.52 (3H, s), 3.54 (2H, s), 2.96–2.61 (5H, m), 1.06 (3H, d).

LRMS (APCI): m/z [M+H]$^+$ 612.

EXAMPLE 28

4-{[2-(4-{2-[(2R)-2-(6-Amino-pyridin-3-yl)-2-hydroxy-ethylamino]-propyl}-phenyl)-acetylamino]-methyl}-N-(2-ethoxy-benzyl)-benzamide Prepared using the method for example 1 using 4-({2-[4-(2-{(2R)-2-[6-(2,5-dimethyl-pyrrol-1-yl)-pyridin-3-yl]-2-hydroxy-ethylamino}-propyl)-phenyl]-acetylamino}-methyl)-N-[(1R)-1-(4-methoxy-phenyl)-ethyl]-benzamide (preparation 29) to give the title compound as a colourless foam.

$^1$H NMR (400 MHz, CD$_3$OD): δ=7.79 (1H, m), 7.74 (2H, d), 7.40–7.09 (9H, m), 6.88 (2H, d), 6.51 (1H, t), 5.19 (1H, m), 4.54 (1H, m), 4.40 (2H, s), 3.76 (3H, s), 3.54 (2H, s), 2.93–2.62 (5H, m), 1.52 (3H, d), 1.06 (3H, m) ppm.

LRMS (APCI): m/z [M+H]$^+$ 596.

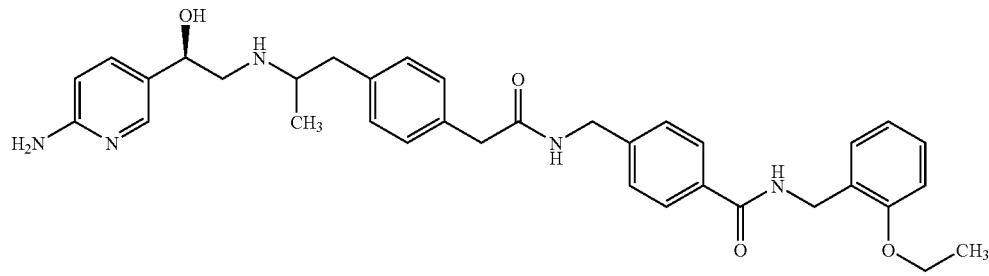

Prepared using the method for example 1 using 4-({2-[4-(2-{(2R)-2-[6-(2,5-dimethyl-pyrrol-1-yl)-pyridin-3-yl]-2-hydroxy-ethylamino}-propyl)-phenyl]-acetylamino}-methyl)-N-(2-ethoxy-benzyl)-benzamide (preparation 28) to give the title compound as a colourless foam.

$^1$H NMR (400 MHz, CD$_3$OD): δ=7.77 (3H, m), 7.40–6.87 (11H, m), 6.51 (1H, t), 4.56 (2H, s), 4.54 (1H, m), 4.41 (2H, s), 4.08 (2H, q), 3.54 (2H, m), 2.92–2.61 (5H, m), 1.40 (3H, t), 1.06 (3H, m) ppm.

LRMS (APCI): m/z [M+H]$^+$ 596.

EXAMPLE 29

4-{[2-(4-{2-[(2R)-2-(6-Amino-pyridin-3-yl)-2-hydroxy-ethylamino]-propyl}-phenyl)-acetylamino]-methyl}-N-[(1R)-1-(4-methoxy-phenyl)-ethyl]-benzamide

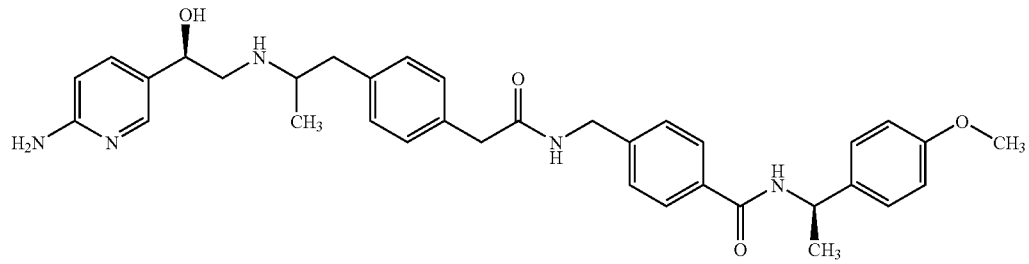

EXAMPLE 30

4-{[2-(4-{2-[(2R)-2-(6-Amino-pyridin-3-yl)-2-hydroxy-ethylamino]-propyl}-phenyl)-acetylamino]-methyl}-N-((1R)-1-benzyl-2-hydroxy-ethyl)-benzamide

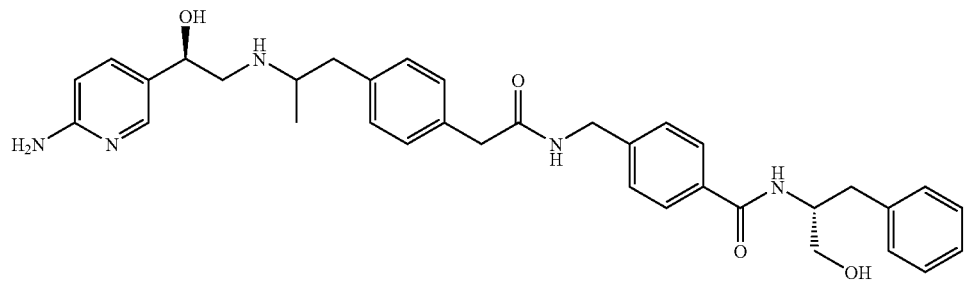

Prepared using the method for example 1 using 4-({2-[4-(2-{(2R)-2-[6-(2,5-dimethyl-pyrrol-1-yl)-pyridin-3-yl]-2-hydroxy-ethylamino}-propyl)-phenyl]-acetylamino}-methyl)-N-((1R)-1-benzyl-2-hydroxy-ethyl)-benzamide (preparation 30) to give the title compound as a colourless foam.

$^1$H NMR (400 MHz, CD$_3$OD): δ=7.78 (1H, d), 7.65 (2H, d), 7.38 (1H, t), 7.27–7.07 (11H, m), 6.51 (1H, t), 4.53 (1H, m), 4.39 (2H, s), 4.33 (1H, m), 3.63 (2H, d), 3.54 (2H, s), 3.04–2.60 (7H, m), 1.06 (3H, m) ppm.

LRMS (APCI): m/z [M+H]$^+$ 596.

EXAMPLE 31

4-{[2-(4-{2-[(2R)-2-(6-Amino-pyridin-3-yl)-2-hydroxy-ethylamino]-propyl}-phenyl)-acetylamino]-methyl}-N-((1R, 2S)-2-hydroxy-1-methyl-2-phenyl-ethyl)-benzamide Prepared using the method for example 1 using 4-({2-[4-(2-{(2R)-2-[6-(2,5-dimethyl-pyrrol-1-yl)-pyridin-3-yl]-2-hydroxy-ethylamino}-propyl)-phenyl]-acetylamino}-methyl)-N-((1R,2S)-2-hydroxy-1-methyl-2-phenyl-ethyl)-benzamide (preparation 31) to give the title compound as a colourless foam.

$^1$H NMR (400 MHz, CD$_3$OD): δ=7.78 (1H, d), 7.63 (2H, d), 7.42–7.07 (12H, m), 6.51 (1H, t), 4.54 (1H, m), 4.39 (2H, s), 4.32 (1H, m), 3.54 (2H, s), 2.95–2.55 (6H, m), 1.18 (3H, d), 1.06 (3H, m) ppm.

LRMS (APCI): m/z [M+H]$^+$ 596.

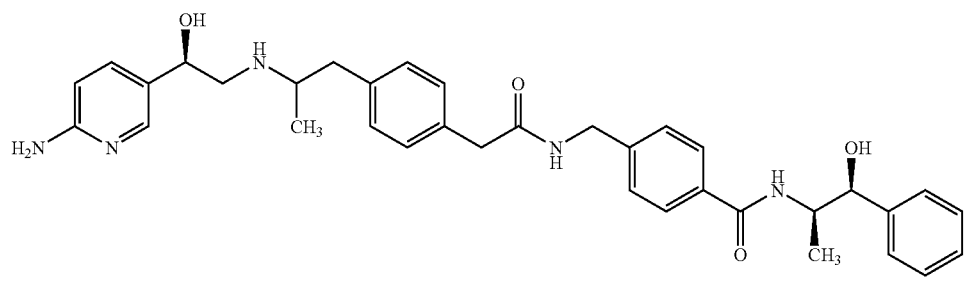

EXAMPLE 32

4-{[2-(4-{2-[(2R)-2-(6-Amino-pyridin-3-yl)-2-hydroxy-ethylamino]-propyl}-phenyl)-acetylamino]-methyl}-N-((1S, 2R)-2-hydroxy-1-methyl-2-phenyl-ethyl)-benzamide

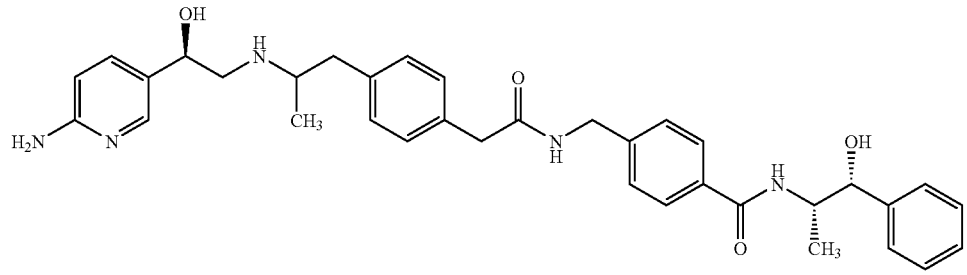

Prepared using the method for example 1 using 4-({2-[4-(2-{(2R)-2-[6-(2,5-dimethyl-pyrrol-1-yl)-pyridin-3-yl]-2-hydroxy-ethylamino}-propyl)-phenyl]-acetylamino}-methyl)-N-((1S,2R)-2-hydroxy-1-methyl-2-phenyl-ethyl)-benzamide (preparation 32) to give the title compound as a colourless foam.

$^1$H NMR (400 MHz, CD$_3$OD): δ=7.79 (1H, d), 7.63 (2H, d), 7.42–7.09 (12H, m), 6.51 (1H, t), 4.54 (1H, m), 4.39 (2H, s), 4.33 (1H, m), 3.54 (2H, s), 2.96–2.55 (6H, m), 1.19 (3H, d), 1.07 (3H, m) ppm.

LRMS (APCI): m/z [M+H]$^+$ 596.

EXAMPLE 33

4-{[2-(4-{2-[(2R)-2-(6-Amino-pyridin-3-yl)-2-hydroxy-ethylamino]-propyl}-phenyl)-acetylamino]-methyl}-N-[2-(3-methoxy-phenyl)-ethyl]-benzamide Prepared using the method for example 1 using 4-({2-[4-(2-{(2R)-2-[6-(2,5-dimethyl-pyrrol-1-yl)-pyridin-3-yl]-2-hydroxy-ethylamino}-propyl)-phenyl]-acetylamino}-methyl)-N-[2-(3-methoxy-phenyl)-ethyl]-benzamide (preparation 33) to give the title compound as a colourless foam.

$^1$H NMR (400 MHz, CD$_3$OD): δ=7.80 (1H, d), 7.69 (2H, d), 7.41–7.07 (8H, m), 6.81 (2H, d), 6.76 (1H, d), 6.51 (1H, t), 4.51 (1H, m), 4.40 (2H, s), 3.74 (3H, s), 3.62–3.52 (4H, m), 2.90–2.65 (7H, m), 1.07 (3H, m) ppm.

LRMS (APCI): m/z [M+H]$^+$ 596.

The following Preparations describe the preparation of certain intermediates used in the preceding Examples.

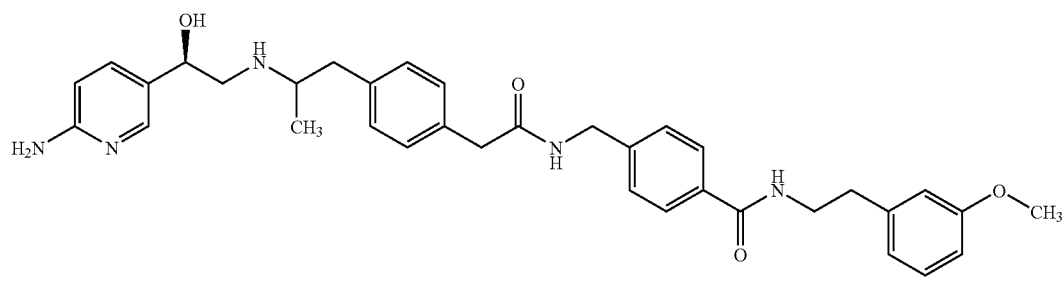

Preparation 1

N-(3,4-Dimethoxy-benzyl)-4-({2-[3-(2-{(2R)-2-[6-(2,5-dimethyl-pyrrol-1-yl)-pyridin-3-yl]-2-hydroxy-ethylamino}-propyl)-phenyl]-acetylamino}-methyl)-benzamide

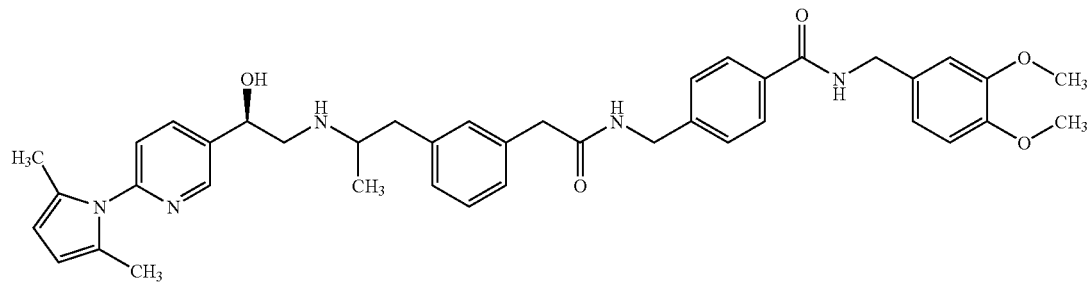

A solution of the acid from preparation 34 (105 mg, 0.19 mmol), 1-hydroxybenzotriazole hydrate (41 mg, 0.3 mmol), 1-(3-dimethylaminopropyl)-3-ethylcarbodiimide hydrochloride (50 mg, 0.26 mmol), triethylamine (80 μl, 0.58 mmol) and 3,4-dimethoxybenzylamine (37 μl, 0.24 mmol) in N,N-dimethylformamide (1 ml) was left to stir at room temperature for 40 hours. The solvent was removed in vacuo and the residue partitioned between water (2 ml) and dichloromethane (2 ml). The organic phase was separated and reduced in vacuo. Purification by flash column chromatography eluting with dichloromethane:methanol:880 ammonia (98:2 changing to 95:5:0.5 by volume) gave 48 mg of N-(3,4-dimethoxybenzyl)-4-{[({3-[2-({(2R)-2-[6-(2,5-dimethyl-1H-pyrrol-1-yl)-3-pyridinyl]-2-hydroxyethyl}-amino)-propyl]-phenyl}-acetyl)-amino]-methyl}-benzamide (1:1 mixture of diastereoisomers) as a pale yellow foam.

$^1$H NMR (400 MHz, CD$_3$OD): δ=8.58–8.45 (1H, m), 8.01–7.90 (1H, m), 7.83–7.72 (2H, m), 7.42–7.06 (7H, m), 6.96 (1H, s), 6.89 (2H, s), 5.81 (2H, s), 4.79–4.70 (1H, m, partially obscured by solvent), 4.48 (2H, s), 4.40 (2H, s), 3.79 (6H, s), 3.54 (2H, s), 3.07–2.51 (5H, m), 2.02 (6H, s), 1.09–0.95 (3H, m) ppm.

LRMS (electrospray): m/z [M−H]$^-$ 688.

Preparation 2

4-({2-[3-(2-{(2R)-2-[6-(2,5-Dimethyl-pyrrol-1-yl)-pyridin-3-yl]-2-hydroxy-ethylamino}-propyl)-phenyl]-acetylamino}-methyl)-N-(4-sulfamoyl-benzyl)-benzamide

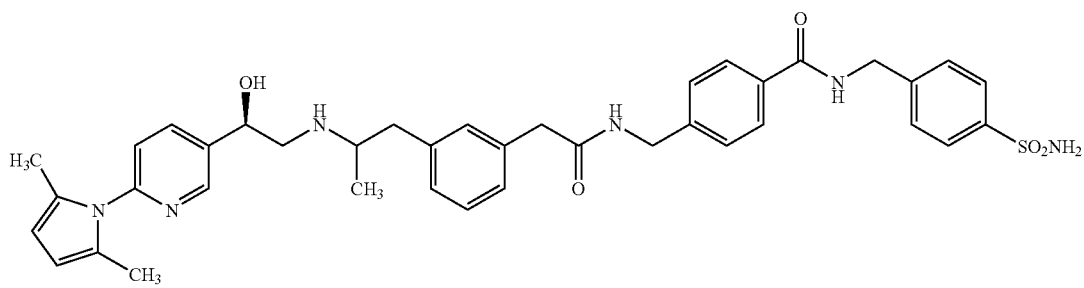

Prepared using the method for 1 using the acid from preparation 34 and the appropriate amine to give the title compound (1:1 mixture of diastereoisomers) as a pale yellow foam.

$^1$H NMR (400 MHz, CD$_3$OD): δ=8.56–8.45 (1H, m), 7.98–7.74 (5H, m), 7.56–7.46 (2H, m), 7.36–7.05 (7H, m), 5.81 (2H, s), 4.87–4.77 (1H, m, partially obscured by solvent), 4.61 (2H, s), 4.42 (2H, s), 3.56 (2H, s), 3.05–2.55 (5H, m), 2.02 (6H, s), 1.12–1.01 (3H, m) ppm.

LRMS (electrospray): m/z [M−H]$^-$ 707.

Preparation 3

4-({2-[3-(2-{(2R)-2-[6-(2,5-Dimethyl-pyrrol-1-yl)-pyridin-3-yl]-2-hydroxy-ethylamino}-propyl)-phenyl]-acetylamino}-methyl)-N-(2-ethoxy-benzyl)-benzamide

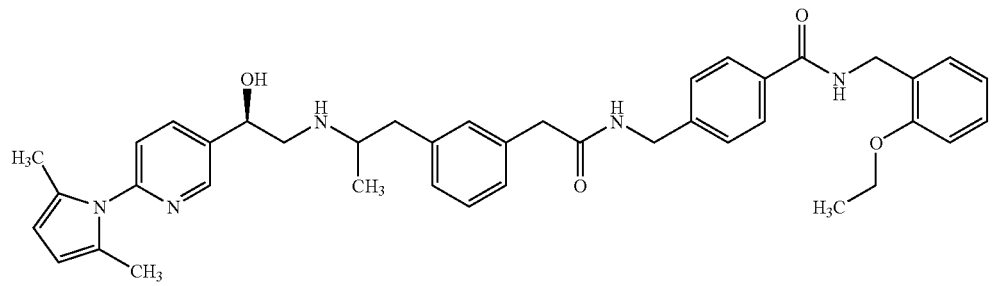

Prepared using the method for preparation 1 using the acid from preparation 34 and the appropriate amine to give the title compound (1:1 mixture of diastereoisomers) as a pale yellow foam.

$^1$H NMR (400 MHz, CD$_3$OD): δ=8.57–8.46 (1H, m), 7.99–7.90 (1H, m), 7.84–7.73 (2H, m), 7.44–7.06 (9H, m), 6.97–6.84 (2H, m), 5.81 (2H, s), 4.79–4.72 (1H, m, partially obscured by solvent), 4.56 (2H, s), 4.41 (2H, s), 4.08 (2H, q), 3.55 (2H, s), 3.07–2.54 (5H, m), 2.02 (6H, s), 1.40 (3H, t), 1.09–0.91 (3H, m) ppm LRMS (electrospray): m/z [M+H]$^+$ 674, [M+Na]$^+$ 696.

Preparation 4

4-({2-[3-(2-{(2R)-2-[6-(2,5-Dimethyl-pyrrol-1-yl)-pyridin-3-yl]-2-hydroxy-ethylamino}-propyl)-phenyl]-acetylamino}-methyl)-N-[(1R)-1-(4-methoxy-phenyl)-ethyl]-benzamide Prepared using the method for preparation 1 using the acid from preparation 34 and the appropriate amine to give the title compound (1:1 mixture of diastereoisomers) as a pale yellow foam.

$^1$H NMR (400 MHz, CD$_3$OD): δ=8.52–8.45 (1H, m), 7.97–7.89 (1H, m), 7.80–7.70 (2H, m), 7.41–7.07 (9H, m), 6.91–6.82 (2H, m), 5.81 (2H, s), 5.23–5.13 (1H, m), 4.81–4.74 (1H, m, partially obscured by solvent), 4.40 (2H, s), 3.76 (3H, s), 3.54 (2H, s), 3.07–2.54 (5H, m), 2.02 (6H, s), 1.56–1.46 (3H, m), 1.10–0.97 (3H, m) ppm.

LRMS (electrospray): m/z [M+H]$^+$ 674, [M+Na]$^+$ 696.

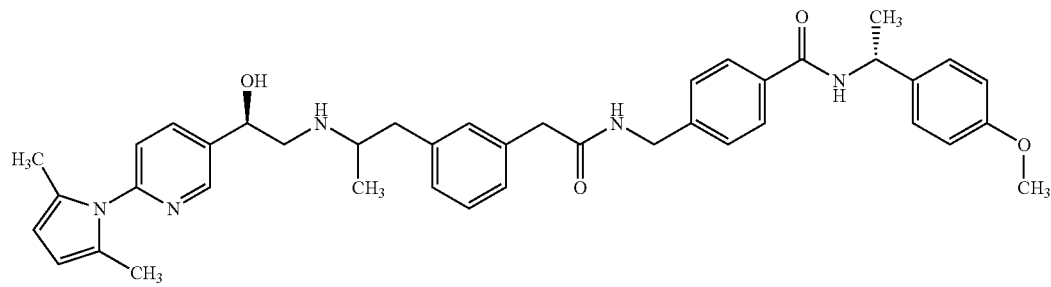

Preparation 5

4-({2-[3-(2-{(2R)-2-[6-(2,5-Dimethyl-pyrrol-1-yl)]-2-hydroxy-ethylamino}-propyl)-phenyl]-acetylamino}-methyl)-N-((1R)-1-hydroxymethyl-2-phenyl-ethyl)-benzamide

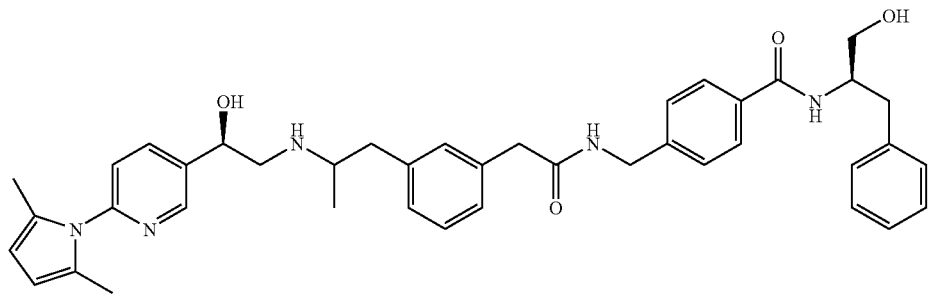

Prepared using the method for preparation 1 using the acid from preparation 34 and the appropriate amine to give the title compound (1:1 mixture of diastereoisomers) as a pale yellow foam.

$^1$H NMR (400 MHz, CD$_3$OD): δ=8.57–8.44 (1H, m), 7.98–7.88 (1H, m), 7.70–7.61 (2H, m), 7.40–7.06 (12H, m), 5.81 (2H, s), 4.90–4.74 (1H, m, partially obscured by solvent), 4.39 (2H, s), 4.36–4.26 (1H, m), 3.62 (2H, d), 3.54 (2H, s), 3.30 (2H, m, obscured by solvent) 3.07–2.55 (5H, m), 2.02 (6H, s), 1.11–0.99 (3H, m) ppm.

LRMS (electrospray): m/z [M+H]$^+$ 674, [M+Na]$^+$ 696.

Preparation 6

4-({2-[3-(2-{(2R)-2-[6-(2,5-Dimethyl-pyrrol-1-yl)-pyridin-3-yl]-2-hydroxy-ethylamino}-propyl)-phenyl]-acetylamino}-methyl)-N-((1R, 2S)-2-hydroxy-1-methyl-2-phenyl-ethyl)-benzamide Prepared using the method for preparation 1 using the acid from preparation 34 and the appropriate amine to give the title compound (1:1 mixture of diastereoisomers) as a pale yellow foam.

$^1$H NMR (400 MHz, CD$_3$OD): δ=8.55–8.46 (1H, m), 7.98–7.87 (1H, m), 7.68–7.58 (2H, m), 7.46–7.37 (2H, m), 7.37–7.07 (10H, m), 5.81 (2H, s), 4.85–4.70 (1H, m, obscured by solvent), 4.39 (2H, s), 4.36–4.27 (1H, m), 3.55 (2H, s), 3.35–3.30 (1H, m, obscured by solvent), 3.07–2.54 (5H, m), 2.02 (6H, s), 1.21–1.10 (3H, m), 1.10–0.90 (3H, m) ppm.

LRMS (electrospray): m/z [M+H]$^+$ 674, [M+Na]$^+$ 696.

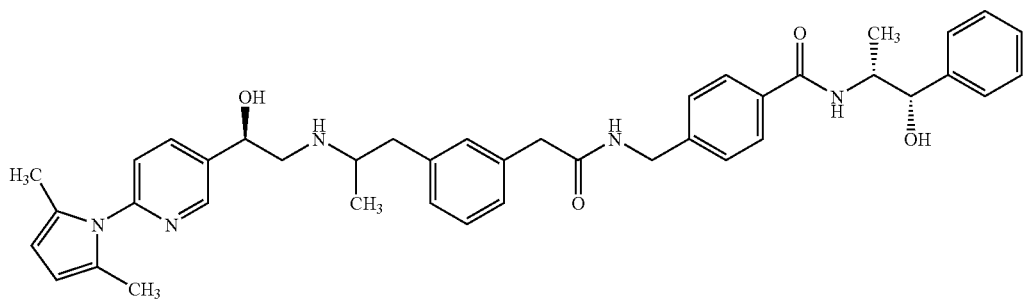

Preparation 7

4-({2-[3-(2-{(2R)-2-[6-(2,5-Dimethyl-pyrrol-1-yl)-pyridin-3yl]-2-hydroxy-ethylamino}-propyl)-phenyl]-acetylamino}-methyl)-N-((1S, 2R)-2-hydroxy-1-methyl-2-phenyl-ethyl)-benzamide

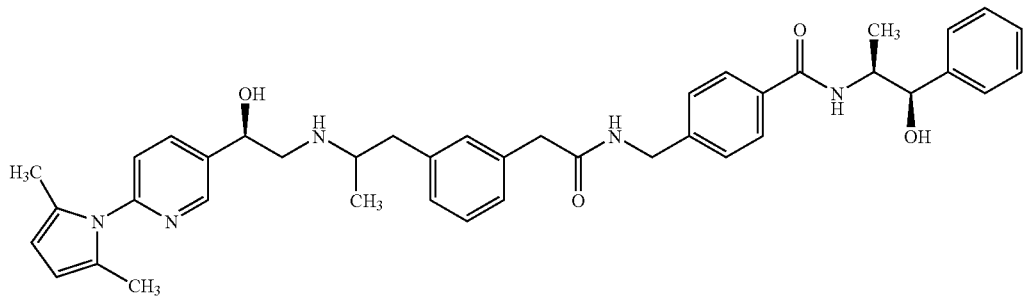

Prepared using the method for preparation 1 using the acid from preparation 34 and the appropriate amine to give the title compound (1:1 mixture of diastereoisomers) as a pale yellow foam.

$^1$H NMR (400 MHz, CD$_3$OD): δ=8.55–8.46 (1H, m), 7.98–7.87 (1H, m), 7.68–7.58 (2H, m), 7.46–7.37 (2H, m), 7.37–7.07 (10H, m), 5.81 (2H, s), 4.85–4.70 (1H, m, obscured by solvent), 4.39 (2H, s), 4.36–4.27 (1H, m), 3.55 (2H, s), 3.35–3.30 (1H, m, obscured by solvent), 3.07–2.54 (5H, m), 2.02 (6H, s), 1.21–1.10 (3H, m), 1.10–0.90 (3H, m) ppm.

LRMS (electrospray): m/z [M+H]$^+$ 674, [M+Na]$^+$ 696.

Prepared using the method for preparation 1 using the acid from preparation 34 and the appropriate amine to give the title compound (1:1 mixture of diastereoisomers) as a pale yellow foam.

$^1$H NMR (400 MHz, CD$_3$OD): δ=8.57–8.46 (1H, m), 7.98–7.89 (1H, m), 7.76–7.64 (2H, m), 7.41–7.08 (8H, m), 6.86–6.76 (2H, m), 6.76–6.70 (1H, m), 5.81 (2H, s), 4.88–4.79 (1H, m, obscured by solvent), 4.40 (2H, s), 3.74 (3H, s), 3.60–3.49 (4H, m), 3.34–3.22 (2H, m, obscured by solvent), 3.07–2.55 (5H, m), 2.02 (6H, s), 1.10–0.98 (3H, m) ppm.

LRMS (electrospray): m/z [M+H]$^+$ 674, [M+Na]$^+$ 696.

Preparation 8

4-({2-[3-(2-{(2R)-2-[6-(2,5-Dimethyl-pyrrol-1-yl)-pyridin-3yl]-2-hydroxy-ethylamino}-propyl)-phenyl]-acetylamino}-methyl)-N-[2-(3-methoxy-phenyl)-ethyl]-benzamide

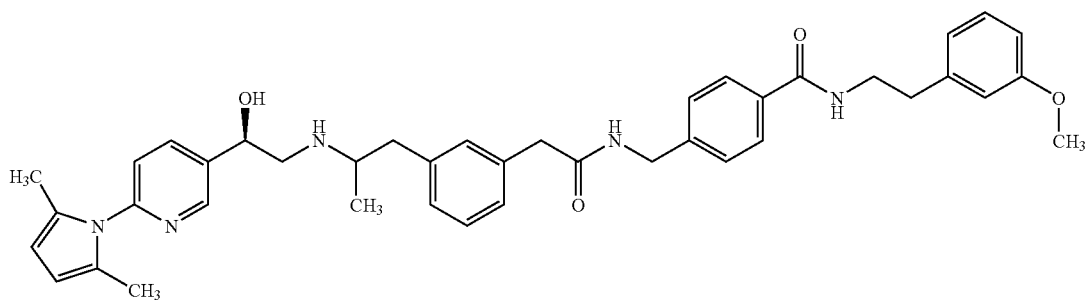

Preparation 9

N-(3,4-Dimethoxy-benzyl)-4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-benzamide

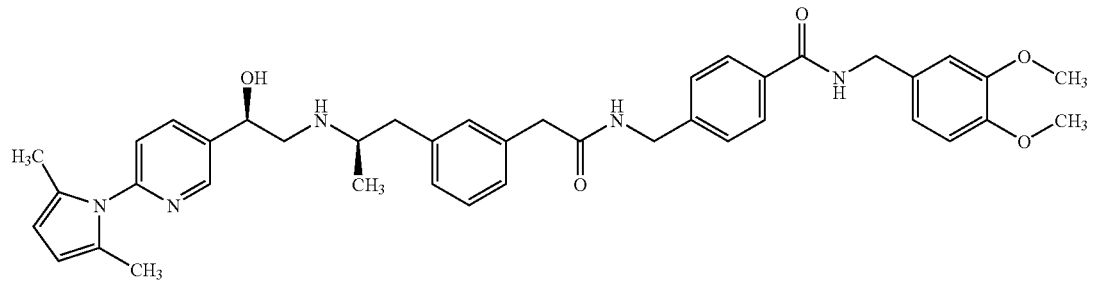

Prepared using the method for preparation 1 using the acid from preparation 38 and the appropriate amine to give the title compound as a colourless foam.

$^1$H NMR (400 MHz, CD$_3$OD): δ=8.50 (1H, s), 7.94 (1H, d), 7.76 (2H, d), 7.31–7.09 (7H, m), 6.97 (1H, s), 6.89 (2H, s), 5.81 (2H, s), 4.81 (1H, m, partially obscured by solvent), 4.48 (2H, s), 4.40 (2H, s), 3.79 (6H, s), 3.54 (2H, s), 2.99 (1H, m), 2.86 (2H, m), 2.75 (1H, m), 2.62 (1H, m), 2.02 (6H, s), 1.06 (3H, d) ppm.

LRMS (APCI): m/z [M+H]$^+$ 690.

Optical Rotation [α]$^D_{25}$=−24.80° c=1, methanol

Preparation 10

4-({2-[3-((2R)-2-{(2R)-[6-(2,5-Dimethyl-pyrrol-1-yl)-pyridin-3-yl]-2-hydroxy-ethylamino}-propyl)-phenyl]-acetylamino}-methyl)-N-(2-ethoxy-benzyl)-benzamide Prepared using the method for preparation 1 using the acid from preparation 38 and the appropriate amine to give the title compound as a colourless foam.

$^1$H NMR (400 MHz, CD$_3$OD): δ=8.50 (1H, s), 7.92 (1H, d), 7.76 (2H, d), 7.32–7.09 (9H, m), 6.94 (1H, d), 6.87 (1H, t), 5.81 (2H, s), 4.81 (1H, m, partially obscured by solvent), 4.57 (2H, s), 4.41 (2H, s), 4.08 (2H, q), 3.55 (2H, s), 2.99 (1H, m), 2.85 (2H, m), 2.75 (1H, m), 2.62 (1H, m), 2.02 (6H, s), 1.40 (3H, t), 1.06 (3H, d) ppm.

LRMS (APCI): m/z [M+H]$^+$ 674.

Optical Rotation [α]$^D_{25}$=−28.01° c=1, MeOH

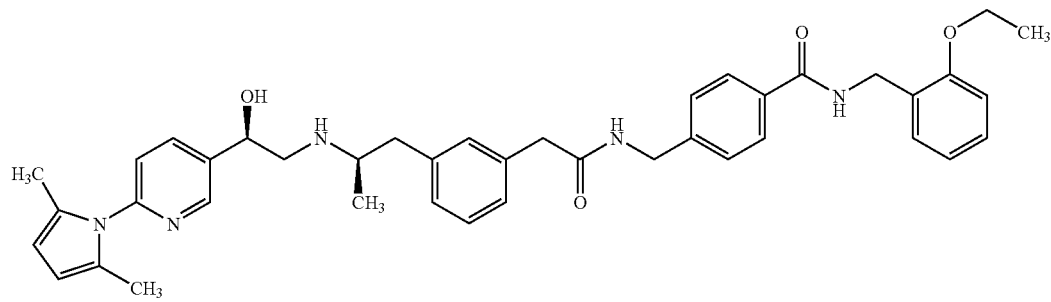

Preparation 11

4-({2-[3-((2R)-2-{(2R)-2-[6-(2,5-Dimethyl-pyrrol-1-yl)-pyridin-3-yl]-2-hydroxy-ethylamino}-propyl)-phenyl]-acetylamino}-methyl)-N-(4-hydroxy-3-methoxy-benzyl)-benzamide

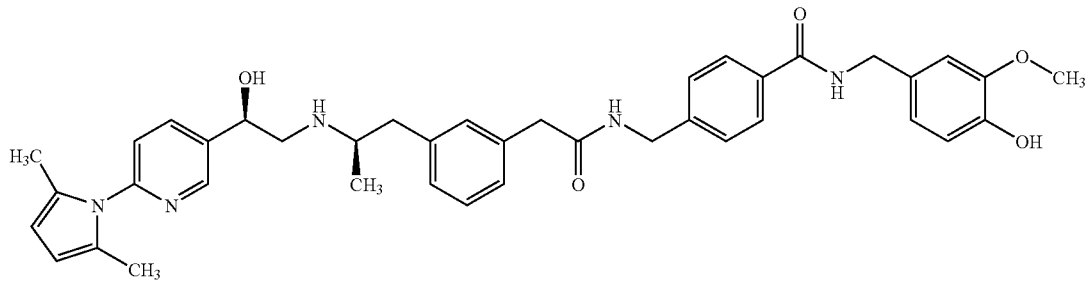

Prepared using the method for preparation 1 using the acid from preparation 38 and the appropriate amine to give the title compound as a colourless foam.

$^1$H NMR (400 MHz, CD$_3$OD): δ=8.51 (1H, s), 7.92 (1H, d), 7.76 (2H, d), 7.31–7.11 (7H, m), 7.17 (1H, s), 6.75 (2H, m), 5.82 (2H, s), 4.82 (1H, m, partially obscured by solvent), 4.45 (2H, s), 4.40 (2H, s), 3.82 (3H, s), 3.55 (2H, s), 2.99 (1H, m), 2.86 (2H, m), 2.79 (1H, m), 2.62 (1H, m), 2.01 (6H, s), 1.06 (3H, d) ppm.

LRMS (APCI): m/z [M+H]$^+$ 676.

Optical Rotation [α]$^D_{25}$=−23.60° c=1, methanol

Preparation 12

4-({2-[3-((2R)-2-{(2R)-2-[6-(2,5-Dimethyl-pyrrol-1-yl)-pyridin-3-yl]-2-hydroxy-ethylamino}-propyl)-phenyl]-acetylamino}-methyl)-N-(4-sulfamoyl-benzyl)-benzamide

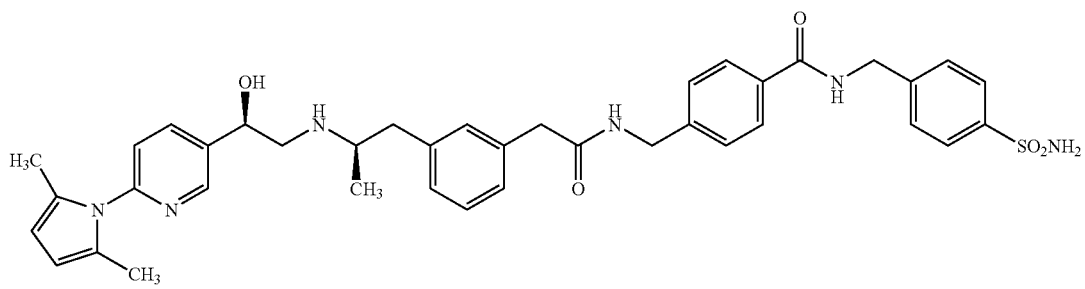

Prepared using the method for preparation 1 using the acid from preparation 38 and the appropriate amine to give the title compound as a colourless foam.

$^1$H NMR (400 MHz, CD$_3$OD): δ=8.50 (1H, s), 7.93 (1H, d), 7.85 (2H, d), 7.78 (2H, d), 7.49 (2H, d), 7.33–7.11 (7H, m), 5.81 (2H, s), 4.80 (1H, bs, partially obscured by solvent), 4.61 (2H, s), 4.41 (2H, s), 3.55 (2H, s), 2.98 (1H, m), 2.87 (2H, m), 2.76 (1H, m), 2.60 (1H, m), 2.02 (6H, s), 1.07 (3H, d) ppm.

LRMS (APCI): m/z [M+H]$^+$ 709.

Optical Rotation [α]$^D_{25}$=−20.4° c=1, methanol

Preparation 13

4-({2-[3-((2R)-2-{(2R)-2-[6-(2,5-Dimethyl-pyrrol-1-yl)-pyridin-3-yl]-2-hydroxy-ethylamino}-propyl)-phenyl]-acetylamino}-methyl)-N-((1R, 2S)-2-hydroxy-1-methyl-2-phenyl-ethyl)-benzamide

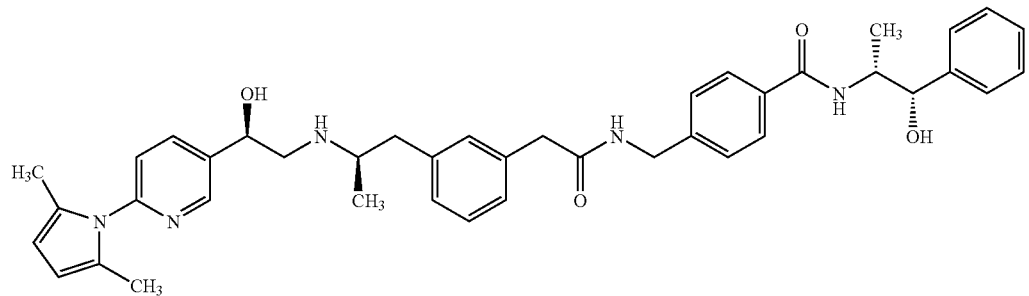

Prepared using the method for preparation 1 using the acid from preparation 38 and the appropriate amine to give the title compound as a colourless foam.

¹H NMR (400 MHz, CD₃OD): δ=8.50 (1H, s), 7.93 (1H, d), 7.62 (2H, d), 7.41 (2H, d), 7.31–7.09 (10H, m), 5.81 (2H, s), 4.53 (1H, bs), 4.39 (2H, s), 3.55 (2H, s), 3.35 (2H, m, partially obscured by solvent), 3.00 (1H, m), 2.88 (2H, m), 2.77 (1H, m), 2.62 (1H, m), 2.03 (6H, s), 1.21 (3H, d), 1.08 (3H, d) ppm.

LRMS (APCI): m/z [M+H]⁺ 674.

Optical Rotation $[\alpha]^D_{25}$=49.81° c=1, methanol

Preparation 14

N-[4-({2-[3-((2R)-2-{(2R)-2-[6-(2,5-Dimethyl-pyrrol-1-yl)-pyridin-3-yl]-2-hydroxy-ethylamino}-propyl)-phenyl]-acetylamino}-methyl)-benzyl]-2,2-diphenyl-acetamide Prepared using the method for preparation 1 using the acid from preparation 38 and the amine from preparation 57 to give the title compound as a colourless foam.

¹H NMR (400 MHz, CDCl₃): δ=8.50 (1H, m), 7.94–7.92 (1H, m), 7.30–7.08 (21H, m), 5.81 (2H, s), 4.97 (1H, s), 4.83–4.79 (1H, m), 4.35 (2H, s), 4.31 (2H, s), 3.51 (2H, s), 3.02–2.94 (1H, m), 2.89–2.84 (2H, m), 2.79–2.74 (1H, dd), 2.61–2.56 (1H, dd), 2.02 (6H, s), 1.06 (3H, d) ppm.

LRMS (APCI): m/z [M+H]⁺ 720, [M+Na]⁺ 742.

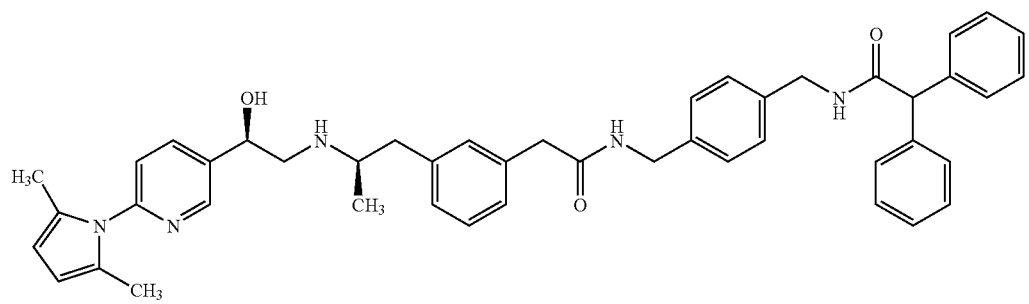

Preparation 15

N-{4-[(Benzhydryl-amino)-methyl]-benzyl}-2-[3-((2R)-2-{(2R)-2-[6-(2,5-dimethyl-pyrrol-1-yl)-pyridin-3-yl]-2-hydroxy-ethylamino}-propyl)-phenyl]-acetamide

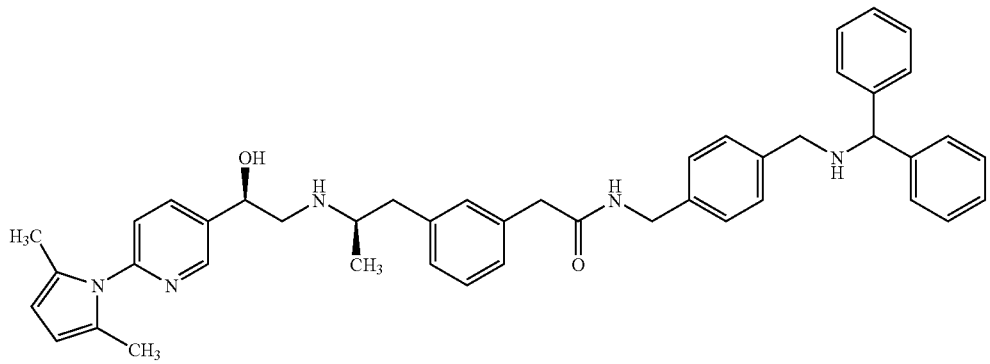

Prepared using the method for preparation 1 using the acid from preparation 38 and the amine from preparation 60 to give the title compound as a colourless foam.

$^1$H NMR (400 MHz, CD$_3$OD): δ=8.49 (1H, bs), 7.91 (1H, bd), 7.36–7.08 (19H, m), 5.81 (2H, s), 4.82–4.80 (1H, m), 4.75 (1H, s), 4.34 (2H, s), 3.84 (2H, s), 3.53 (2H, s), 2.85–2.63 (5H, m), 2.02 (6H, s), 1.06 (3H, d) ppm.

LRMS (APCI): m/z [M+H]$^+$ 692, [M+Na]$^+$ 714.

Preparation 16

N-(2-Benzyloxy-ethyl)-4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-benzamide Prepared using the method for preparation 1 using the acid from preparation 38 and the amine from preparation 62 to give the title compound as a colourless foam.

$^1$H NMR (400 MHz, CDCl$_3$): δ=8.46 (1H, s), 7.78–7.65 (1H, m), 7.56 (2H, d), 7.32–7.05 (10H, m), 6.97 (1H, d), 6.87 (1H, m), 5.86 (2H, s), 5.16–5.13 (1H, m), 4.50 (2H, s), 4.32 (2H, d), 3.64–3.57 (4H, m), 3.50 (2H, s), 3.37–3.32 (1H, m), 3.14–3.01 (3H, m), 2.78–2.73 (1H, m), 2.04 (6H, s) 1.19 (3H, d) ppm.

LRMS (electrospray): m/z [M+H]$^+$ 674, [M+Na]$^+$ 696.

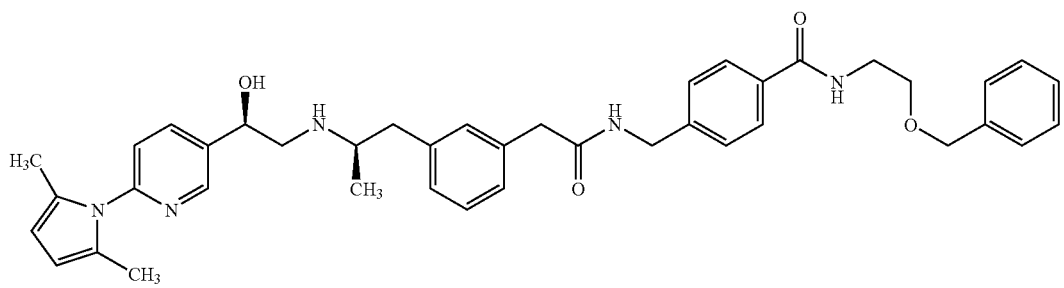

Preparation 17

4-({2-[3-((2R)-2-{(2R)-2-[6-(2,5-Dimethyl-pyrrol-1-yl)-pyridin-3-yl]-2-hydroxy-ethylamino}-propyl)-phenyl]-acetylamino}-methyl)-N-[2-(3-phenyl-propoxy)-ethyl]-benzamide

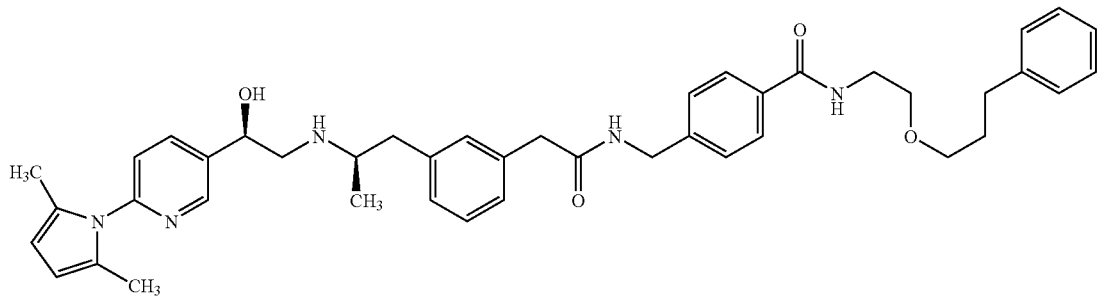

Prepared using the method for preparation 1 using the acid from preparation 38 and the amine from preparation 63 to give the title compound as a colourless foam.

$^1$H NMR (400 MHz, CDCl$_3$): δ=8.51 (1H, s), 7.82–7.80 (1H, m), 7.64–7.53 (3H, m), 7.33 (1H, m), 7.26–7.07 (9H, m), 6.95 (1H, d), 6.85 (1H, m), 5.86 (2H, s), 5.36–5.32 (1H, m), 4.37–4.28 (2H, m), 3.59–3.41 (9H, m), 3.26–3.14 (3H, m), 2.81–2.76 (1H, m), 2.64 (2H, t), 2.03 (6H, s), 1.89–1.83 (2H, m), 1.23 (3H, d) ppm.

LRMS (electrospray): m/z [M+H]$^+$ 702, [M+Na]$^+$ 724.

Preparation 18

4-({2-[3-((2R)-2-{(2R)-2-[6-(2,5-Dimethyl-pyrrol-1-yl)-pyridin-3-yl]-2-hydroxy-ethylamino}-propyl)-phenyl]-acetylamino}-methyl)-N-[2-(naphthalen-1-ylmethoxy)-ethyl]-benzamide Prepared using the method for preparation 1 using the acid from preparation 38 and the amine from preparation 64 to give the title compound as a colourless foam.

$^1$H NMR (400 MHz, CDCl$_3$): δ=8.37 (1H, s), 8.11 (1H, d), 7.87–7.80 (2H, m), 7.69–7.66 (1H, m), 7.48–7.39 (6H, m), 7.32–7.28 (1H, m), 7.15–7.08 (6H, m), 6.50 (1H, m), 6.33 (1H, m), 5.87 (2H, s), 4.97 (2H, s), 4.47–4.43 (1H, m), 4.41–4.27 (2H, m), 3.71–3.69 (2H, m), 3.63–3.59 (4H, m), 2.94–2.86 (2H, m), 2.76–2.58 (3H, m), 2.07 (6H, s), 1.13 (3H, d) ppm.

LRMS (electrospray): m/z [M+H]$^+$ 724, [M+Na]$^+$ 746.

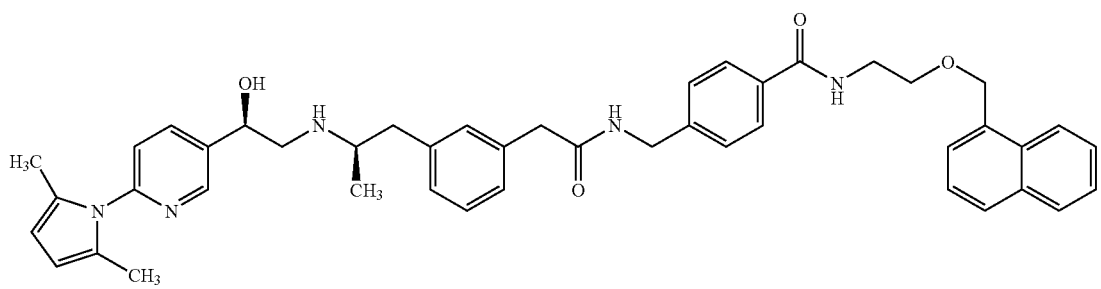

Preparation 19

N-(4-Benzylsulfamoyl-benzyl)-4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-benzamide

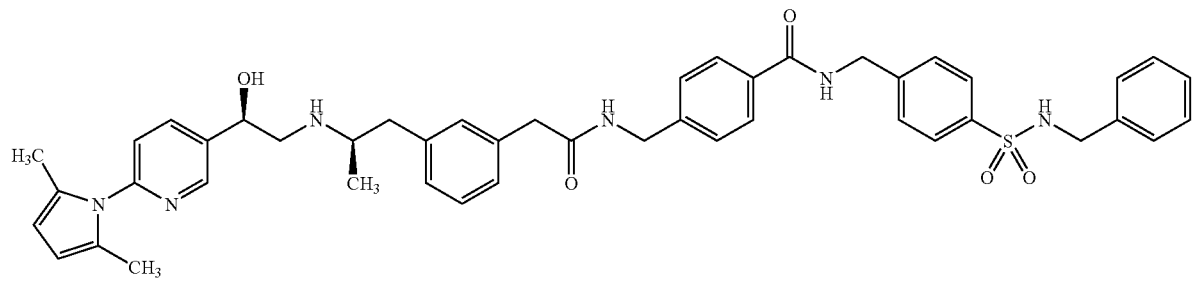

Prepared according to the method for preparation 1 using the acid from preparation 38 and the amine from preparation 67 to give the title compound as a colourless solid.

$^1$H NMR (400 MHz, CD$_3$OD): δ=8.50 (1H, s), 7.93 (1H, d), 7.78 (4H, m), 7.49 (2H, d), 7.33–7.10 (12H, m), 5.81 (2H, s), 4.84 (1H, m), 4.61 (2H, s), 4.41 (2H, s), 4.02 (2H, s), 3.55 (2H, s), 2.99 (1H, m), 2.86 (2H, m), 2.77 (1H, m), 2.60 (1H, m), 2.02 (6H, s), 1.07 (3H, d) ppm.

LRMS (APCI): m/z [M+H]$^+$ 799.

Preparation 20

4-({2-[3-((2R)-2-{(2R)-2-[6-(2,5-Dimethyl-pyrrol-1-yl)-pyridin-3-yl]-2-hydroxy-ethylamino}-propyl)-phenyl]-acetylamino}-methyl)-N-(4-methylsulfamoyl-benzyl)-benzamide Prepared according to the method for preparation 1 using the acid from preparation 38 and the amine from preparation 65 to give the title compound as a colourless solid.

$^1$H NMR (400 MHz, CD$_3$OD): δ=8.50 (1H, s), 7.93 (1H, d), 7.78 (4H, m), 7.53 (2H, d), 7.32–7.08 (7H, m), 5.81 (2H, s), 4.81 (1H, m), 4.62 (2H, s), 4.40 (2H, s), 3.55 (2H, s), 2.97 (1H, m), 2.86 (2H, m), 2.77 (1H, m), 2.58 (1H, m), 2.49 (3H, s), 2.02 (6H, s), 1.06 (3H, d) ppm.

LRMS (APCI): m/z [M+H]$^+$ 723.

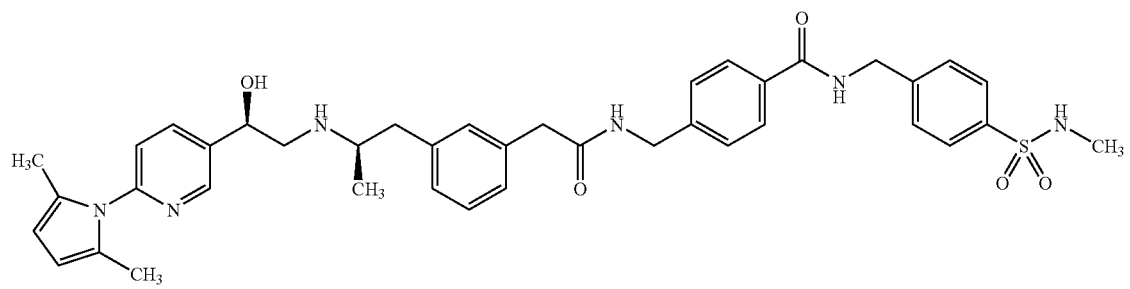

Preparation 21

4-({2-[3-((2R)-2-{(2R)-2-[6-(2,5-Dimethyl-pyrrol-1-yl)-pyridin-3-yl]-2-hydroxy-ethylamino}-propyl)-phenyl]-acetylamino}-methyl)-N-(4-ethylsulfamoyl-benzyl)-benzamide

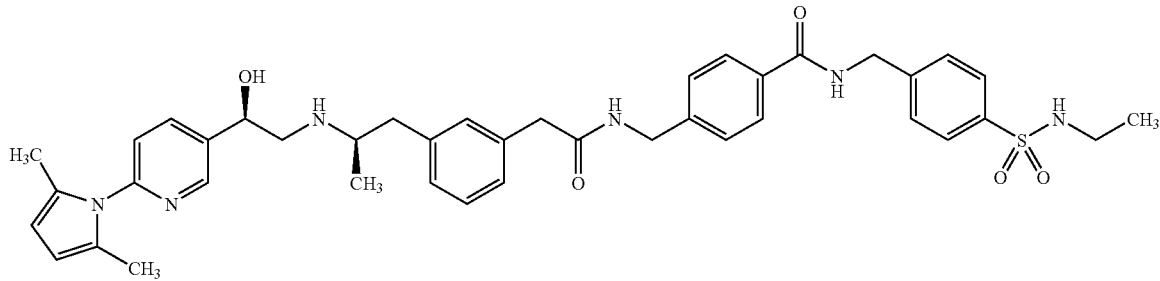

Prepared according to the method for preparation 1 using the acid from preparation 38 and the amine from preparation 66 to give the title compound as a colourless solid.

$^1$H NMR (400 MHz, CD$_3$OD): δ=8.50 (1H, s), 7.94 (1H, d), 7.80 (4H, d), 7.52 (2H, d), 7.32–7.08 (7H, m), 5.81 (2H, s), 4.81 (1H, m), 4.62 (2H, s), 4.40 (2H, s), 3.55 (2H, s), 2.99 (1H, m), 2.86 (4H, m), 2.75 (1H, m), 2.60 (1H, m), 2.02 (6H, s), 1.06 (3H, d), 1.03 (3H, t) ppm.

LRMS (APCI): m/z [M+H]$^+$ 737.

Preparation 22

N-(3-Benzylsulfamoyl-benzyl)-4-({2-[3-((2R)-2-{(2R)-2-[6-(2,5-dimethyl-pyrrol-1-yl)-pyridin-3-yl]-2-hydroxy-ethylamino}-propyl)-phenyl]-acetylamino}-methyl)-benzamide Prepared according to the method for preparation 1 using the acid from preparation 38 and the amine from preparation 70 to give the title compound as a colourless solid.

$^1$H NMR (400 MHz, CD$_3$OD): δ=8.50 (1H, s), 7.91 (1H, d), 7.79 (3H, m), 7.71 (1H, d), 7.57 (1H, d), 7.46 (1H, t), 7.31–7.07 (12H, m), 5.81 (2H, s), 4.81 (1H, m), 4.58 (2H, s), 4.40 (2H, s), 4.02 (2H, s), 3.54 (2H, s), 2.96 (1H, m), 2.85 (2H, m), 2.75 (1H, m), 2.59 (1H, m), 2.02 (6H, s), 1.06 (3H, d) ppm.

LRMS (APCI): m/z [M+H]$^+$ 799.

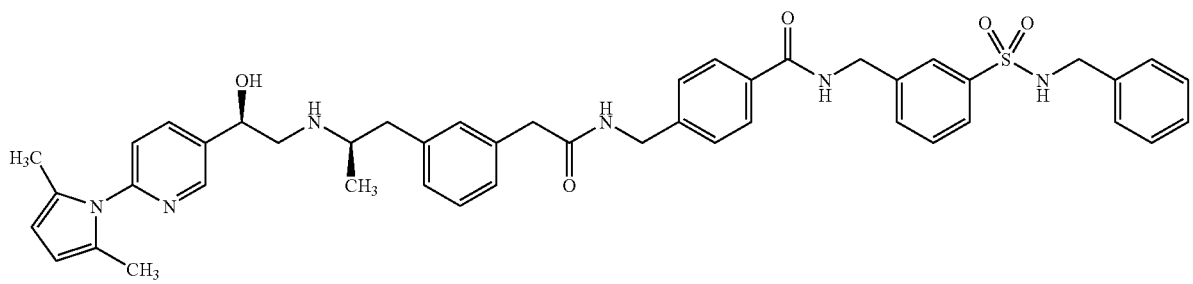

Preparation 23

4-({2-[3-((2R)-2-{(2R)-2-[6-(2,5-Dimethyl-pyrrol-1-yl)-pyridin-3-yl]-2-hydroxy-ethylamino}-propyl)-phenyl]-acetylamino}-methyl)-N-(3-methylsulfamoyl-benzyl)-benzamide

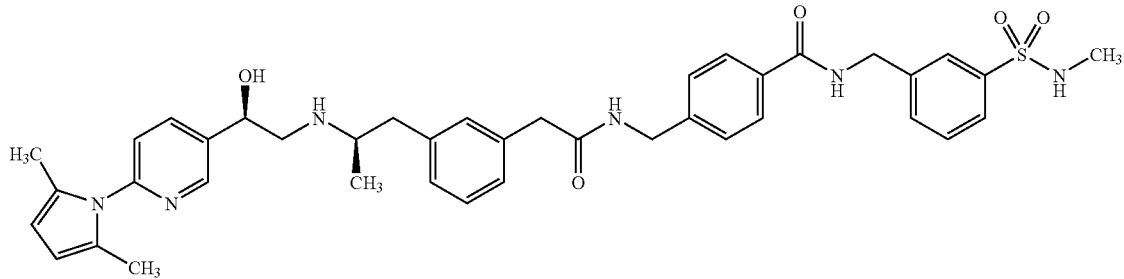

Prepared according to the method for preparation 1 using the acid from preparation 38 and the amine from preparation 68 to give the title compound as a colourless solid.

$^1$H NMR (400 MHz, CD$_3$OD): δ=8.50 (1H, s), 7.92 (1H, d), 7.82 (1H, s), 7.79 (2H, d), 7.72 (1H, d), 7.58 (1H, d), 7.52 (1H, t), 7.32–7.10 (7H, m), 5.81 (2H, s), 4.83 (1H, m), 4.62 (2H, s), 4.40 (2H, s), 3.55 (2H, s), 2.99 (1H, m), 2.86 (2H, m), 2.76 (1H, m), 2.60 (1H, m), 2.49 (3H, s), 2.02 (6H, m), 1.07 (3H, d) ppm.

LRMS (APCI): m/z [M+H]$^+$ 723.

Prepared according to the method for preparation 1 using the acid from preparation 38 and the amine from preparation 69 to give the title compound as a colourless solid.

$^1$H NMR (400 MHz, CD$_3$OD): δ=8.50 (1H, s), 7.94 (1H, d), 7.83 (1H, s), 7.79 (2H, d), 7.73 (1H, d), 7.59 (1H, d), 7.50 (1H, m), 7.32–7.08 (7H, m), 5.81 (2H, s), 4.81 (1H, m), 4.61 (2H, s), 4.40 (2H, s), 3.55 (2H, s), 2.99 (1H, m), 2.87 (4H, m), 2.76 (1H, m), 2.60 (1H, m), 2.02 (6H, s), 1.07 (3H, d), 1.01 (3H, t) ppm.

LRMS (APCI): m/z [M+H]$^+$ 737.

Preparation 24

4-({2-[3-((2R)-2-{(2R)-2-[6-(2,5-Dimethyl-pyrrol-1-yl)-pyridin-3-yl]-2-hydroxy-ethylamino}-propyl)-phenyl]-acetylamino}-methyl)-N-(3-ethylsulfamoyl-benzyl)-benzamide

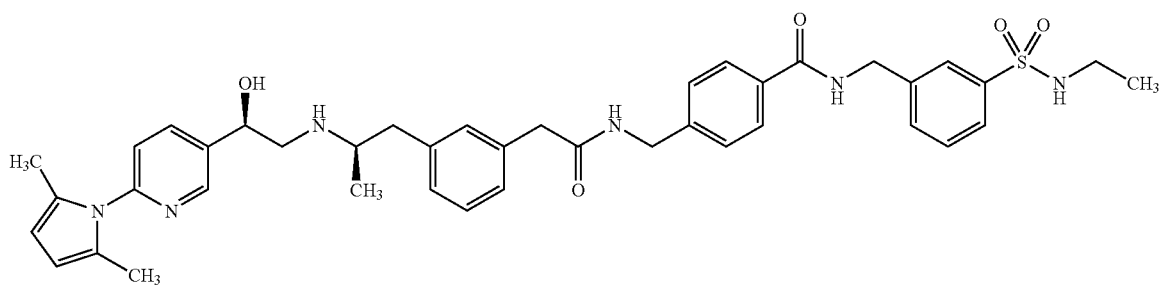

Preparation 25

N-(4-Benzylsulfamoyl-benzyl)-2-[3-((2R)-2{(2R)-2-[6-(2,5-dimethyl-pyrrol-1-yl)-pyridin-3-yl]-2-hydroxy-ethylamino}-propyl)-phenyl]-acetamide Prepared using the method for preparation 1 using the acid from preparation 40 and the amine from preparation 70 to give the title compound as a colourless solid.

$^1$H NMR (400 MHz, CDCl$_3$): δ=8.37 (1H, s), 7.66–7.60 (3H, m), 7.35–7.11 (12H, m), 6.72 (1H, m), 5.86 (2H, s), 4.48–4.45 (1H, m), 4.34.4.24 (2H, m), 4.01 (2H, s), 3.58 (2H, s), 2.96–2.55 (5H, m), 2.01 (6H, s), 1.14 (3H, d) ppm.

LRMS (APCI): m/z [M+H]$^+$ 666.

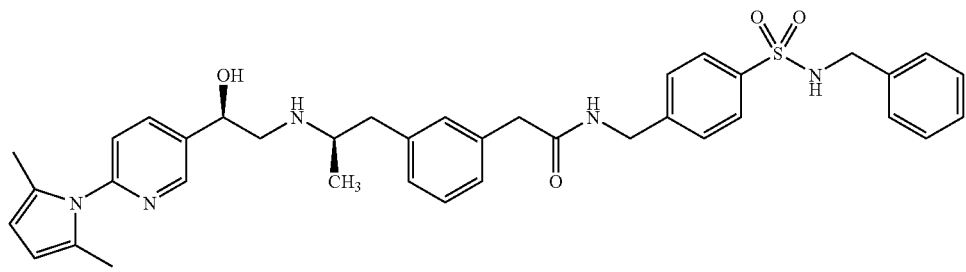

Prepared using the method for preparation 1 using the acid from preparation 40 and the amine from preparation 67 to give the title compound as a colourless solid.

$^1$H NMR (400 MHz, CDCl$_3$): δ=8.38 (1H, s), 7.70–7.65 (3H, m), 7.29–7.10 (12H, m), 6.66–6.63 (1H, m), 5.86 (2H, s), 4.51–4.48 (1H, m), 4.39–4.26 (2H, m), 403 (2H, s), 3.60 (2H, s), 2.97–2.87 (2H, m), 2.75–2.59 (3H, m), 2.04 (6H, s), 1.14 (3H, d) ppm.

LRMS (APCI): m/z [M+H]$^+$ 666.

Preparation 26

N-(3-Benzylsulfamoyl-benzyl)-2-[3-((2R)-2-{(2R)-2-[6-(2,5-dimethyl-pyrrol-1-yl)-pyridin-3-yl]-2-hydroxy-ethylamino}-propyl)-phenyl]-acetamide

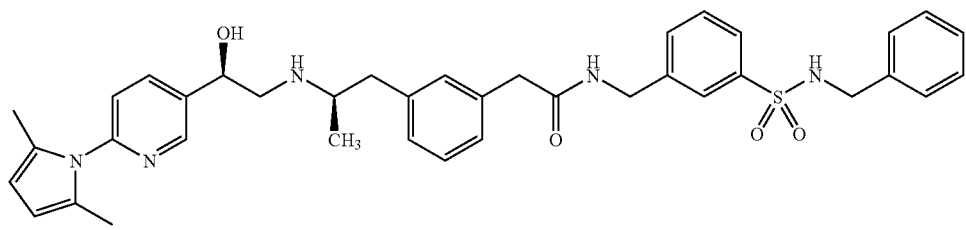

Preparation 27

N-(3,4-Dimethoxy-benzyl)-4-({2-[4-(2-{(2R)-2-[6-(2,5-dimethyl-pyrrol-1-yl)-pyridin-3-yl]-2-hydroxy-ethylamino}-propyl)-phenyl]-acetylamino}-methyl)-benzamide Prepared according to the method for preparation 1 using the acid from preparation 42 and the appropriate amine to give the title compound as a pale yellow foam which was used without further purification.

LRMS (APCI): m/z [M+H]$^+$ 674.

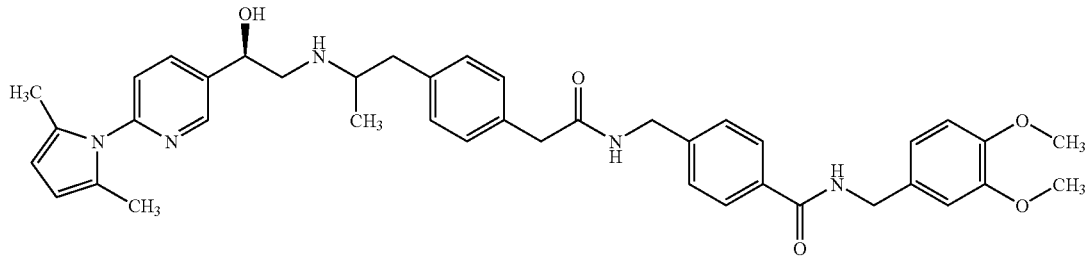

Prepared according to the method for preparation 1 using the acid from preparation 42 and the appropriate amine to give the title compound as a pale yellow foam which was used without further purification.
LRMS (APCI): m/z [M+H]$^+$ 690.

Preparation 28

4-({2-[4-(2-{(2R)-2-[6-(2,5-Dimethyl-pyrrol-1-yl)-pyridin-3-yl]-2-hydroxy-ethylamino}-propyl)-phenyl]-acetylamino}-methyl)-N-(2-ethoxy-benzyl)-benzamide

Preparation 29

4-({2-[4-(2-{(2R)-2-[6-(2,5-Dimethyl-pyrrol-1-yl)-pyridin-3-yl]-2-hydroxy-ethylamino}-propyl)-phenyl]-acetylamino}-methyl)-N-[(1R)-1-(4-methoxy-phenyl)-ethyl]-benzamide

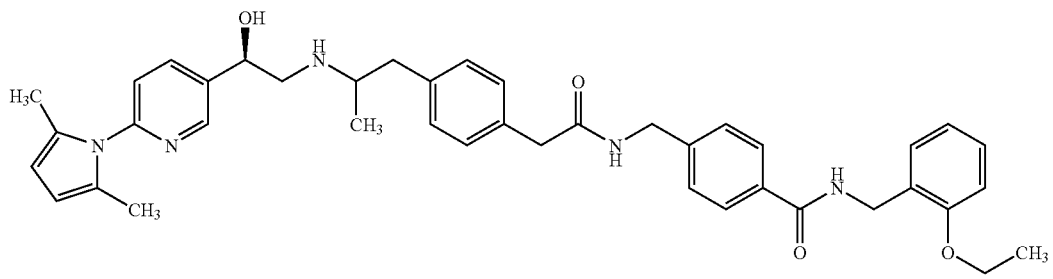

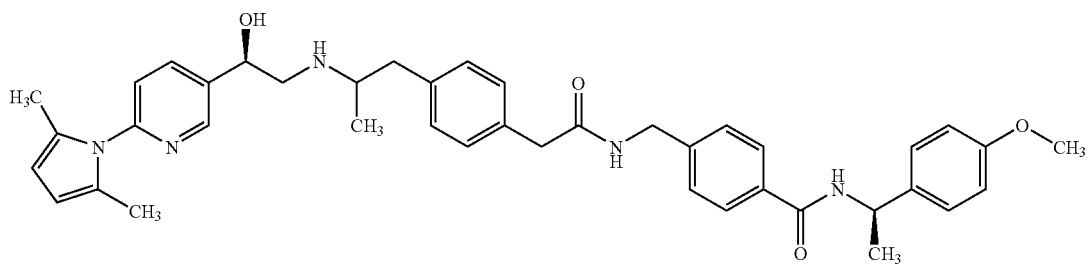

Prepared according to the method for preparation 1 using the acid from preparation 42 and the appropriate amine to give the title compound as a pale yellow foam which was used without further purification.
LRMS (APCI): m/z [M+H]+ 674.

Preparation 30

4-({2-[4-(2-{(2R)-2-[6-(2,5-Dimethyl-pyrrol-1-yl)-pyridin-3-yl]-2-hydroxy-ethylamino}-propyl)-phenyl]-acetylamino}-methyl)-N-((1R)-1-hydroxymethyl-2-phenyl-ethyl)-benzamide Prepared according to the method for preparation 1 using the acid from preparation 42 and the appropriate amine to give the title compound as a pale yellow foam which was used without further purification.

LRMS (APCI): m/z [M+H]+ 674.

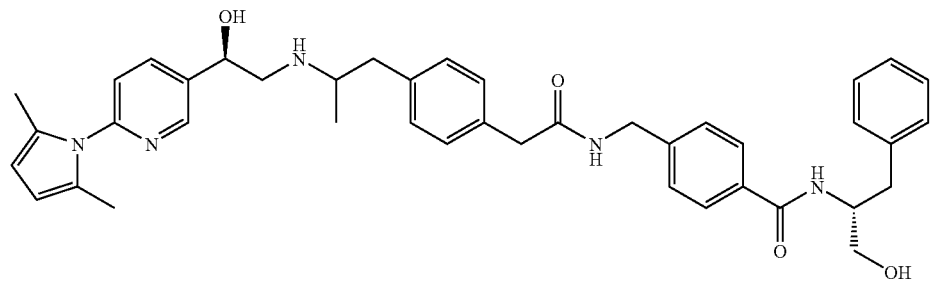

Prepared according to the method for preparation 1 using the acid from preparation 42 and the appropriate amine to give the title compound as a pale yellow foam which was used without further purification.
LRMS (APCI): m/z [M+H]+ 674.

Preparation 31

4-({2-[4-(2-{(2R)-2-[6-(2,5-Dimethyl-pyrrol-1-yl)-pyridin-3-yl]-2-hydroxy-ethylamino}-propyl)-phenyl]-acetylamino}-methyl)-N-((1R, 2S)-2-hydroxy-1-methyl-2-phenyl-ethyl)-benzamide

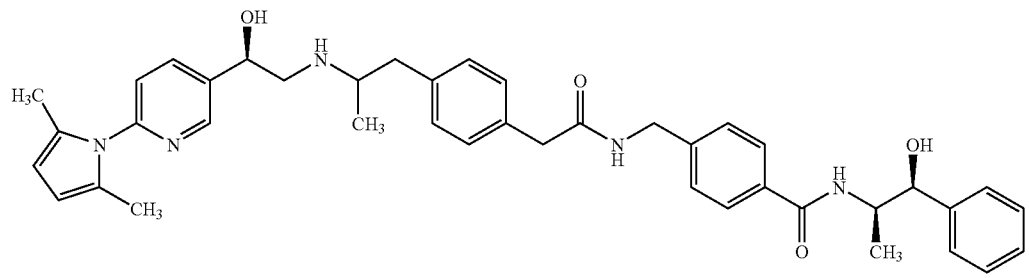

Preparation 32

4-({2-[4-(2-{(2R)-2-[6-(2,5-Dimethyl-pyrrol-1-yl)-pyridin-3-yl]-2-hydroxy-ethylamino}-propyl)-phenyl]-acetylamino}-methyl)-N-((1S, 2R)-2-hydroxy-1-methyl-2-phenyl-ethyl)-benzamide

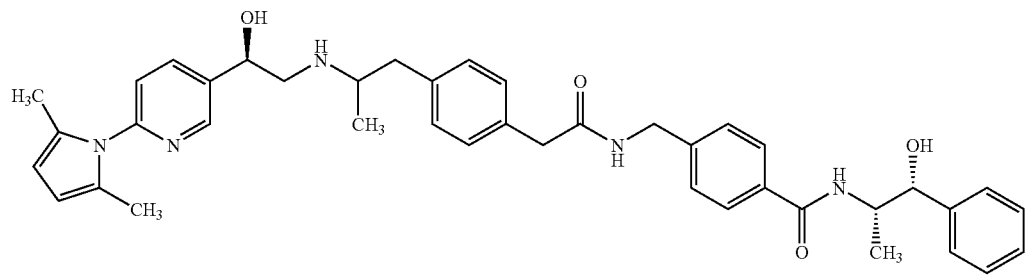

Prepared according to the method for preparation 1 using the acid from preparation 42 and the appropriate amine to give the title compound as a pale yellow foam which was used without further purification.

LRMS (APCI): m/z [M+H]$^+$ 674.

Preparation 33

4-({2-[4-(2-{(2R)-2-[6-(2,5-Dimethyl-pyrrol-1-yl)-pyridin-3-yl]-2-hydroxy-ethylamino}-propyl)-phenyl]-acetylamino}-methyl)-N-[2-(3-methoxy-phenyl)-ethyl]-benzamide Prepared according to the method for preparation 1 using the acid from preparation 42 and the appropriate amine to give the title compound as a pale yellow foam which was used without further purification.

LRMS (APCI): m/z [M+H]$^+$ 674.

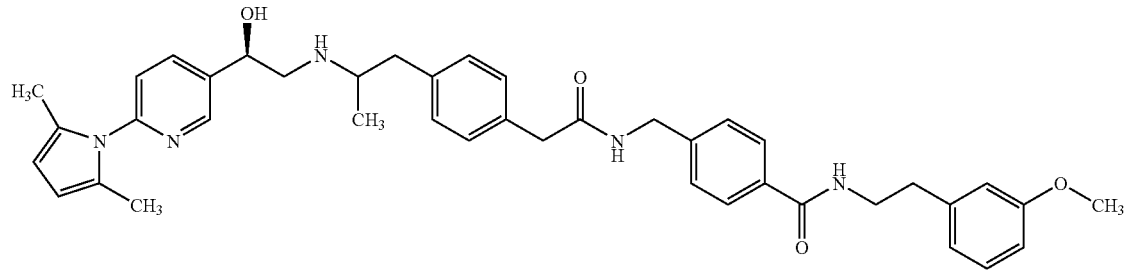

Preparation 34

4-({2-[3-(2-{(2R)-2-[6-(2,5-Dimethyl-pyrrol-1-yl)-pyridin-3-yl]-2-hydroxy-ethylamino}-propyl)-phenyl]-acetylamino}-methyl)-benzoic acid

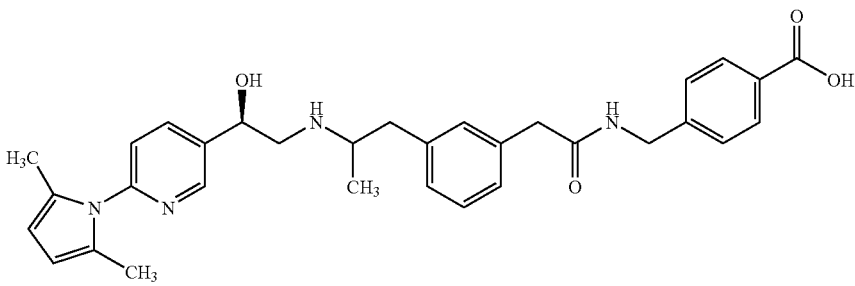

A solution of the ester from preparation 35 (1.31 g, 2.36 mmol) in tetrahydrofuran (10 ml) was treated with 1 N lithium hydroxide (4.7 ml, 4.7 mmol) and the resulting mixture left to stir at room temperature for 16 hours. The solvent was removed in vacuo and the residue purified by flash column chromatography eluting with dichloromethane:methanol:880 ammonia (90:10:1 by volume) to give the title compound (1:1 mixture of diastereoisomers) as a colourless solid (0.88 g).

$^1$H NMR (400 MHz, CD$_3$OD): δ=8.72–8.58 (1H, m), 8.14–8.04 (1H, m), 7.95–7.84 (2H, m), 7.45–7.07 (7H, m), 5.83 (2H, s), 5.17–5.04 (1H, m), 4.39 (2H, s), 3.55 (2H, s), 3.46–3.01 (4H, m), 2.77–2.58 (1H, m), 2.05 (6H, s), 1.23–1.0 (3H, m) ppm.

LRMS (electrospray): m/z [M+H]$^+$ 541, [M+Na]$^+$ 563.

Preparation 35

4-({2-[3-(2-{(2R)-2-[6-(2,5-Dimethyl-pyrrol-1-yl)-pyridin-3-yl]-2-hydroxy-ethylamino}-propyl)-phenyl]-acetylamino}-methyl)-benzoic acid methyl ester

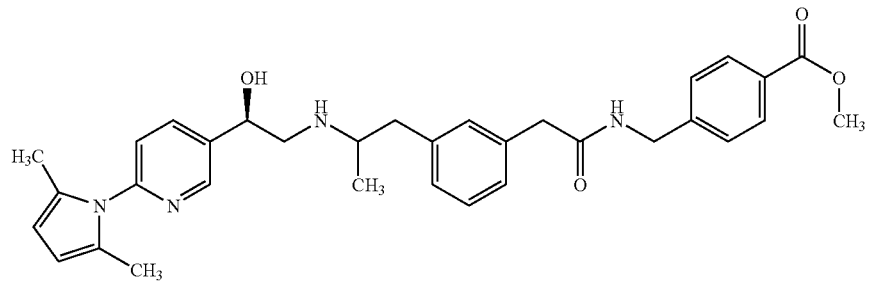

Prepared using the procedure for preparation 1 using the acid from preparation 36 and the appropriate amine to give the title compound (1:1 mixture of diastereoisomers) as a pale yellow oil.

$^1$H NMR (400 MHz, CDCl$_3$): δ=8.46–8.42 (1H, m), 7.94–7.90 (2H, m), 7.76 (1H, m), 7.32–7.10 (7H, m), 6.31–6.20 (1H, m), 5.88 (2H, s), 4.72–4.51 (1H, m), 4.44–4.33 (2H, m), 3.88 (3H, s), 3.64–3.61 (2H, m), 3.13–3.11 (1H, m), 2.85–2.57 (4H, m), 2.08–2.07 (6H, s), 1.19–1.14 (3H, m) ppm.

LRMS (electrospray): m/z [M+H]$^+$ 555, [M+Na]$^+$ 577.

Preparation 36

[3-(2-{(2R)-2-[6-(2,5-Dimethyl-pyrrol-1-yl)-pyridin-3-yl]-2-hydroxy-ethylamino}-propyl)-phenyl]-acetic acid

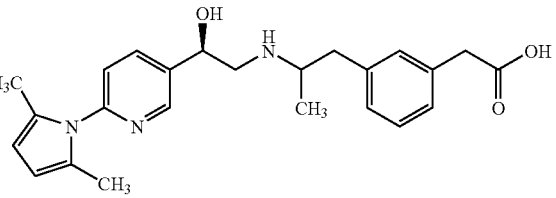

Prepared using the method for preparation 34 using the ester from preparation 37 to give the title compound (1:1 mixture of diastereoisomers) as an off white solid.

$^1$H NMR (400 MHz, DMSO$_{d6}$): δ=8.55 (1H, s), 7.93 (1H, t), 7.35 (1H, d), 7.18–7.15 (1H, m), 7.10–7.03 (3H, m), 5.77 (2H, s), 4.87–4.80 (1H, m), 3.48 (2H, s), 3.01–2.89 (4H, m), 2.50–2.40 (1H, m, partially masked by solvent), 2.01 (6H, s), 0.96 (3H, d) ppm.

LRMS (electrospray): m/z [M+H]$^+$ 408.

Preparation 37

[3-(2-{(2R)-2-[6-(2,5-Dimethyl-pyrrol-1-yl)-pyridin-3-yl]-2-hydroxy-ethylamino}-propyl)-phenyl]-acetic acid methyl ester

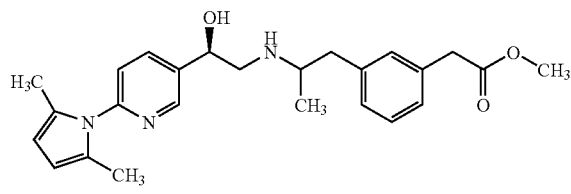

Prepared according to the procedure for preparation 52 using the ketone from preparation 53 and the amine from preparation 46 to give the title compound (1:1 mixture of diastereoisomers) as a pale yellow oil.

$^1$H NMR (400 MHz, CDCl$_3$): δ=8.56 (1H, s), 7.87–7.84 (1H, m), 7.30–7.26 (1H, m, partially masked by solvent), 7.20–7.09 (4H, m), 5.88 (2H, s), 4.97–4.87 (1H, m), 3.69 (3H, s), 3.62 (2H, s), 3.18–3.03 (2H, m), 2.94–2.74 (3H, m), 2.10 (6H, s), 1.22 (3H, d) ppm.

LRMS (electrospray): m/z [M+H]$^+$ 422.

Preparation 38

4-({2-[3-((2R)-2-{(2R)-2-[6-(2,5-Dimethyl-pyrrol-1-yl)-pyridin-3-yl]-2-hydroxy-ethylamino}-propyl)-phenyl]-acetylamino}-methyl)-benzoic acid

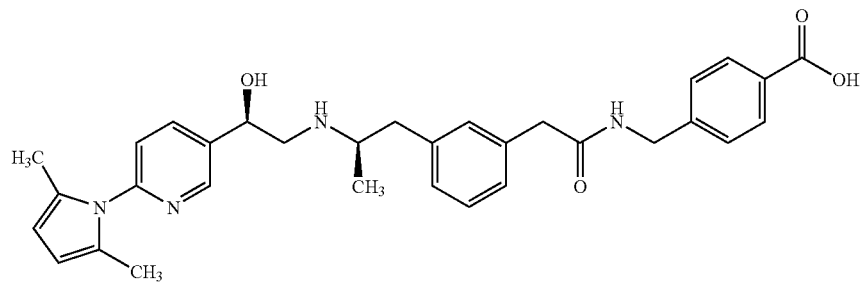

Prepared using the method for preparation 34 using the ester from preparation 39 to give the title compound as a colourless solid.

$^1$H NMR (400 MHz, CD$_3$OD): δ=8.70 (1H, m), 8.64 (1H, d), 8.09 (1H, d), 7.93 (2H, d), 7.41 (1H, d), 7.34–7.19 (5H, m), 5.83 (2H, s), 5.12 (1H, m), 4.44 (2H, s), 3.59 (3H, m), 3.39 (2H, m), 3.22 (1H, m), 2.82 (1H, m), 2.05 (6H, s), 1.28 (3H, d) ppm.

LCMS: m/z [M+H]$^+$ 541.

Optical Rotation [α]$^D_{25}$=−27.71° c=1, methanol

Preparation 39

4-({2-[3-((2R)-2-{(2R)-2-[6-(2,5-Dimethyl-pyrrol-1-yl)-pyridin-3-yl]-2-hydroxy-ethylamino}-propyl)-phenyl]-acetylamino}-methyl)-benzoic acid methyl ester

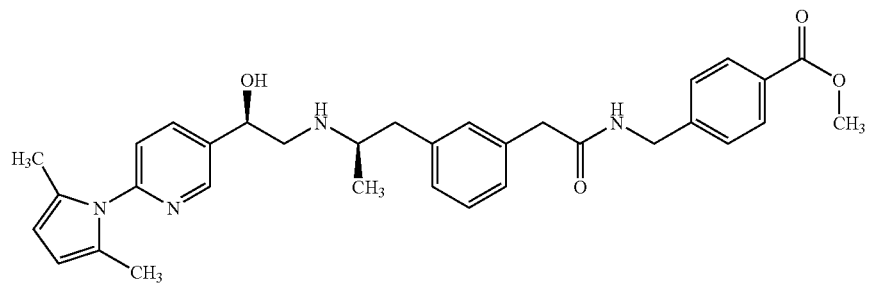

Prepared using the procedure for preparation 1 using the acid from preparation 40 and the appropriate amine to give the title compound as a pale yellow solid.

$^1$H NMR (400 MHz, CD$_3$OD): δ=8.62 (1H, s), 8.06 (1H, d), 7.92 (2H, d), 7.70 (1H, d), 7.68 (1H, d), 7.37–7.16 (5H, m), 5.83 (2H, s), 5.11 (1H, m), 4.42 (2H, s), 3.87 (3H, s), 3.60–3.52 (3H, m), 3.38–3.24 (2H, m, partially obscured by solvent), 3.18 (1H, m), 2.80 (1H, m), 2.04 (6H, s), 1.26 (3H, d) ppm.

LRMS (APCI): m/z [M+H]$^+$ 555.

Optical Rotation [α]$^D_{25}$=−27.71° c=1, methanol

Preparation 40

[3-((2R)-2-{(2R)-2-[6-(2,5-Dimethyl-pyrrol-1-yl)-pyridin-3-yl]-2-hydroxy-ethylamino}-propyl)-phenyl]-acetic acid

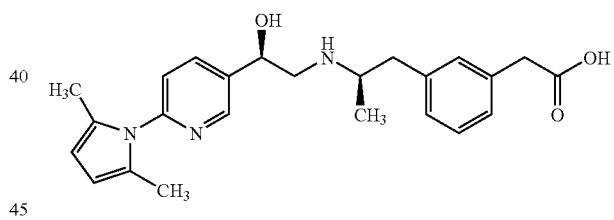

Prepared using the method for preparation 34 using the ester from preparation 41 to give the title compound as a colourless solid.

$^1$H NMR (400 MHz, DMSO$_{d6}$): δ=8.54 (1H, bs), 7.92–7.90 (1H, m), 7.33 (1H, d), 7.16 (1H, d), 7.07–7.00

(3H, m), 5.77 (2H, s), 4.77–4.74 (1H, m), 3.47 (2H, s), 2.91–2.75 (4H, m), 2.43–2.38 (1H, m), 2.01 (6H, s), 0.92 (3H, d) ppm.

LRMS (APCI): m/z [M+H]+ 408.

Preparation 42

4-({2-[4-(2-{(2R)-2-[6-(2,5-Dimethyl-pyrrol-1-yl)-pyridin-3-yl]-2-hydroxy-ethylamino}-propyl)-phenyl]-acetylamino}-methyl)-benzoic acid

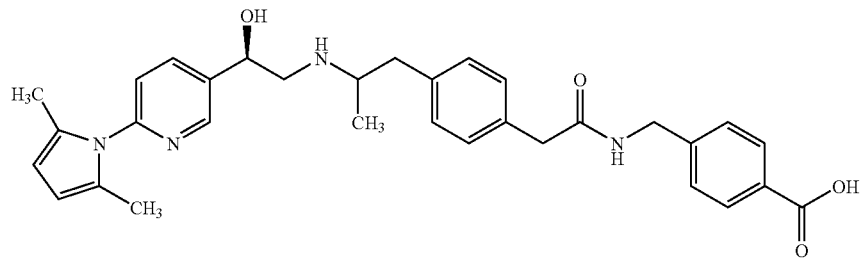

Preparation 41

[3-((2R)-2-{(2R)-2-[6-(2,5-Dimethyl-pyrrol-1-yl)-pyridin-3-yl]-2-hydroxy-ethylamino}-propyl)-phenyl]-acetic acid methyl ester

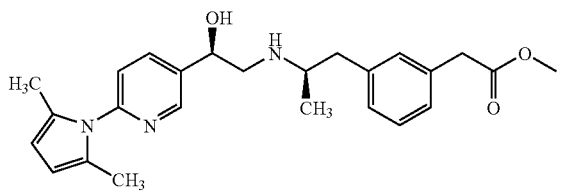

A solution of the epoxide from preparation 48 (5.43 g of 66% b/w crude material, 3.58 g, 16.7 mmol) and the amine from preparation 51 (4.15 g, 20.02 mmol) in dimethyl sulfoxide (50 ml) was heated at 85° C. under nitrogen for a period of 16 hours. The reaction mixture was cooled to room temperature and loaded directly onto a Strong Cation Exchange column. The column was eluted with methanol (300 ml) and then the product eluted with 2M ammonia in methanol (100 ml). The solvent was removed in vacuo and the residue purified by flash column chromatography eluting with dichloromethane:methanol:880 ammonia (100 changing to 98:2:0.2 by volume) to give the title compound as a pale orange oil (5.45 g).
1H NMR (400 MHz, CD3OD): δ=8.54 (1H, bs), 7.79 (1H, dd), 7.31–7.22 (2H, m), 7.15–7.10 (3H, m), 5.82 (2H, s), 491–4.81 (1H, m, partially obscured by solvent), 3.67 (3H, s), 3.63 (2H, s), 3.04–2.96 (1H, m), 2.88 (2H, d), 2.81–2.74 (1H, m), 2.66–2.58 (1H, m), 2.04 (6H, s), 1.09 (3H, d) ppm.
LRMS (electrospray): m/z [M+H]+ 422, [M+Na]+ 444, [M–H]– 420.

Prepared using the method for preparation 34 using the ester from preparation 43 to give the title compound (1:1 mixture of diastereoisomers) as a pale yellow solid which was used without further purification.
LRMS (electrospray): m/z [M+H]+ 541, [M–H]– 539.

Preparation 43

4-({2-[4-(2-{(2R)-2-[6-(2,5-Dimethyl-pyrrol-1-yl)-pyridin-3-yl]-2-hydroxy-ethylamino}-propyl)-phenyl]-acetylamino}-methyl)-benzoic acid methyl ester

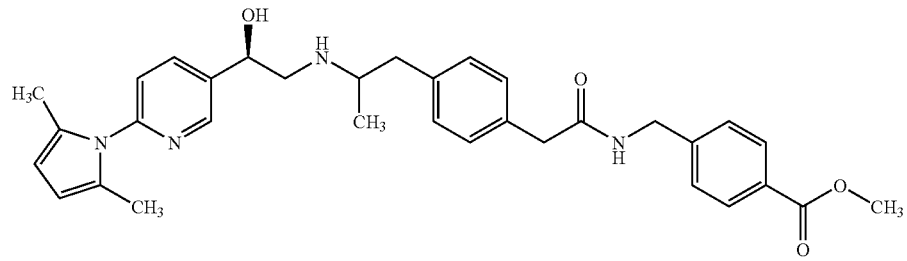

Prepared using the method for preparation 1 using the acid from preparation 44 and the appropriate amine to give the title compound (1:1 mixture of diastereoisomers) as an off white solid.

1H NMR (400 MHz, CD3OD): δ=8.50 (1H, d), 7.92 (3H, m), 7.32–7.16 (7H, m), 5.81 (2H, s), 4.81 (1H, m), 4.41 (2H, s), 3.87 (3H, s), 3.53 (2H, d), 2.98–2.75 (5H, m), 2.03 (6H, s), 1.08 (3H, d), ppm.

LRMS (electrospray): m/z [M+H]+ 555.

Preparation 44

[4-(2-{(2R)-2-[6-(2,5-Dimethyl-pyrrol-1-yl)-pyridin-3-yl]-2-hydroxy-ethylamino}-propyl)-phenyl]-acetic acid

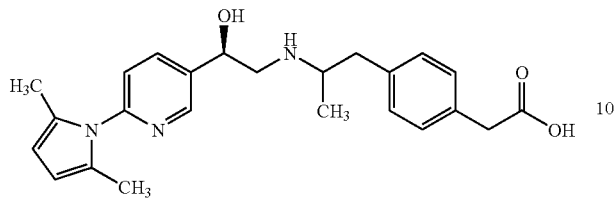

Prepared according to the procedure for preparation 34 using the ester from preparation 45 to give the title compound (1:1 mixture of diastereoisomers) as a colourless solid
$^1$H NMR (400 MHz, DMSO$_{d6}$): δ=8.55 (1H, s), 7.91 (1H, m), 7.36 (1H, d), 7.14 (4H, m), 5.77 (2H, s), 4.80 (1H, m), 3.50 (2H, bs), 2.94 (2H, m), 2.90 (3H, m), 2.01 (6H, s), 0.95 (3H, d) ppm.
LRMS (electrospray): m/z [M+H]$^+$ 408, [M−H]$^−$ 406.

Preparation 45

[4-(2-{(2R)-2-[6-(2,5-Dimethyl-pyrrol-1-yl)-pyridin-3-yl]-2-hydroxy-ethylamino}-propyl)-phenyl]-acetic acid methyl ester

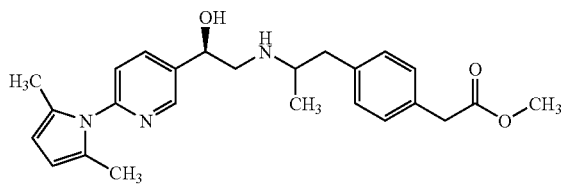

Prepared according to the procedure for preparation 52 using the ketone from preparation 55 and the amine from preparation 46 to give the title compound (1:1 mixture of diastereoisomers) as a yellow gum.
$^1$H NMR (400 MHz, CDCl$_3$): δ=8.53 (1H, m), 7.83–7.79 (1H, m), 7.26–7.13 (5H, m), 5.88 (2H, s), 4.73–4.64 (1H, m), 3.69 (3H, s), 3.60 (2H, s), 3.09–2.96 (2H, m), 2.79–2.63 (3H, m), 2.09 (6H, s), 1.13 (3H, t) ppm.
LRMS (electrospray): m/z [M+H]$^+$ 422.

Preparation 46

(1R)-2-Amino-1-[6-(2,5-dimethyl-pyrrol-1-yl)-pyridin-3-yl]-ethanol

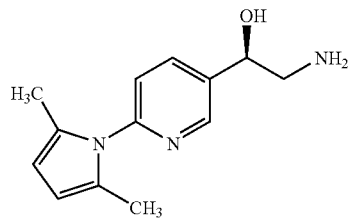

A solution of the phthalimide from preparation 47 (4.85 g, 13.4 mmol) in 8M methylamine in ethanol (50 ml) was stirred under a nitrogen atmosphere at room temperature for 18 hours. The reaction was concentrated under reduced pressure and the residue was dissolved in methanol. This solution was passed through a Strong Cation Exchange resin cartridge eluting with methanol and then 2N ammonia in methanol to elute the product. The eluent was concentrated in vacuo and the residue purified by flash column chromatography on silica gel eluting with dichloromethane:methanol:880 ammonia (95:5:0 changing to 90:10:1, by volume) to give the title compound as a pale yellow solid (1.6 g).
$^1$H NMR (400 MHz, CDCl$_3$): δ=8.17 (1H, s), 7.85 (1H, d), 7.21 (1H, d), 5.89 (2H, s), 4.69 (1H, t), 3.15–3.11 (1H, dd), 2.85–2.80 (1H, dd), 2.11 (6H, s) ppm.
LRMS (electrospray): m/z [M+H]$^+$ 232, [M+Na]$^+$ 254.

Preparation 47

2-{(2R)-2-[6-(2,5-Dimethyl-pyrrol-1-yl)-pyridin-3-yl]-2-hydroxy-ethyl}-isoindole-1,3-dione

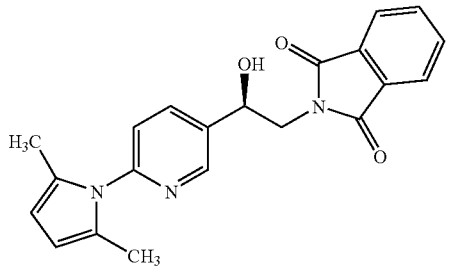

A solution of the crude epoxide from preparation 48 (30.0 g of 65% b/w epoxide, 19.50 g, 91.0 mmol), phthalimide (12.51 g, 85.0 mmol) and potassium phthalimide (2.78 g, 15.0 mmol) in N,N-dimethylformamide (200 ml) was heated at 90° C. under nitrogen for 6 hours. After cooling the reaction was stirred at room temperature for 18 hours, concentrated in vacuo and the residue partitioned between dichloromethane (600 ml) and water (400 ml). The organic phase was separated and the aqueous phase extracted with further dichloromethane (200 ml). The combined organic extracts were dried (magnesium sulfate) and concentrated in vacuo. Crystallisation (ethyl acetate, 300 ml) gave the title compound as a pale yellow crystalline solid (22.1 g).
$^1$H NMR (400 MHz, DMSO-d$_6$): δ=8.42 (1H, s), 7.90 (1H, d), 7.80 (4H, d), 7.30 (1H, d), 5.90 (1H, s), 5.80 (2H, s), 5.00 (1H, brs), 3.82 (1H, m), 3.75 (1H, m), 1.95 (6H, s) ppm.
LRMS (electrospray): m/z [M+H]$^+$ 362.

Preparation 48

2-(2,5-Dimethyl-pyrrol-1-yl)-5-[(2R)-oxiranyl]pyridine

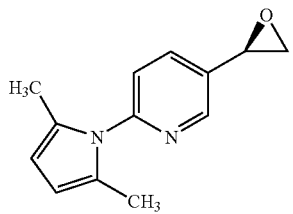

A solution of the chloride from preparation 49 (12.0 g, 48.1 mmol) in tetrahydrofuran (20 ml) was slowly added to a solution of (−)-B-chlorodiisopinocampheylborane (20.1 g, 62.5 mmol) in tert-butyl methylether (15 ml) and tetrahydrofuran (30 ml) at −30° C. under nitrogen. The reaction was stirred for 6 hours at −30° C. and then sodium perborate tetrahydrate (7.4 g, 48.1 mmol) followed by tert-butyl methylether (50 ml) were added. The reaction was stirred at room temperature for 18 hours, treated with 2M aqueous sodium hydroxide (190 ml) and stirred for a further 6 hours. The organic phase was separated and the aqueous phase extracted with further tert-butyl methylether (50 ml). The combined organic extracts were washed with 1M aqueous sodium hydroxide (50 ml), saturated aqueous sodium chloride (50 ml), dried (sodium sulfate) and concentrated in vacuo. The residue was purified by flash column chromatography on silica gel eluting with pentane:dichloromethane (80:2 changing to 100:0, by volume) to give the crude epoxide (65% b/w, 11.0 g), which was used without further purification.

$^1$H NMR (400 MHz, CDCl$_3$): δ=8.58 (1H, bs), 7.68–7.66 (1H, dd), 7.22–7.20 (1H, d), 5.81 (2H, s), 3.97–3.96 (1H, m), 3.26–3.24 (1H, m), 2.91–2.89 (1H, m), 2.12 (6H, s) ppm.

LRMS (electrospray): m/z [M+H]$^+$ 215, [M+Na]$^+$, 237.

Preparation 49

2-Chloro-1-[6-(2,5-dimethyl-pyrrol-1-yl)-pyridin-3-yl]-ethanone

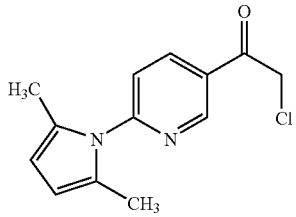

A solution of 2.5 M n-butyl lithium in hexane (35 ml, 87.6 mmol) was added to a solution of the bromide from preparation 50 (20.0 g, 79.7 mmol) in tert-butyl methylether (300 ml) at −78° C. under nitrogen over a 10 minutes. The reaction was stirred for a further 10 minutes and 2-chloro-N-methoxy-N-methyl-acetamide (12.1 g, 87.6 mmol) in tert-butyl methylether (40 ml) was added slowly. The reaction was stirred at −78° C. for 20 minutes and then 1M hydrochloric acid (200 ml) was added. The mixture was allowed to warm to room temperature, stirred for 2 hours and the organic phase separated. The aqueous phase was extracted with tert-butyl methylether and the combined organic extracts were washed with water (100 ml), saturated aqueous sodium chloride (100 ml) and 1M sodium hydroxide (100 ml). The organic phase was dried (sodium sulfate), concentrated in vacuo and the residual oil purified by flash column chromatography on silica gel eluting with pentane:dichloromethane:methanol (75:25:0 changing to 0:99:1, by volume). Recrystallisation (pentane:dichloromethane) gave the title compound as a yellow solid (11.97 g).

$^1$H NMR (400 MHz, CDCl$_3$): δ=9.11 (1H, s), 8.34–8.33 (1H, d), 7.32–7.30 (1H, d), 5.91 (2H, s), 4.66 (2H, s), 2.17 (6H, s) ppm.

LRMS (thermospray): m/z [M−H]$^+$ 247.

Preparation 50

5-Bromo-2-(2,5-dimethyl-pyrrol-1-yl)-pyridine

2,5-hexanedione (46.2 g, 0.41 mol) was added to a suspension of 2-amino-5-bromopyridine (50.0 g, 0.29 mol) and the reaction heated to reflux for 24 hours under Dean and Stark conditions. para-Toluene sulfonic acid (100 mg) was added and the reaction was refluxed for a further 18 hours. 8 ml of water were removed, so the reaction was cooled to room temperature, washed with water (100 ml) and passed through a plug of silica gel, eluting with toluene. The eluent was concentrated in vacuo and the residue dissolved in pentane:dichloromethane (1:1 by volume) and passed through a plug of silica gel, eluting with pentane:dichloromethane (1:1 by volume). The eluent was concentrated in vacuo to give a red liquid, which solidified on standing. The solid was recrystallised from isopropanol to give the title compound as a pale yellow solid (54.4 g).

$^1$H NMR (400 MHz, CDCl$_3$): δ=8.66 (1H, s), 7.93–7.92 (1H, d), 7.13–7.11 (1H, d), 5.91 (2H, s), 2.13 (6H, s) ppm.

LRMS (thermospray): m/z [M+H]$^+$ 252.

Preparation 51

[3-((2R)-2-Amino-propyl)-phenyl]-acetic acid methyl ester

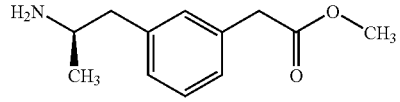

A solution of the amine from preparation 52 (7.69 g, 22 mmol) and ammonium formate (6.94 g, 110 mmol) was heated to 75° C. in the presence of 20% of palladium hydroxide-on-charcoal (2.00 g). After 90 minutes the reaction mixture was cooled to room temperature, filtered through arbocel® and the filtrate concentrated in vacuo. The residue was partitioned between dichloromethane (100 ml) and 880 ammonia (100 ml) and the organic phase separated. The aqueous phase was extracted with dichloromethane (100 ml) and the combined organic extracts dried (magnesium sulfate) and reduced in vacuo to give the title compound as a colourless oil (4.78 g).

$^1$H NMR (400 MHz, CD$_3$OD): δ=7.27–7.23 (1H, t), 7.13–7.09 (3H, m), 3.67 (3H, s), 3.63 (2H, s), 3.12–3.05 (1H, m), 2.67–2.57 (2H, m), 1.06 (3H, d) ppm.

LRMS (electrospray): m/z [M+H]$^+$ 208, [M+Na]$^+$ 230.

Preparation 52

{3-[(2R)-2-((1R)-1-Phenyl-ethylamino)-propyl]-phenyl}-acetic acid methyl ester

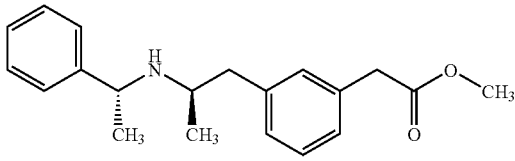

A solution of the ketone from preparation 53 (8.5 g, 41.2 mmol), (R)-α-methyl benzylamine (4.8 ml, 37.2 mmol), sodium triacetoxyborohydride (11.6 g, 56 mmol) and acetic acid (2.2 ml, 38 mmol) in dichloromethane (400 ml) was stirred at room temperature for 48 hours. The reaction mixture was quenched by addition of saturated aqueous sodium bicarbonate (200 ml) and allowed to stir until effervescence ceased. The organic phase was separated and the aqueous phase extracted with dichloromethane (100 ml). The combined organic extracts were dried (magnesium sulfate) and reduced in vacuo. Purification by flash column chromatography eluting with dichloromethane:methanol:880 ammonia (99:1:0.1 changing to 95:5:0.5 by volume) gave a 4:1 mixture of diastereomers (R,R major) as a pale yellow oil (8.71 g). Treatment with 1M hydrogen chloride in methanol followed by three successive crystallisations (di-isopropylether/methanol) gave the title compound as a colourless crystalline solid (5.68 g).

¹H NMR (400 MHz, CD₃OD): δ=7.52–7.48 (5H, m), 7.28–7.25 (1H, m), 7.18–7.16 (1H, m), 7.02–6.99 (2H, m), 4.59 (1H, q), 3.62 (2H, s), 3.30 (3H, s), 3.30–3.25 (2H, m), 3.26–3.15 (1H, m), 2.66–2.60 (1H, m), 1.68 (3H, d), 1.18, (3H, d) ppm.

LRMS (electrospray): m/z [M+H]⁺ 312, [M+Na]⁺ 334.

Preparation 53

[3-(2-Oxo-propyl)-phenyl]-acetic acid methyl ester

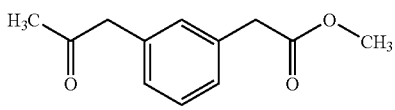

A solution of the bromide from preparation 26 (15.0 g, 65.0 mmol), tributyltin methoxide (28.3 ml, 98 mmol), isopropenyl acetate (10.8 ml, 98.0 mmol), palladium(II) acetate (750 mg, 3.30 mmol) and tri-ortho-tolylphosphine (2.0 g, 6.5 mmol) were stirred together in toluene (75 ml) at 100° C. under nitrogen for 5 hours. After cooling the reaction was diluted with ethyl acetate (150 ml) and 4M aqueous potassium fluoride solution (90 ml) and stirred for 15 minutes. The mixture was filtered through arbocel and the organic phase separated and reduced in vacuo. The residue was purified by flash column chromatography silica gel eluting with a solvent gradient of diethyl ether:pentane:dichloromethane (0:100:0 changing to 25:75:0 then to 0:0:100, by volume) to give the title compound as a pale yellow oil (12.6 g).

¹H NMR (400 MHz, CDCl₃): δ=7.30 (1H, t), 7.19 (1H, d), 7.13–7.10 (2H, m), 3.69 (5H, s), 3.61 (2H, s), 2.15 (3H, s) ppm.

LRMS (electrospray): m/z [M+NH₄]⁺ 224, [M+Na]⁺ 229.

Preparation 54

(3-Bromo-phenyl)-acetic acid methyl ester

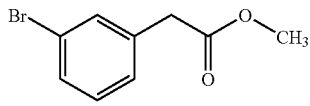

Acetyl chloride (0.7 ml, 9.3 mmol) was slowly added to a solution of (3-bromo-phenyl)-acetic acid (20.0 g, 93 mmol) in methanol (500 ml) at 0° C. under nitrogen and the reaction was allowed to warm gradually to room temperature over a period of 5 hours. The solvent was removed in vacuo and the residue dissolved in dichloromethane, dried (sodium sulfate) and concentrated in vacuo to give the title compound as a colourless oil (20.6 g).

¹H NMR (400 MHz, CDCl₃): δ=7.37–7.45 (2H, m), 7.24–7.17 (2H, m), 3.70 (3H, s), 3.59 (2H, s) ppm.

LRMS (electrospray): m/z [M+Na]⁺ 253/255.

Preparation 55

[4-(2-Oxo-propyl)-phenyl]-acetic acid methyl ester

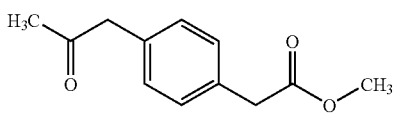

Prepared using the method for preparation 53 using the ester from preparation 56 to give the title compound as a pale yellow oil.

¹H NMR (400 MHz, CDCl₃): δ=7.25 (2H, d), 7.16 (2H, d), 3.68 (3H, s), 3.60 (2H, s), 2.15 (3H, s) ppm.

LRMS (electrospray): m/z [M+NH₄]⁺ 224, [M+Na]⁺ 229.

Preparation 56

(4-Bromo-phenyl)-acetic acid methyl ester

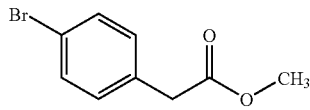

Prepared using the method for preparation 54 using (4-bromo-phenyl)-acetic acid to give the title compound as a colourless oil.

¹H NMR (400 MHz, CDCl₃): δ=7.44 (2H, d), 7.15 (2H, d), 3.69 (3H, s), 3.58 (2H, s) ppm.

LRMS (electrospray): m/z [M+Na]⁺ 253/255.

Preparation 57

N-(4-Aminomethyl-benzyl)-2,2-diphenyl-acetamide

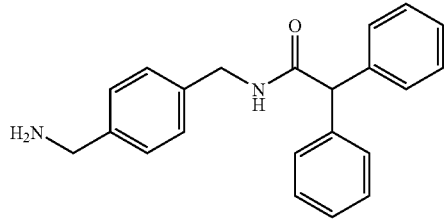

A solution of the amide from preparation 58 (200 mg, 0.43 mmol) in a mixture of ethanol (15 ml) and ethyl acetate (1 ml) was hydrogenated at 60 psi/50° C. over 10% palladium-on-charcoal (40 mg) for 3 h. The resulting mixture was filtered through arbocel and the filtrate concentrated in vacuo to give an oil. Purification by flash column chromatography on silica gel eluting with CH₂Cl₂:MeOH (98:2 to 90:10, by volume) gave the title compound (87 mg) as a white solid.

¹H NMR (400 MHz, DMSO d₆): δ=8.72–8.68 (1H, m), 7.31–7.11 (14H, m), 4.98 (1H, s), 4.26 (2H, d), 3.69 (2H, bs) ppm.

LRMS (electrospray): m/z [M+H]⁺ 331.

Preparation 58

[4-(Diphenylacetylamino-methyl)-benzyl]-carbamic acid benzyl ester

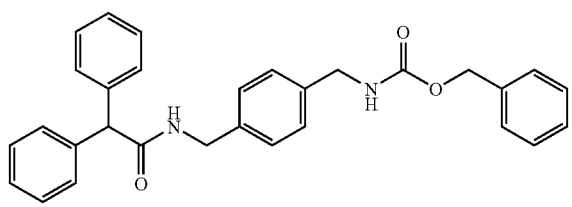

Prepared according to the method for preparation 1 using the amine from preparation 59 and the appropriate acid to give the title compound as a colourless solid.

¹H NMR (400 MHz, DMSO d₆): δ=8.75–8.68 (1H, m), 7.75–7.72 (1H, m), 7.33–7.08 (19H, m), 5.01 (2H, s), 4.98 (1H, s), 4.26 (2H, d), 4.14 (2H, d) ppm.

LRMS (electrospray): m/z [M−H]⁻ 634.

Preparation 59

(4-Aminomethyl-benzyl)-carbamic acid benzyl ester

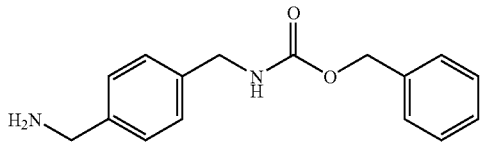

A solution of 1,4-bis(aminomethyl)benzene (10.0 g, 74 mmol) and triethylamine (9.8 ml, 74 mmol) in dichloromethane (480 ml) was cooled to 0° C. and treated with a solution of benzylchloroformate (10.5 ml, 74 mmol) in dichloromethane (250 ml). The resulting mixture was allowed to warm gradually to room temperature of a period of 16 h. The solvent was removed in vacuo and the residue partitioned between ethyl acetate (450 ml) and 1M aqueous sodium hydroxide (300 ml). The resulting biphasic mixture was filtered and the organic phase separated, dried (magnesium sulfate) and reduced in vacuo to give a waxy solid. Trituration with hot ethyl acetate followed by concentration of the liquors gave the title compound as a waxy solid (7.4 g).

$^1$H NMR (400 MHz, CDCl$_3$): δ=7.83–7.72 (1H, m), 7.36–7.15 (9H, m), 5.02 (2H, s), 4.16 (2H, d), 3.66 (2H, s) ppm.
LRMS (electrospray): m/z [M+H]$^+$ 271.

Preparation 60

(4-Aminomethyl-benzyl)-benzhydryl-amine hydrochloride

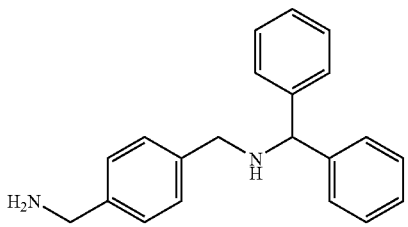

A solution of the nitrile from preparation 61 (10.43 g, 35 mmol) in tetrahydrofuran (100 ml) was added dropwise to a suspension of lithium aluminium-hydride (2.66 g, 70 mmol) in tetrahydrofuran (80 ml) under a nitrogen atmosphere. The resulting suspension was heated to reflux for 5 hours and then cooled to room temperature. Water (2.66 ml) was added followed by 15% w/w aqueous sodium hydroxide (2.66 ml), followed by water (7.98 ml). The resulting suspension was filtered and the filtrate reduced in vacuo to give a colourless oil. The oil was redissolved in chloroform (200 ml), dried (sodium sulfate) and reduced in vacuo to give a yellow oil. The oil was treated with a solution of hydrogen chloride in ether to give the hydrochloride salt which was crystallised (isopropanol/methanol) to give the title compound as a colourless solid.

$^1$H NMR (60 MHz, DMSO$_{d6}$): δ=11.00 (1H, m), 9.10 (2H, m), 7.78–7.15 (14H, m), 5.50–5.30 (1H, m), 4.10–3.90 (4H, m) ppm.

Preparation 61

4-[(Benzhydryl-amino)-methyl]-benzonitrile hydrogen chloride

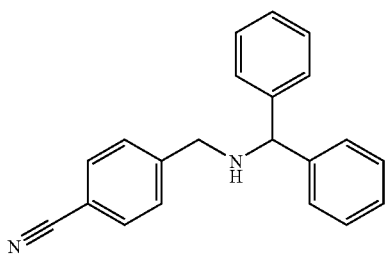

A suspension of 4-cyanobenzylbromide (13.72 g, 70 mmol), benzhydrylamine (13.79 g, 75 mmol) and potassium carbonate (16.8 g, 140 mmol) in ethanol (200 ml) was heated to reflux for 5 hours. The reaction mixture was cooled to room temperature and filtered. The filtrate was reduced in vacuo and the residue crystallised from a mixture of hexane/isopropanol to give the free base as a colourless solid. The compound was treated with hydrogen chloride in ether and then recrystallised (isopropanol) to give the title compound as a colourless solid.

$^1$H NMR (60 MHz, DMSO$_{d6}$): δ=11.30–10.50 (2H, m), 7.82–7.15 (14H, m), 5.10–4.90 (1H, m), 4.20–3.90 (2H, m) ppm.

Preparation 62

2-Benzyloxy-ethylamine

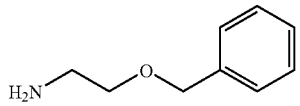

Prepared according to Synthetic Communications 1995, 25(6), 907–913.

$^1$H NMR (400 MHz, CDCl$_3$): δ=7.37–7.29 (5H, m), 4.54 (2H, s), 3.52 (2H, t), 2.89 (2H, t), 1.52 (2H, s) ppm.
LRMS (APCI): m/z [M+H]$^+$ 152.

Preparation 63

2-(3-Phenyl-propoxy)-ethylamine

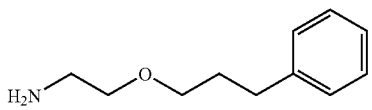

Prepared according to Synthetic Communications 1995, 25(6), 907–913.

$^1$H NMR (400 MHz, CDCl$_3$): δ=7.30–7.26 (2H, m), 7.20–7.16 (3H, m), 3.47–3.43 (4H, m), 2.86 (2H, t), 2.68 (2H, t), 1.95–1.88 (2H, m), 1.51 (2H, s) ppm.
LRMS (APCI): m/z [M+H]$^+$ 180.

Preparation 64

2-(Naphthalen-1-ylmethoxy)-ethylamine

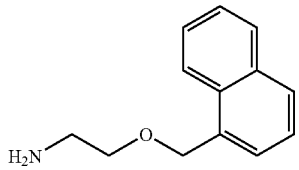

Sodium hydride (1.00 g, 0.025 mmol) was added portionwise to a cooled (0° C.) solution of ethanolamine (1.51 ml, 0.025 mmol) in tetrahydrofuran (25 ml). The reaction mixture was then heated to reflux for 30 minutes. Chloromethylnaphthalene (3.4 ml, 0.0225 mmol) was added and the reaction mixture heated at reflux for a further 3 hours. The reaction mixture was cooled to room temperature and the solvent removed in vacuo. The residue was partitioned between dichloromethane (50 ml) and 1 N aqueous sodium hydroxide (50 ml). The organic phase was separated and the aqueous phase extracted with dichloromethane (2×50 ml). The combined organic extracts were reduced in vacuo and the residue purified by flash column chromatography eluting with dichloromethane:methanol: 880 ammonia (98:2:0.2 changing to 90:10:1 by volume) to give the title compound as a colourless oil (1.80 g, 40%).

$^1$H NMR (400 MHz, CDCl$_3$): δ=8.13 (1H, d), 7.87 (1H, d), 7.82 (1H, d), 7.54–7.42 (4H, m), 4.98 (2H, s), 3.59 (2H, t), 2.89 (2H, t), 1.65 (2H, s) ppm.

LRMS (electrospray): m/z [M+H]$^+$ 202, [M+Na]$^+$ 214.

Preparation 65

4-Aminomethyl-N-methyl-benzenesulfonamide

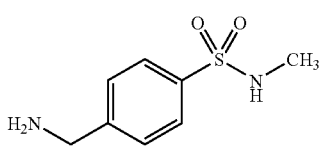

A solution of the nitrile from preparation 74 (1.27 g, 6.47 mmol) in methanol (60 ml) at 0° C. was treated with cobalt chloride (1.68 g, 12.9 mmol) and the resulting mixture left to stir for 5 minutes prior to the addition of sodium borohydride (2.40 g, 63.4 mmol). The resulting suspension was allowed to warm gradually to room temperature. After 16 hours 3N hydrochloric acid (10 ml) was added and the mixture stirred for 10 minutes. 880 Ammonia solution (20 ml). Silica gel was added to the mixture and the solvent removed in vacuo to give a free flowing powder which was purified by flash column chromatography eluting with dichloromethane:methanol: 880 ammonia (97:3:0.5 changing to 90:10:1 by volume) to give the title compound as a colourless waxy solid (1.12 g, 86%).

$^1$H NMR (400 MHz, CD$_3$OD): δ=7.80 (2H, d), 7.55 (2H, d), 3.85 (2H, s), 2.42 (3H, s) ppm.

LRMS (APCI): m/z [M+H]$^+$ 201.

Preparation 66

4-Aminomethyl-N-ethyl-benzenesulfonamide

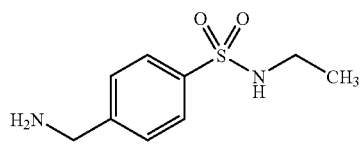

Prepared according to the method for preparation 65 using the nitrile from preparation 75 to give the title compound as a colourless oil.

$^1$H NMR (400 MHz, CD$_3$OD): δ=7.79 (2H, d), 7.52 (2H, d), 3.87 (2H, s), 2.86 (2H, q), 1.04 (3H, t) ppm.

LRMS (APCI): m/z [M+H]$^+$ 215.

Preparation 67

4-Aminomethyl-N-benzyl-benzenesulfonamide hydrochloride

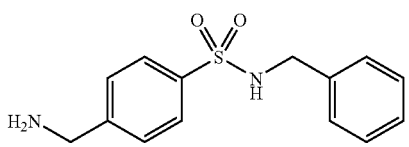

Prepared according to the method for preparation 65 using the nitrile from preparation 76 to give the title compound as a colourless oil.

$^1$H NMR (400 MHz, CD$_3$OD): δ=7.78 (2H, d), 7.48 (2H, d), 7.22–7.18 (5H, m), 4.02 (2H, s), 3.82 (2H, s) ppm.

LRMS (APCI): m/z [M+H]$^+$ 277.

Preparation 68

3-Aminomethyl-N-ethyl-benzenesulfonamide

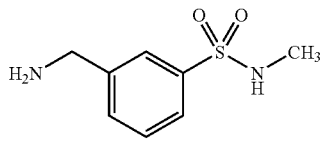

Prepared according to the method for preparation 65 using the nitrile from preparation 71 to give the title compound as a colourless oil.

$^1$H NMR (400 MHz, CD$_3$OD): δ=7.83 (1H, s), 7.75 (1H, d), 7.60 (1H, d), 7.55 (1H, m), 3.85 (2H, s), 2.50 (3H, s) ppm.

LRMS (APCI): m/z [M+H]$^+$ 215.

Preparation 69

3-Aminomethyl-N-ethyl-benzenesulfonamide

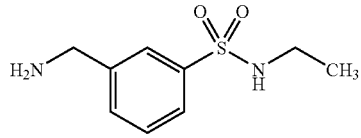

Prepared according to the method for preparation 65 using the nitrile from preparation 72 to give the title compound as a colourless oil.

$^1$H NMR (400 MHz, CD$_3$OD): δ=7.83 (1H, s), 7.72 (1H, d), 7.58 (1H, d), 7.52 (1H, m), 3.88 (2H, s), 2.89 (2H, q), 1.05 (3H, t) ppm.

LRMS (APCI): m/z [M+H]$^+$ 215.

Preparation 70

3-Aminomethyl-N-benzyl-benzenesulfonamide

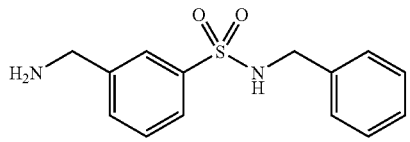

Prepared according to the method for preparation 65 using the nitrile from preparation 73 to give the title compound as colourless oil.

$^1$H NMR (400 MHz, CD$_3$OD): δ=7.77 (1H, s), 7.70 (1H, d), 7.54 (1H, d), 7.48 (1H, t), 7.23–7.18 (5H, m), 4.07 (2H, s), 3.82 (2H, s) ppm.

LRMS (APCI): m/z [M+H]$^+$ 277.

Preparation 71

3-Cyano-N-ethyl-benzenesulfonamide

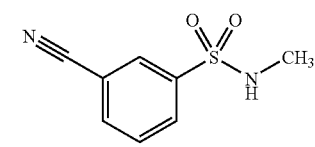

Methylamine hydrochloride (736 mg, 10.9 mmol) was added to a solution of 3-cyano benzene sulfonyl chloride (2.0 g, 9.9 mmol) and triethylamine (3.45 ml, 24.7 mmol) in tetrahydrofuran (30 ml) and the resulting mixture left to stir at room temperature under a nitrogen atmosphere for 16 h hours. The reaction mixture was diluted with water (30 ml) and ethyl acetate (50 ml). The organic phase was separated and dried (sodium sulfate) and reduced in vacuo to give the title compound as a colourless solid (1.68 g, 86%).

$^1$H NMR (400 MHz, CD$_3$OD): δ=8.17 (1H, s), 8.12 (1H, d), 7.98 (1H, d), 7.77 (1H, t), 2.56 (3H, s) ppm.

LRMS (APCI): m/z [M–H]$^-$ 195.

Preparation 72

3-Cyano-N-ethyl-benzenesulfonamide

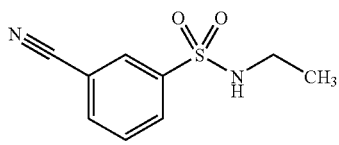

Prepared using the method for preparation 71 using the appropriate amine to give the title compound as a pale yellow solid.

$^1$H NMR (400 MHz, CD$_3$OD): δ=8.17 (1H, s), 8.11 (1H, d), 7.98 (1H, d), 7.75 (1H, t), 2.92 (2H, q), 1.06 (3H, t) ppm.

LRMS (APCI): m/z [M+Na]$^+$ 228, [M–H]$^-$ 209.

Preparation 73

N-Benzyl-3-cyano-benzenesulfonamide

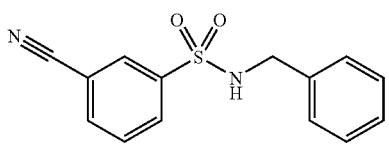

Prepared using the method for preparation 71 using the appropriate amine to give the title compound as a pale orange solid.

$^1$H NMR (400 MHz, CD$_3$OD): δ=8.02 (2H, m), 7.88 (1H, d), 7.62 (1H, t), 7.18 (5H, m), 4.17 (2H, s) ppm.

LRMS (APCI): m/z [M+H]$^+$ 273, [M+NH$_4$]$^+$ 290, [M–H]$^-$ 271.

Preparation 74

4-Cyano-N-methyl-benzenesulfonamide

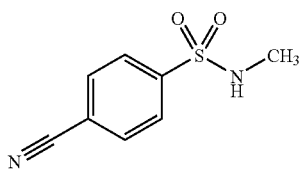

Prepared using the method for preparation 71 using the appropriate amine and sulfonyl chloride to give the title compound as a pale orange solid.

$^1$H NMR (400 MHz, CD$_3$OD): δ=7.98–7.95 (4H, m), 2.56 (3H, s) ppm.

LRMS (APCI): m/z [M+NH$_4$]$^+$ 214, [M–H]$^-$ 195.

Preparation 75

4-Cyano-N-ethyl-benzenesulfonamide

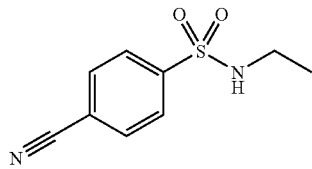

Prepared using the method for preparation 71 using the appropriate amine and sulfonyl chloride to give the title compound as a yellow solid.

$^1$H NMR (400 MHz, CD$_3$OD): δ=7.99 (2H, d), 7.93 (2H, d), 2.93 (2H, q), 1.06 (3H, t) ppm.

LRMS (APCI): m/z [M+NH$_4$]$^+$ 228, [M−H]$^-$ 209.

Preparation 76

N-Benzyl-4-cyano-benzenesulfonamide

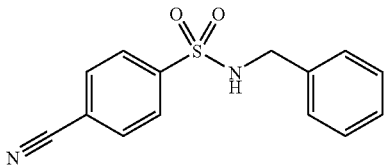

Prepared using the method for preparation 71 using the appropriate amine and sulfonyl chloride to give the title compound as a pale yellow solid.

$^1$H NMR (400 MHz, DMSO$_{d6}$): δ=8.35 (1H, bs), 8.03 (2H, d), 7.91 (2H, d), 7.25–7.18 (5H, m), 4.02 (2H, s) ppm.

LRMS (APCI): m/z [M−H]$^-$ 271.

In Vitro Activity of the Compounds of Formula (1)

The ability of the compounds of the formula (1) to act as potent β2 agonists therefore mediating smooth muscle relaxation may be determined by the measure of the effect of beta-2 adrenergic receptor stimulation on electrical field stimulated-contraction of guinea pig trachea strips.

Guinea-pig trachea

Male, Dunkin-Hartley guinea pigs (475–525 g) are killed by CO$_2$ asphyxiation and exsanguination from the femoral artery and the trachea is isolated. Four preparations are obtained from each animal, starting the dissection immediately below the larynx and taking 2.5 cm length of trachea. The piece of trachea is opened by cutting the cartilage opposite the trachealis muscle, then transverse sections, 3–4 cartilage rings wide, are cut. The resulting strip preparations are suspended in 5 ml organ baths using cotton threads tied through the upper and lower cartilage bands. The strips are equilibrated, un-tensioned, for 20 minutes in a modified Krebs Ringer buffer (Sigma K0507) containing 3 μM Indomethacin (Sigma 17378), 10 μM Guanethidine (Sigma G8520) and 10 μM Atenolol (Sigma A7655), heated at 37° C. and gassed with 95% O$_2$/5% CO$_2$, before applying an initial tension of 1 g. The preparations are allowed to equilibrate for a further 30–45 minutes, during which time they are re-tensioned (to 1 g) twice at 15-minute intervals. Changes in tension are recorded and monitored via standard isometric transducers coupled to a data-collection system (custom-designed at Pfizer). Following the tensioning equilibration, the tissues are subjected to electrical field stimulation (EFS) using the following parameters: 10 s trains every 2 minutes, 0.1 ms pulse width, 10 Hz and just-maximal voltage (25 Volts) continuously throughout the length of the experiment. EFS of post-ganglionic cholinergic nerves in the trachea results in monophasic contractions of the smooth muscle and twitch height is recorded. The organ baths are constantly perfused with the above-described Krebs Ringer buffer by means of a peristaltic pump system (pump flow rate 7.5 ml/minute) throughout the experiment, with the exception of when a beta-2 agonist according to the present invention is added, the pump is then stopped for the time of the cumulative dosing to the bath and started again after maximal response is reached for the wash-out period.

Experimental Protocol for Assessment of Potency and Efficacy

Following equilibration to EFS, the peristaltic pump is stopped and the preparations 'primed' with a single dose of 300 nM isoprenaline (Sigma I5627) to establish a maximal response in terms of inhibition of the contractile EFS response. The isoprenaline is then washed out over a period of 40 minutes. Following the priming and wash-out recovery, a standard curve to isoprenaline is carried out on all tissues (Isoprenaline Curve 1) by means of cumulative, bolus addition to the bath using half log increments in concentration. The concentration range used is $1^{e-9}$ to $1^e/3^{e-6}$ M. At the end of the isoprenaline curve the preparations are washed again for 40 minutes before commencing a second curve, either to isoprenaline (as internal control) or a beta-2 agonist according to the present invention. Beta-2 agonist responses are expressed as percentage inhibition of the EFS response. Data for beta-2 agonist are normalised by expressing inhibition as a percentage of the maximal inhibition induced by isoprenaline in Curve 1. The EC$_{50}$ value for beta-2 agonist according to the present invention refers to the concentration of compound required to produce half maximal effect. Data for beta-2 agonists according to the present invention are then expressed as relative potency to isoprenaline defined by the ratio (EC$_{50}$ beta-2 agonist)/(EC$_{50}$ Isoprenaline).

Confirmation of Beta-2 Mediated Functional Activity

Beta-2 agonist activity of test compounds is confirmed using the protocol above, however, prior to constructing the curve to beta-2 agonist according to the present invention, the preparations are pre-incubated (for a minimum of 45 minutes) with 300 nM ICI 118551 (a selective β$_2$ antagonist) which results in the case of a beta-2 mediated effect in a rightward-shift of the test compound dose response curve.

It has thus been found that the compounds of formula (1) according to the present invention that have been tested show a relative potency to Isoprenaline which is comprised between 0.008 and 2.0.

According to another alternative, the agonist potency for the β2 receptor of the compounds of the formula (1) may also be determined by the measure of the concentration of compound according to the present invention required to produce half maximal effect (EC$_{50}$) for the β2 receptor.

Compound Preparation 10 mM/100% DMSO (dimethylsulfoxide) stock of compound is diluted to required top dose in 4% DMSO. This top dose is used to construct a 10-point semi-log dilution curve, all in 4% DMSO. Isoprenaline (Sigma, I-5627) was used as a standard in every experiment and for control wells on each plate. Data was expressed as % Isoprenaline response.

Cell Culture

CHO (Chinese Hamster Ovary) cells recombinantly expressing the human β2 adrenergic receptor (from Kobilka et al., PNAS 84: 46–50, 1987 and Bouvier et al., Mol Pharmacol 33: 133–139 1988 CHOhβ2) were grown in Dulbeccos MEM/NUT MIX F12 (Gibco, 21331-020) supplemented with 10% foetal bovine serum (Sigma, F4135, Lot 90K8404 Exp 09/04), 2 mM glutamine (Sigma, G7513), 500 μg/ml geneticin (Sigma, G7034) and 10 μg/ml puromycin (Sigma, P8833). Cells were seeded to give about 90% confluency for testing.

Assay Method

25 μl/well each dose of compound was transferred into a cAMP-Flashplate® (NEN, SMP004B), with 1% DMSO as basal controls and 100 nM Isoprenaline as max controls. This was diluted 1:2 by the addition of 25 μl/well PBS. Cells were trypsinised (0.25% Sigma, T4049), washed with PBS (Gibco, 14040-174) and resuspended in stimulation buffer (NEN, SMP004B) to give $1 \times 10^6$ cells/ml CHOhB2. Compounds were incubated with 50 μl/well cells for 1 hour. Cells were then lysed by the addition of 100 μl/well detection buffer (NEN, SMP004B) containing 0.18 μCi/ml $^{125}$I-cAMP (NEN, NEX-130) and plates were incubated at room temperature for a further 2 hours. The amount of $^{125}$I-cAMP bound to the Flashplate® was quantified using a Topcount NXT (Packard), normal counting efficiency for 1 minute. Dose-response data was expressed as % Isoprenaline activity and fitted using a four parameter sigmoid fit.

It has thus been found that the compounds of formula (1) according to the present invention that are illustrated in examples 1 to 33 above show a β2 cAMP $EC_{50}$ between 0.01 nM and 2 nM.

The invention claimed is:

1. A compound of the formula (1):

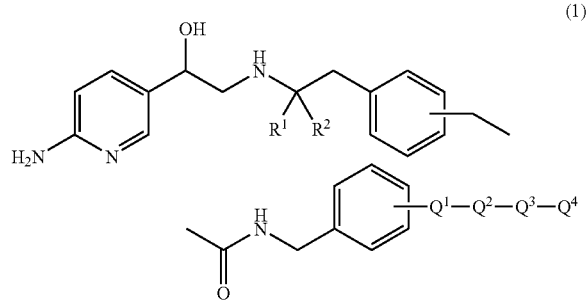

(1)

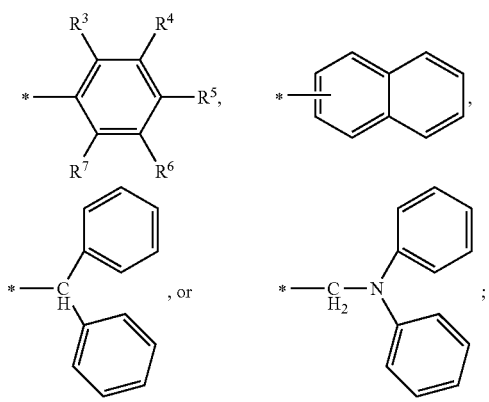

or a pharmaceutically acceptable salt thereof, wherein the $CH_2$—$C(=O)NH$-benzyl-$Q^1$-$Q^2$-$Q^3$-$Q^4$ group is substituted on the meta or para position of the benzene ring to which it is attached;

$R^1$ and $R^2$ are independently H or $C_1$–$C_4$ alkyl;

$Q^1$ is $(CH_2)_n$;

$Q^2$ is —$C(=O)NH$—, —$NHC(=O)$—, or —$SO_2NH$—;

$Q^3$ is a single bond, $C_1$–$C_4$ alkylenyl optionally substituted with OH, or —$(CH_2)_m$—O—$(CH_2)_p$—;

$Q^4$ is

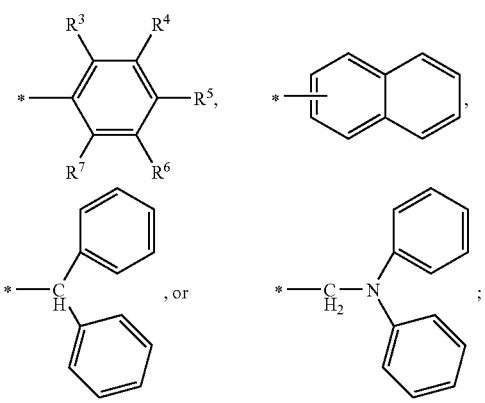

wherein $R^3$, $R^4$, $R^5$, $R^6$ and $R^7$ are independently H, —$OR^8$ —$SO_2NR^8R^9$; or —$CH_2NHC(=O)NHR^9$, provided at least 4 of $R^3$, $R^4$, $R^5$, $R^6$ and $R^7$ are H.

8. A compound of claim 1 wherein $Q^4$ is

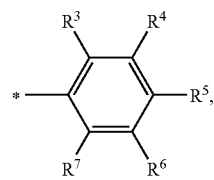

wherein $R^3$, $R^4$, $R^5$, $R^6$ and $R^7$ are independently H, —$OR^8$ provided at least 2 of $R^3$, $R^4$, $R^5$, $R^6$ and $R^7$ are H;

* represents the attachment point to $Q^3$;

$R^3$, $R^4$, $R^5$, $R^6$ and $R^7$ are independently H, $C_1$–$C_4$ alkyl, $OR^8$, $SR^8$, halo, $CF_3$, $OCF_3$, $COOR^9$, $SO_2NR^8R^9$, $CONR^8R^9$, $NHR^8R^9$, $NHCOR^9$, or $CH_2NHC(=O)NHR^9$, provided at least 2 of $R^3$, $R^4$, $R^5$, $R^6$ and $R^7$ are H;

$R^8$ is H or $C_1$–$C_4$ alkyl;

$R^9$ is H, $C_1$–$C_4$ alkyl, benzyl optionally substituted with 1, 2, 3 or 4 $C_1$–$C_4$ alkoxy, or

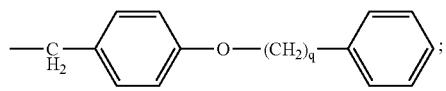

n is 0 or 1;

m and p are independently 1, 2 or 3; and q is 0, 1, 2 or 3.

2. A compound of claim 1 wherein $R^1$ is H and $R^2$ is $CH_3$.

3. A compound of claim 1 wherein $R^1$ is $CH_3$ and $R^2$ is $CH_3$.

4. A compound of claim 1 wherein n is 0 and $Q^2$ is —$C(=O)NH$— or —$SO_2NH$—.

5. A compound of claim 1 wherein n is 1 and $Q^2$ is —$NH$—$C(=O)$—.

6. A compound of claim 1 wherein $Q^3$ is a single bond, —$CH_2$—, —$CH(CH_3)CH(OH)$—, —$CH(CH_3)$—, —$CH(CH_2OH)CH_2$—, —$(CH_2)_2$—, —$(CH_2)_2OCH_2$— or —$(CH_2)$—O—$(CH_2)_3$—.

7. A compound of claim 1 wherein $Q^4$ is

—SO$_2$NR$^8$R$^9$; or —CH$_2$—NHC(=O)NH—R$^9$, provided at least 4 of R$^3$, R$^4$, R$^5$, R$^6$ and R$^7$ are H.

9. The (R,R)-stereoisomer of a compound of claim 1 wherein R$^1$ is hydrogen and R$^2$ is C$_1$–C$_4$ alkyl.

10. A compound of claim 1 wherein the —CH$_2$—C(=O)NH-benzyl-Q$^1$-Q$^2$-Q$^3$-Q$^4$ group is substituted on the meta position of the benzene ring to which it is attached.

11. 4-{[2-(3-{2-[(2R)-2-(6-Amino-pyridin-3-yl)-2-hydroxy-ethylamino]-propyl}-phenyl)-acetylamino]-methyl}-N-(3,4-dimethoxy-benzyl)-benzamide;

4-{[2-(3-{2-[(2R)-2-(6-amino-pyridin-3-yl)-2-hydroxy-ethylamino]-propyl}-phenyl)-acetylamino]-methyl}-N-(4-sulfamoyl-benzyl)-benzamide;

4-{[2-(3-{2-[(2R)-2-(6-amino-pyridin-3-yl)-2-hydroxy-ethylamino]-propyl}-phenyl)-acetylamino]-methyl}-N-(2-ethoxy-benzyl)-benzamide;

4-{[2-(3-{2-[(2R)-2-(6-amino-pyridin-3-yl)-2-hydroxy-ethylamino]-propyl}-phenyl)-acetylamino]-methyl}-N-[(1R)-1-(4-methoxy-phenyl)-ethyl]-benzamide;

4-{[2-(3-{2-[(2R)-2-(6-amino-pyridin-3-yl)-2-hydroxy-ethylamino]-propyl}-phenyl)-acetylamino]-methyl}-N-((1R)-1-hydroxymethyl-2-phenyl-ethyl)-benzamide;

4-{[2-(3-{2-[(2R)-2-(6-amino-pyridin-3-yl)-2-hydroxy-ethylamino]-propyl}-phenyl)-acetylamino]-methyl}-N-((1R, 2S)-2-hydroxy-1-methyl-2-phenyl-ethyl)-benzamide;

4-{[2-(3-{2-[(2R)-2-(6-amino-pyridin-3-yl)-2-hydroxy-ethylamino]-propyl}-phenyl)-acetylamino]-methyl}-N-((1 S, 2R)-2-hydroxy-1-methyl-2-phenyl-ethyl)-benzamide;

4-{[2-(3-{2-[(2R)-2-(6-amino-pyridin-3-yl)-2-hydroxy-ethylamino]-propyl}-phenyl)-acetylamino]-methyl}-N-[2-(3-methoxy-phenyl)-ethyl]-benzamide;

4-{[2-(3-{(2R)-2-[(2R)-2-(6-amino-pyridin-3-yl)-2-hydroxy-ethylamino]-propyl}-phenyl)-acetylamino]-methyl}-N-(3,4-dimethoxy-benzyl)-benzamide;

4-{[2-(3-{(2R)-2-[(2R)-2-(6-amino-pyridin-3-yl)-2-hydroxy-ethylamino]-propyl}-phenyl)-acetylamino]-methyl}-N-(2-ethoxy-benzyl)-benzamide;

4-{[2-(3-{(2R)-2-[(2R)-2-(6-amino-pyridin-3-yl)-2-hydroxy-ethylamino]-propyl}-phenyl)-acetylamino]-methyl}-N-(4-hydroxy-3-methoxy-benzyl)-benzamide;

4-{[2-(3-{(2R)-2-[(2R)-2-(6-amino-pyridin-3-yl)-2-hydroxy-ethylamino]-propyl}-phenyl)-acetylamino]-methyl}-N-(4-sulfamoyl-benzyl)-benzamide;

4-{[2-(3-{(2R)-2-[(2R)-2-(6-amino-pyridin-3-yl)-2-hydroxy-ethylamino]-propyl}-phenyl)-acetylamino]-methyl}-N-((1R, 2S)-2-hydroxy-1-methyl-2-phenyl-ethyl)-benzamide;

N-(4-{[2-(3-{(2R)-2-[(2R)-2-(6-amino-pyridin-3-yl)-2-hydroxy-ethylamino]-propyl}-phenyl)-acetylamino]-methyl}-benzyl)-2,2-diphenyl-acetamide;

2-(3-{(2R)-2-[(2R)-2-(6-amino-pyridin-3-yl)-2-hydroxy-ethylamino]-propyl}-phenyl)-N-{4-[(benzhydryl-amino)-methyl]-benzyl}-acetamide;

4-{[2-(3-{(2R)-2-[(2R)-2-(6-amino-pyridin-3-yl)-2-hydroxy-ethylamino]-propyl}-phenyl)-acetylamino]-methyl}-N-(2-benzyloxy-ethyl)-benzamide;

4-{[2-(3-{(2R)-2-[(2R)-2-(6-amino-pyridin-3-yl)-2-hydroxy-ethylamino]-propyl}-phenyl)-acetylamino]-methyl}-N-[2-(3-phenyl-propoxy)-ethyl]-benzamide;

4-{[2-(3-{(2R)-2-[(2R)-2-(6-amino-pyridin-3-yl)-2-hydroxy-ethylamino]-propyl}-phenyl)-acetylamino]-methyl}-N-[2-(naphthalen-1-ylmethoxy)-ethyl]-benzamide;

4-{[2-(3-{(2R)-2-[(2R)-2-(6-amino-pyridin-3-yl)-2-hydroxy-ethylamino]-propyl}-phenyl)-acetylamino]-methyl}-N-(3-benzylsulfamoyl-benzyl)-benzamide;

4-{[2-(3-{(2R)-2-[(2R)-2-(6-amino-pyridin-3-yl)-2-hydroxy-ethylamino]-propyl}-phenyl)-acetylamino]-methyl}-N-(4-methylsulfamoyl-benzyl)-benzamide;

4-{[2-(3-{(2R)-2-[(2R)-2-(6-amino-pyridin-3-yl)-2-hydroxy-ethylamino]-propyl}-phenyl)-acetylamino]-methyl}-N-(4-ethylsulfamoyl-benzyl)-benzamide;

4-{[2-(3-{(2R)-2-[(2R)-2-(6-amino-pyridin-3-yl)-2-hydroxy-ethylamino]-propyl}-phenyl)-acetylamino]-methyl}-N-(3-benzylsulfamoyl-benzyl)-benzamide;

4-{[2-(3-{(2R)-2-[(2R)-2-(6-amino-pyridin-3-yl)-2-hydroxy-ethylamino]-propyl}-phenyl)-acetylamino]-methyl}-N-(3-methylsulfamoyl-benzyl)-benzamide;

4-{[2-(3-{(2R)-2-[(2R)-2-(6-amino-pyridin-3-yl)-2-hydroxy-ethylamino]-propyl}-phenyl)-acetylamino]-methyl}-N-(3-ethylsulfamoyl-benzyl)-benzamide;

2-(3-{(2R)-2-[(2R)-2-(6-amino-pyridin-3-yl)-2-hydroxy-ethylamino]-propyl}-phenyl)—N-(4-benzylsulfamoyl-benzyl)-acetamide hydrochloride;

4-{[2-(3-{(2R)-2-[(2R)-2-(6-amino-pyridin-3-yl)-2-hydroxy-ethylamino]-propyl}-phenyl)-acetylamino]-methyl}-N-[4-(3-benzyl-ureidomethyl)-benzyl]-benzamide;

4-{[2-(3-{(2R)-2-[(2R)-2-(6-amino-pyridin-3-yl)-2-hydroxy-ethylamino]-propyl}-phenyl)-acetylamino]-methyl}-N-{4-[3-(3,4-dimethoxy-benzyl)-ureidomethyl]-benzyl}-benzamide;

4-{[2-(3-{(2R)-2-[(2R)-2-(6-amino-pyridin-3-yl)-2-hydroxy-ethylamino]-propyl}-phenyl)-acetylamino]-methyl}-N-{4-[3-(4-phenoxy-benzyl)-ureidomethyl]-benzyl}-benzamide; or 4-{[2-(3-{(2R)-2-[(2R)-2-(6-amino-pyridin-3-yl)-2-hydroxy-ethylamino]-propyl}-phenyl)-acetylamino]-methyl}-N-{4-[3-(4-benzyloxy-benzyl)-ureidomethyl]-benzyl}-benzamide.

12. A process for preparing a compound of claim 1 comprising the steps of (a) coupling an acid of formula (3),

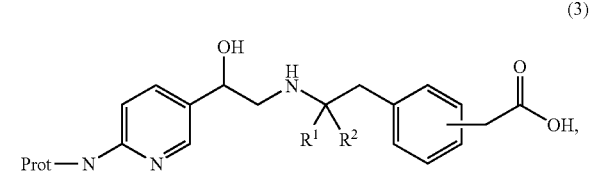

(3)

wherein Prot is a protecting group, with an amine of formula (4),

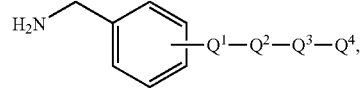

(4)

to form a compound of formula (2),

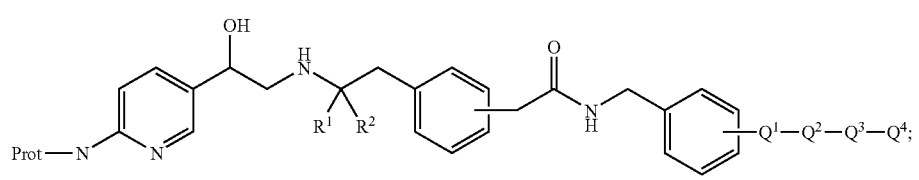

(2)

(b) removing the protecting group "Prot" from the compound of formula (2) to form the compound of claim 1; and (c) isolating the compound of claim 1.

13. A pharmaceutical composition comprising a compound claim 1 or a pharmaceutically acceptable salt thereof and a pharmaceutically acceptable excipient or additive.

14. A method of treating is asthma, chronic bronchoconstriction, acute bronchoconstriction, bronchitis, small airways obstruction, emphysema, obstructive airways disease, inflammatory airways disease or bronchiectasis in a mammal which method comprises administering to said mammal in need thereof a therapeutically effective amount of the compound of claim 1 or a pharmaceutically acceptable salt thereof and a pharmaceutically acceptable excipient or additive.

15. A method of claim 14 wherein said asthma is atopic asthma, non-atopic asthma, allergic asthma, atopic bronchial IgE-mediated asthma, bronchial asthma, essential asthma, true asthma, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome or bronchiolytis.

16. A method of claim 14 wherein said obstructive airways disease or said inflammatory airways disease is chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS).

17. A method of claim 14 wherein said bronchitis is chronic bronchitis, acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis or vesicular bronchitis.

18. A method of claim 14 wherein said bronchiectasis is cylindric bronchiectasis, sacculated bronchiectasis, fusiform bronchiectasis, capillary bronchiectasis, cystic bronchiectasis, dry bronchiectasis or follicular bronchiectasis.

19. A method of any one of claims 14–18 wherein said mammal is a human.

* * * * *